US007578041B2

(12) United States Patent
Weber et al.

(10) Patent No.: US 7,578,041 B2
(45) Date of Patent: Aug. 25, 2009

(54) METHOD OF REDUCING A STENT IN CROSS-SECTION

(75) Inventors: Jan Weber, Maple Grove, MN (US); Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 11/739,552

(22) Filed: Apr. 24, 2007

(65) Prior Publication Data

US 2007/0193328 A1    Aug. 23, 2007

Related U.S. Application Data

(62) Division of application No. 10/788,088, filed on Feb. 26, 2004, now Pat. No. 7,207,204.

(51) Int. Cl.
B21D 39/00    (2006.01)
B21J 7/16    (2006.01)

(52) U.S. Cl. .......................................... 29/515; 72/402

(58) Field of Classification Search .................. 29/515, 29/516, 508, 243.517, 237, 282, 283.5, 234; 72/402, 416, 412, 357, 409.19, 409.01
See application file for complete search history.

(56) References Cited

U.S. PATENT DOCUMENTS

| 1,578,172 | A | 3/1926 | Valentin | 72/377 |
|---|---|---|---|---|
| 3,000,424 | A | 9/1961 | Weise | 72/369 |
| 3,101,766 | A | 8/1963 | Floyd | 72/472 |
| 3,146,519 | A | 9/1964 | Redwine | 29/862 |
| 3,555,607 | A | 1/1971 | Epain et al. | 18/16 |
| 3,606,789 | A | 9/1971 | Kozusnik | 72/402 |
| 3,732,715 | A | 5/1973 | Zamorano | 72/253.1 |
| 4,379,397 | A | 4/1983 | Langr | 72/95 |
| 4,454,657 | A | 6/1984 | Yasumi | 33/644 |
| 4,489,588 | A | 12/1984 | Svercl et al. | 72/402 |
| 4,901,707 | A | 2/1990 | Schiff | 128/1 D |
| 4,994,071 | A | 2/1991 | MacGregor | 606/194 |
| 5,138,864 | A | 8/1992 | Tarpill | 72/410 |
| 5,644,945 | A | 7/1997 | Baldwin et al. | 72/402 |
| 5,692,294 | A | 12/1997 | Casey | 29/753 |
| 5,723,004 | A | 3/1998 | Dereume et al. | 623/1 |
| 5,725,519 | A | 3/1998 | Penner et al. | 606/1 |

(Continued)

OTHER PUBLICATIONS

U.S. Appl. No. 10/788,088, filed Apr. 24, 2007, Weber et al.

*Primary Examiner*—John C Hong
(74) *Attorney, Agent, or Firm*—Crompton, Seager & Tufte, LLC

(57) ABSTRACT

In one embodiment, an apparatus for shaping an article may comprise a plurality of movable dies arranged to form a chamber whose size may be varied by moving the dies. Each of the dies may have a contacting surface for contacting the article to be shaped. The chamber may have a first portion having a first cross-section and a second portion having a second cross-section. Either portion may include a taper. The first portion may have a differently shaped cross-section than the second portion. The first portion may have a cross-section of greater area than the second portion. The longitudinal axis of the first portion may be offset from the longitudinal axis of the second portion.

24 Claims, 88 Drawing Sheets

U.S. PATENT DOCUMENTS

| | | | |
|---|---|---|---|
| 5,755,735 A | 5/1998 | Richter et al. | 606/194 |
| 5,810,873 A | 9/1998 | Morales | 606/198 |
| 5,836,952 A | 11/1998 | Davis et al. | 606/108 |
| 5,893,852 A | 4/1999 | Morales | 606/108 |
| 5,920,975 A | 7/1999 | Morales | 29/282 |
| 5,974,652 A | 11/1999 | Kimes et al. | 29/516 |
| 5,992,000 A | 11/1999 | Humphrey et al. | 29/516 |
| 6,063,102 A | 5/2000 | Morales | 606/198 |
| 6,082,990 A | 7/2000 | Jackson et al. | 425/517 |
| 6,096,027 A | 8/2000 | Layne | 606/1 |
| 6,108,886 A | 8/2000 | Kimes et al. | 29/280 |
| 6,125,523 A | 10/2000 | Brown et al. | 29/516 |
| 6,141,855 A | 11/2000 | Morales | 29/516 |
| 6,149,680 A | 11/2000 | Shelso et al. | 623/1.11 |
| 6,167,605 B1 | 1/2001 | Morales | 29/282 |
| 6,309,383 B1 | 10/2001 | Campbell et al. | 606/1 |
| 6,352,547 B1 | 3/2002 | Brown et al. | 606/198 |
| 6,360,577 B2 | 3/2002 | Austin | 72/402 |
| 6,387,117 B1 | 5/2002 | Arnold, Jr. et al. | 623/1.1 |
| 6,481,262 B2 | 11/2002 | Ching et al. | 72/416 |
| 6,568,235 B1 | 5/2003 | Kokish | 72/402 |
| 6,629,350 B2 | 10/2003 | Motsenbocker | 29/283.5 |
| 6,640,412 B2 | 11/2003 | Iancea | 29/505 |
| 6,651,478 B1 | 11/2003 | Kokish | 72/402 |
| 6,718,814 B2 | 4/2004 | Bartrom et al. | 72/402 |
| 6,868,709 B2 | 3/2005 | Adams et al. | 72/342.92 |
| 2001/0001890 A1 | 5/2001 | Austin | 29/282 |
| 2002/0138966 A1 | 10/2002 | Motsenbocker | 29/516 |
| 2003/0056360 A1 | 3/2003 | Brown et al. | 29/516 |
| 2003/0150250 A1 | 8/2003 | Shortt | 72/235 |
| 2003/0192164 A1 | 10/2003 | Austin | 29/505 |
| 2004/0199239 A1* | 10/2004 | Austin et al. | 623/1.11 |

* cited by examiner

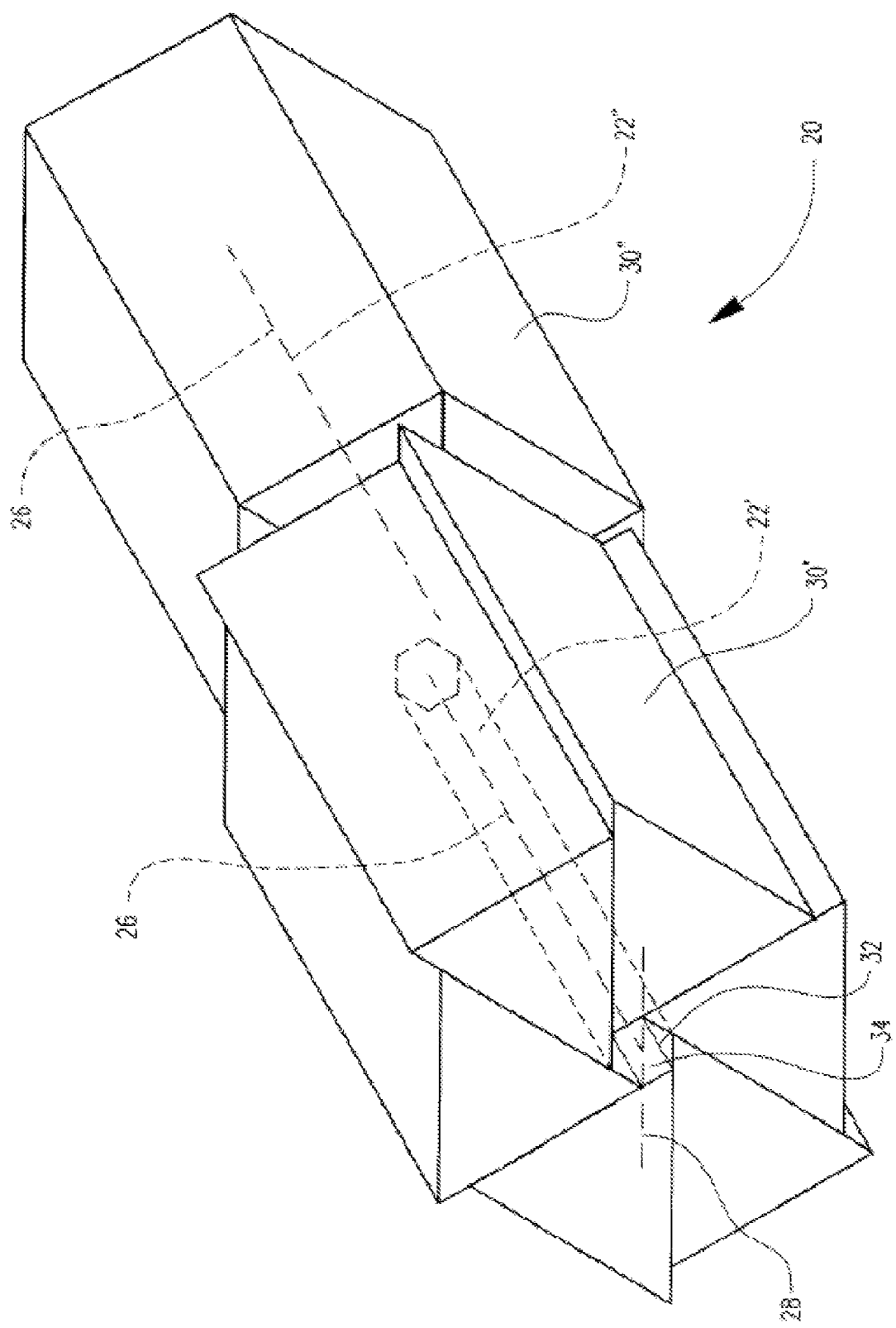

METHOD OF REDUCING A STENT IN CROSS-SECTION

CROSS-REFERENCE TO RELATED APPLICATIONS

This application claims the benefit of and is a divisional application of U.S. application Ser. No. 10/788,088, filed Feb. 26, 2004, now U.S. Pat. No. 7,207,204, the entire disclosure of which is hereby incorporated herein by reference in its entirety.

BACKGROUND OF THE INVENTION

The use of stents is well known. A stent is an elongated device used to support an intraluminal wall. In the case of stenosis, a stent provides a conduit for blood in the area of the stenosis. Stents may taper or otherwise include portions of varying cross sectional shapes and areas. Bifurcated stents having multiple tubular sections, each section having a distinct cross sectional shape and/or area are also well known. The longitudinal axis of any given section may be offset from that of the other sections. Examples of bifurcated stents are shown in U.S. Pat. No. 5,723,004 to Dereume et al., U.S. Pat. No. 4,994,071 to MacGregor, and U.S. Pat. No. 5,755,735 to Richter, et al., the entire disclosures of which are incorporated herein by reference.

Devices for reducing the diameter of cylindrical stents are generally known, such as described in U.S. Pat. No. 6,360,577 to Austin, the entire disclosure of which is incorporated herein by reference.

There remains a need for an apparatus capable of reducing the diameter of tapered and bifurcated stents and other implantable medical devices which may have non-circular cross-sections, cross-sections of non-uniform shape and/or area, non-uniform cross sections along a longitudinal axis, portions having offset axes, and various combinations of such features.

There further remains a need for an apparatus capable of reducing the diameter of an implantable medical device that avoids subjecting localized portions of the device to high pressure.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In some embodiments, the invention may comprise a device for reducing the diameter of a bifurcated stent.

In some embodiments, the invention may comprise a device for non-uniformly reducing the diameter of a stent so as to provide a taper to the stent.

In some embodiments, the invention may comprise an apparatus for crimping, swaging, loading and/or otherwise shaping an article. The article may be shaped to a non-uniform cross section along a longitudinal axis.

In some embodiments, the invention may comprise a device for reducing the diameter of a stent, the device having an iris that comprises a nonregular polygon.

In some embodiments, the invention may comprise a device for reducing the diameter of a stent, the device having a first longitudinal axis offset from a second longitudinal axis.

In some embodiments, the invention may comprise a device for reducing the diameter of a stent, the device having two or more portions. The portions may differ in cross section. For example, the cross sections may differ in size and/or shape.

In some embodiments, the invention may comprise a device for reducing a stent having two portions, the first portion of the stent having a larger diameter than the second portion of the stent. The longitudinal axis of the first portion may further be offset from the longitudinal axis of the second portion. The first portion may further include an elliptical cross-section. The second portion may further include a taper.

In one embodiment, an apparatus for shaping an article may comprise a plurality of movable dies arranged to form a chamber whose size may be varied by moving the dies. Each of the dies may have a contacting surface for contacting the article to be shaped. The contacting surface of at least one of the dies may be non-planar.

In another embodiment, an apparatus for shaping an article may comprise a plurality of movable dies arranged to form an iris and defining a chamber whose size may be varied by moving the dies. The dies may be configurable to provide at least a portion of the chamber with a cross-section comprising a non-regular polygon.

In another embodiment, an apparatus for shaping an article may comprise a plurality of movable dies arranged to form a chamber whose size may be varied by moving the dies. The chamber may have a length from the first end of the chamber to the second end of the chamber. Each of the dies may extend the length of the chamber. The dies may be configurable to provide the chamber with at least two regions. The first region may have a different cross-section than the second region.

In one embodiment, a method of reducing a bifurcated stent in cross-section may comprise providing a stent crimper comprising a plurality of movable dies arranged to form a chamber whose size may be varied by moving the dies. The chamber may have a length from a first end to a second end. The dies may be configurable to provide the chamber with at least two regions, the cross-section of the first region being different than the cross-section of the second region. A bifurcated stent may next be disposed within the chamber, and the size of the chamber may be reduced. The reduction may shape a first portion of the stent with a first shape and a second portion of the stent with a second shape of different geometry from the first shape.

In another embodiment, another method of reducing a stent in cross-section may comprise providing a stent crimper comprising a plurality of movable dies arranged to form a chamber whose size may be varied by moving the dies. The chamber may have a length from a first end to a second end. The dies may be configurable to provide at least a portion of the chamber with a smoothly tapering shape. A stent may next be disposed within the chamber, and the size of the chamber may be reduced so that the blades contact the stent and reduce the cross-section of the stent and impart a taper to the stent.

In further embodiments, a method of crimping one or more marker bands to a catheter tube may comprise providing an apparatus comprising a plurality of movable dies arranged to form a chamber whose size may be varied by moving the dies. The chamber may have a length from a first end to a second end. The dies may be configurable so that the chamber includes at least one enlarged region having a cross-section that is larger than the cross-section of the remainder of the chamber. A catheter tube with at least one marker band disposed thereabout may be placed in the chamber. The size of the chamber may then be reduced so as to contact the marker band(s) and crimp them onto the catheter. Thus, a plurality of marker bands may be crimped simultaneously, each marker band being crimped to specific predetermined tolerances which may be similar or dissimilar. Each marker band may be disposed in a region of the chamber having a larger cross-section. Marker bands may also be reduced to a noncircular cross section, such as an ellipse. Marker bands may also be crimped to a tapered shape along the axis.

In various embodiments, the inventive apparatus may also be used as a variable size and/or variable shape balloon mold. Thus, the invention is further directed to a method of forming a medical balloon. A balloon precursor or preform prepared through any suitable technique known in the art may provided. The preform may be placed in an apparatus having a plurality of movable dies arranged to form a chamber whose size may be varied by moving the dies. Each of the dies may have a contacting surface for contacting the preform. The chamber may be set to a predetermined size prior to placement of the preform therein or after placement of the preform therein. An inflation fluid is supplied to the balloon preform to expand the balloon preform until it contacts the blades. The preform may optionally be heated prior to, during or after the blowing step. The thus formed balloon is then pressure relieved and removed from the apparatus. The size of the chamber may be increased before removal of the balloon if desired.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described various embodiments of the invention.

BRIEF DESCRIPTION OF THE SEVERAL VIEWS OF THE DRAWING(S)

A detailed description of the invention is hereafter described with specific reference being made to the drawings.

FIG. 21B is an isometric view of an apparatus shown in FIG. 21, wherein the first portion is in another open configuration and the second portion is in a closed configuration.

DETAILED DESCRIPTION OF THE INVENTION

Figure 1A:
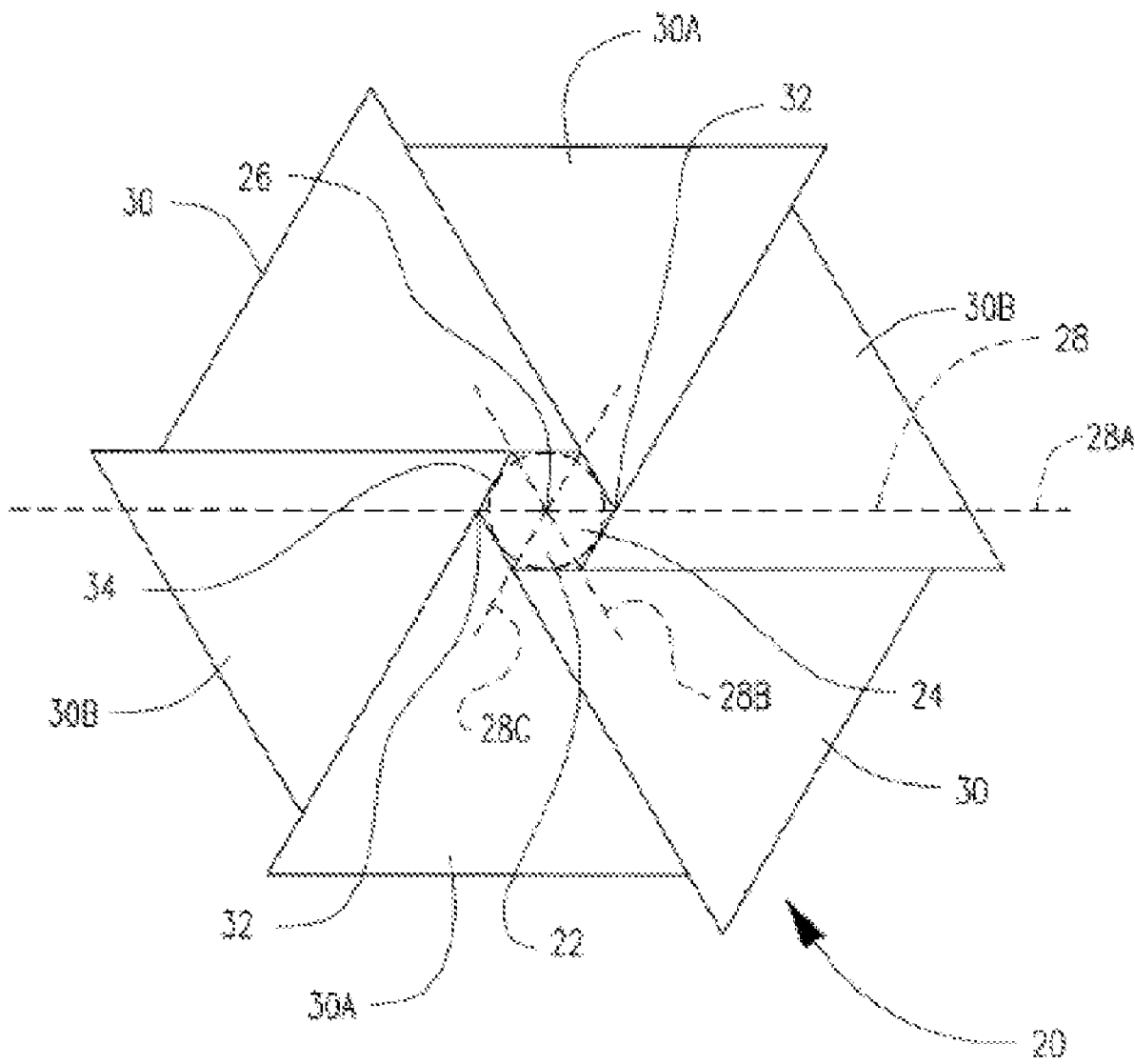
FIG. 1A is an end view of an apparatus for reducing the size of an article in an open configuration.

While this invention may be embodied in many different forms, there are described in detail herein specific embodiments of the invention. This description is an exemplification of the principles of the invention and is not intended to limit the invention to the particular embodiments illustrated.

The following disclosure describes a plurality of embodiments of an apparatus for reducing the size or otherwise shaping an implantable medical device, such as a stent. The apparatus may be provided with a number of different features as herein discussed. For example, various embodiments may include a single chamber or multiple chambers. A cross-section of a first chamber may be similar or dissimilar in shape or size from the cross-section of a second chamber included in the apparatus. The longitudinal axis of a first chamber may be offset from the longitudinal axis of a second chamber. Chambers may further include a taper along the length and other features as described herein.

A chamber may be formed by a plurality of dies which may move in relation to one another to vary the size and shape of the chamber. Dies may be moved using structures and methods as disclosed herein and as known in the art. For example, U.S. Pat. No. 6,360,577 to Austin discloses an apparatus for manipulating a medical device formed of at least three coupled movable blades which are disposed about a reference circle to form an aperture, each blade being in communication with an actuation device which is capable of moving the blade to alter the size of the aperture. U.S. Pat. No. 6,568,235 to Kokish discloses a device having a stationary disk and a drive disk for imparting movement to a number of wedges attached to linear sliders on the stationary disk. As rotational movement is imparted by the drive disk to the wedges, the wedges move in a linear direction. U.S. Pat. No. 6,629,350 to Motsenbocker discloses a device having a stationary base member, a rotatable drive hub which is moveable in relation to the stationary base member and a crimping head aligned with respect to the stationary base member and to the rotatable drive hub. A stent may be crimped upon rotation of the rotatable hub. U.S. Pat. No. 6,360,577, U.S. Pat. No. 6,568,235 and U.S. Pat. No. 6,629,350 are incorporated herein by reference in their entireties.

For the purposes of this disclosure, like reference numerals in the figures shall refer to like features unless otherwise indicated.

Figure 1B:
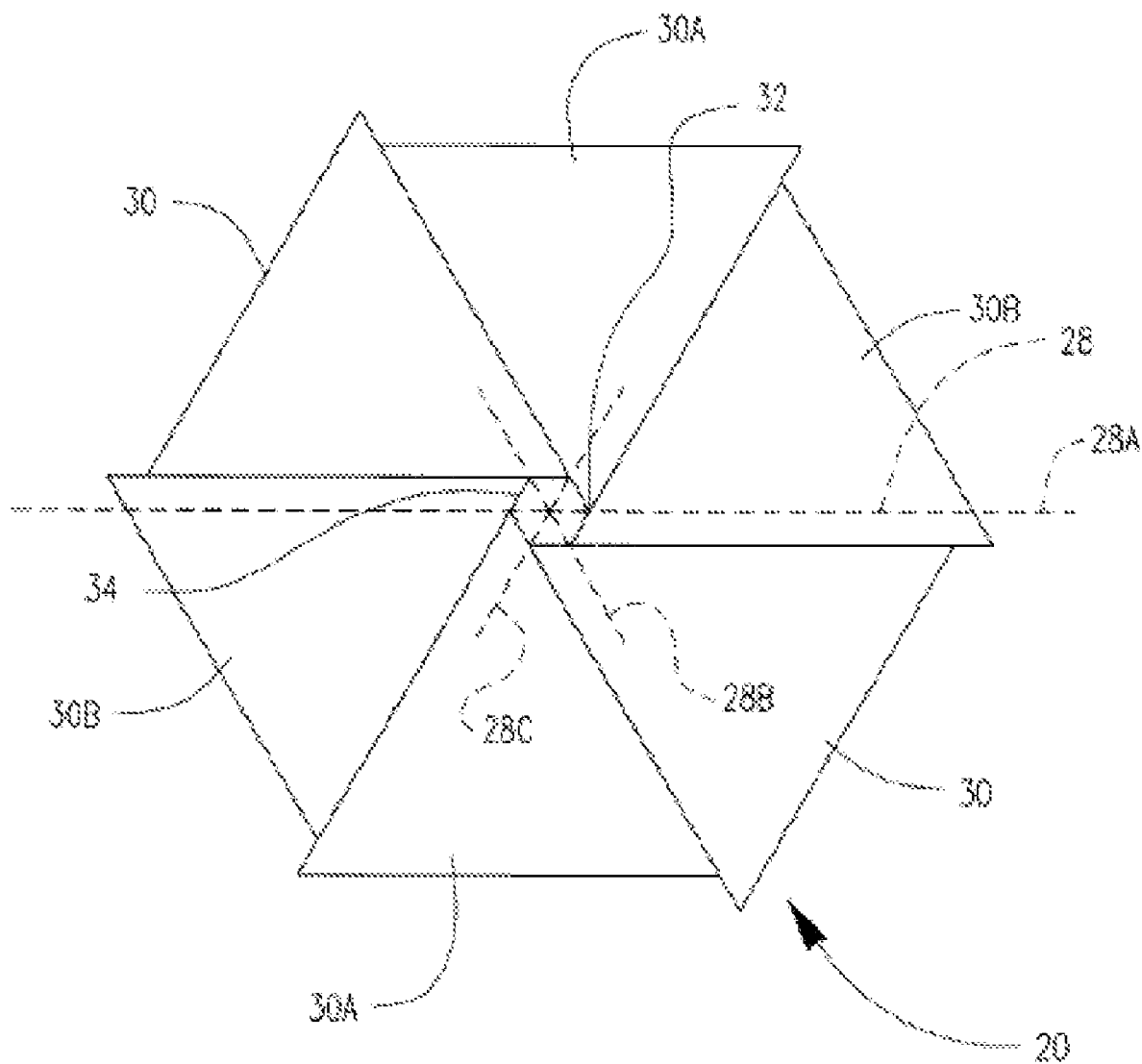
FIG. 1B shows the apparatus of FIG. 1A in a partially open configuration.
Figure 1C:
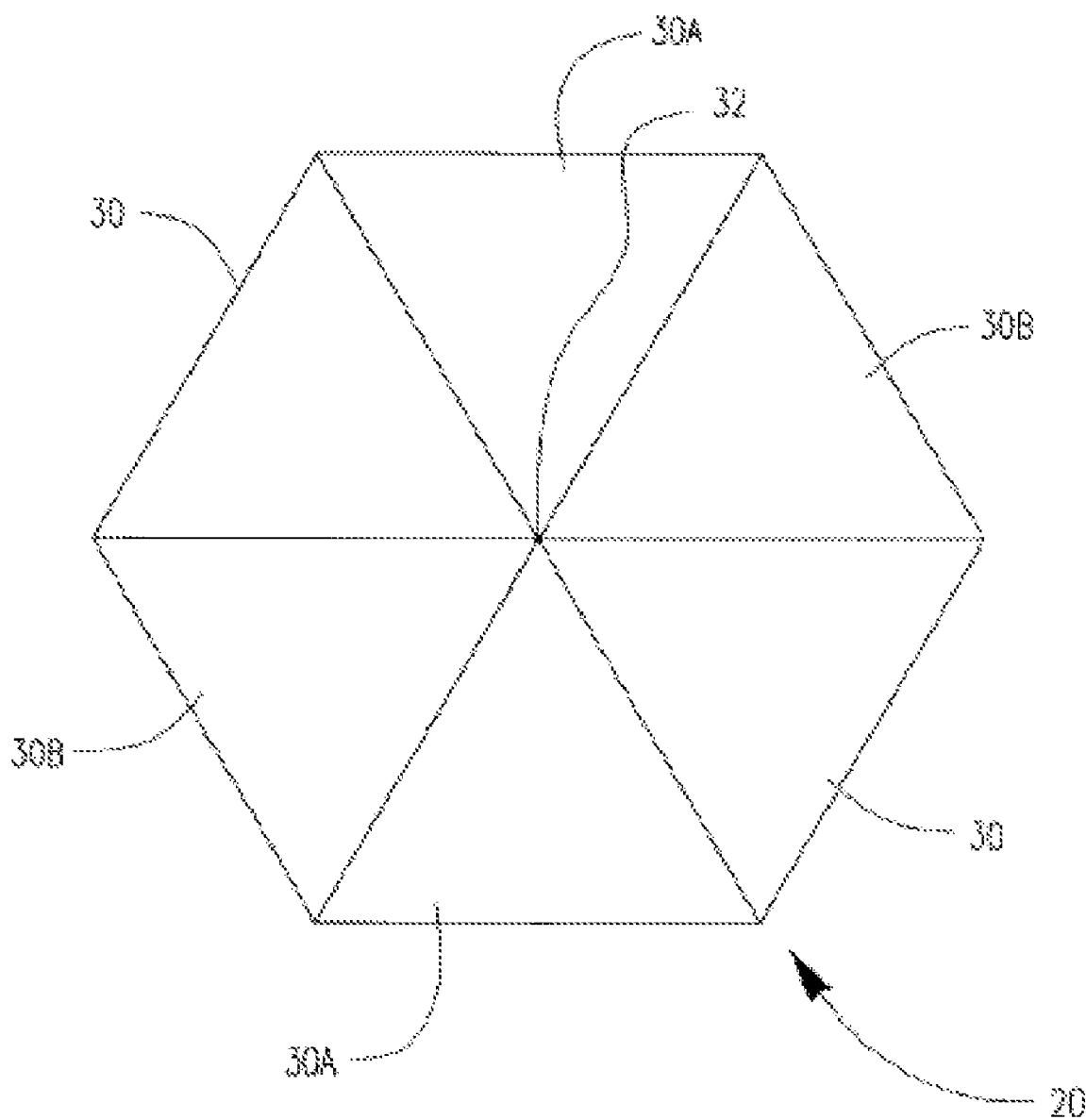
FIG. 1C shows the apparatus of FIG. 1A in a closed configuration.
Figure 1D:
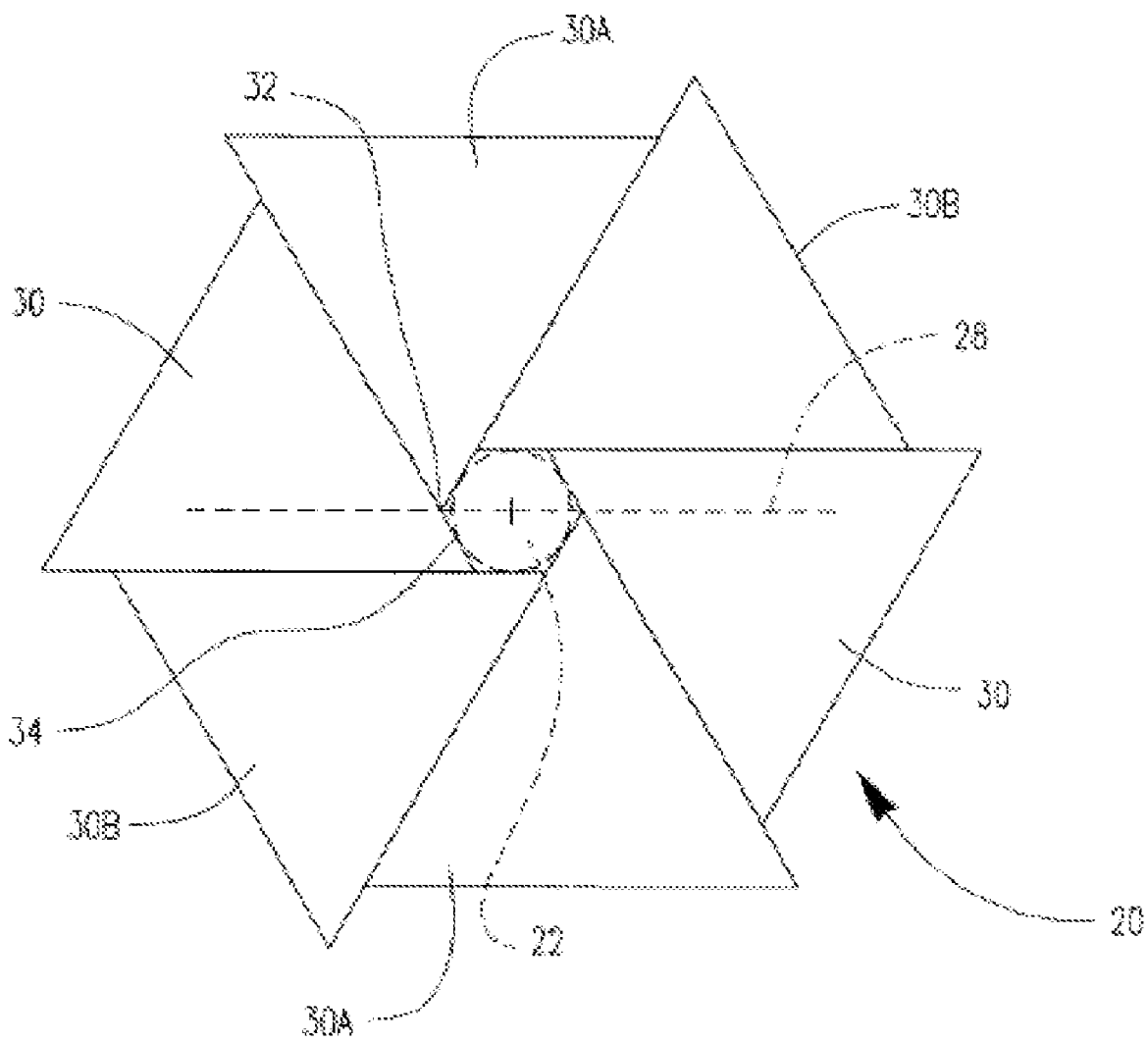
FIG. 1D shows the apparatus of FIG. 1A in another open configuration.
Figure 2:
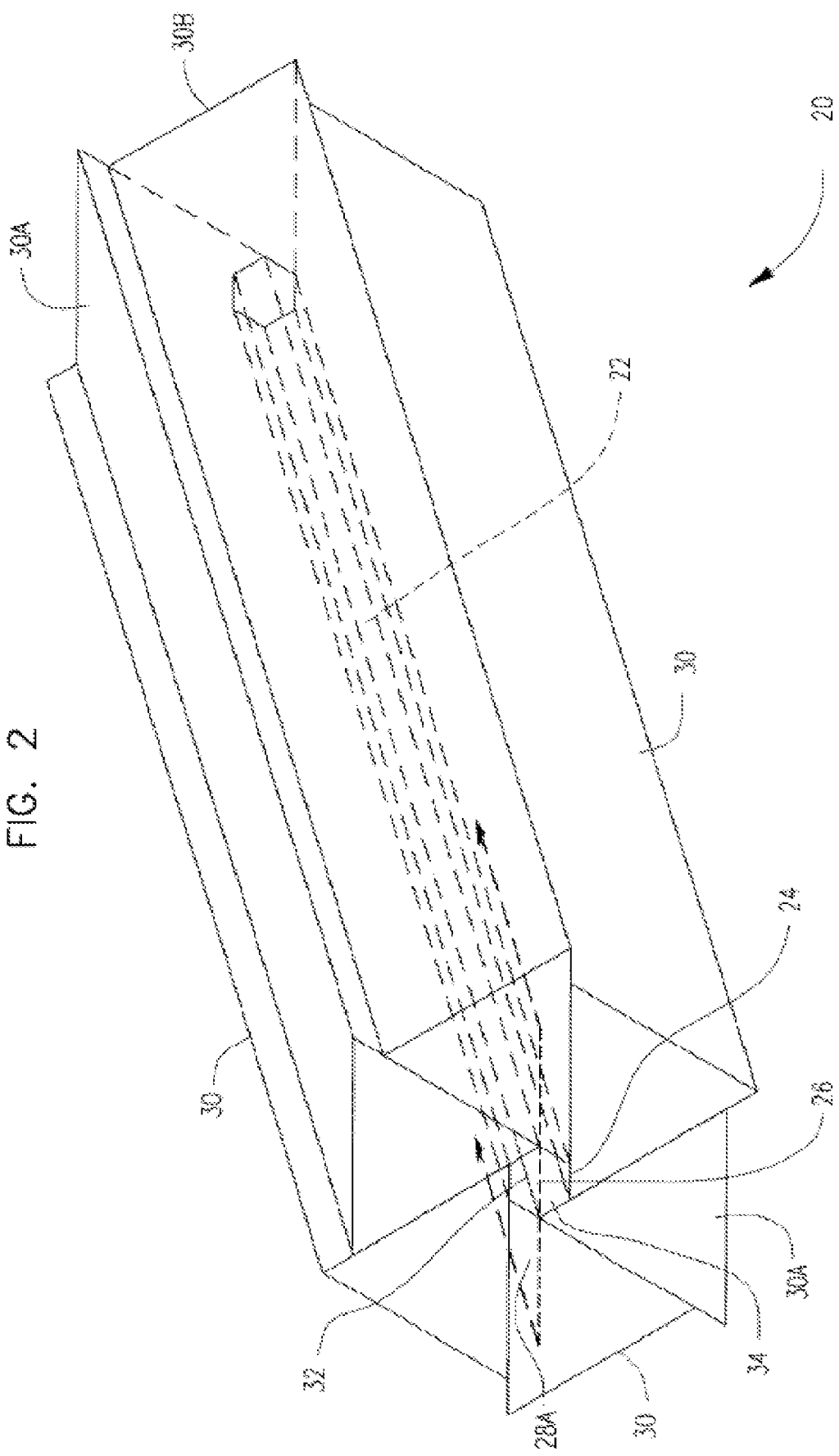
FIG. 2 is an isometric view of an apparatus for reducing the size of an article.

Referring to FIGS. 1A-2, an embodiment of an apparatus 20 for shaping an article is shown. Generally, the apparatus 20 may include a plurality of movable dies 30 arranged to form a chamber 22 having a length and cross-sectional area. Wall surface portions of the dies 30 which bound the chamber 22 may comprise a contacting surface 34 and may contact an article placed within the chamber 22. Wall surfaces or contacting surfaces 34 which bound the chamber 22 may comprise an iris 24 in the shape of a regular polygon, wherein all sides and all interior angles of the iris 24 are the same. Desirably, an iris 24 is orthogonal to the central longitudinal axis of the chamber 22. A zero point 26 may be the center point of an iris 24.

Each die 30 may include an edge 32. An edge 32 may extend the length of the chamber 22, as best shown in FIG. 2. As the size of the chamber is varied by moving the dies 30, an edge 32 of each die 30 may travel along or follow a respective movement path 28, such as the movement paths shown by lines 28A, 28B and 28C in FIG. 1A. Represented in a two-dimensional drawing, a movement path 28 may comprise a line. Represented in a three-dimensional drawing, a movement path 28 may comprise a plane, such as plane 28A as shown in FIG. 2. The movement path 28 shown by plane 28A of FIG. 2 corresponds to the movement path 28 shown by line 28A of FIG. 1A. Any given point along an edge 32 of a die 30 may move according to a movement path line.

FIG. 1B shows the apparatus 20 in a reduced configuration, wherein the size of the chamber 22, and the corresponding iris 24 size, has been reduced. A comparison of FIGS. 1A and 1B shows that each die 30 has moved in an inward direction, and the edge 32 of each die 30 has traversed along its respective movement path 28A, 28B, 28C toward the zero point 26.

Dies 30 that are opposite one another across the iris 24 may have edges 32 that travel along different portions of a common movement path line 28A, 28B, 28C on opposite sides of a zero point 26. For example, dies 30A each have an edge 32 that moves along movement path 28A. The dies 30 may move relative to one another such that the size of the iris 24 may be reduced until all of the edges 32 meet at a zero point 26. Thus, all movement path lines 28A, 28B, 28C may intersect at the zero point 26. The movement path lines 28A, 28B, 28C may form a plurality of identical central angles having their vertices at the zero point 26.

FIG. 1A shows the apparatus 20 in an open configuration wherein the edges 32 of the dies are offset from the zero point 26. FIG. 1C shows the apparatus 20 in a closed configuration, wherein the edges 32 of the dies 30 have met at the zero point 26. FIG. 1D shows the apparatus 20 in another open configuration wherein the edges 32 of the dies are offset from the zero point 26 in the opposite direction from that shown in FIG. 1A. Thus, from the open configuration of FIG. 1A, the edges 32 of the dies 30 may move to the zero point 26, thereby closing the chamber 22, as shown in FIG. 1C. The die edges 32 may continue to move through the zero point 26 along the respective movement path lines 28A, 28B, 28C to reopen the chamber 22 according to another open configuration as shown in FIG. 1D. The configuration shown in FIG. 1D may be a mirror image of the configuration shown in FIG. 1A.

The surface which comprises a contacting surface 34 may change as the chamber 22 configuration changes from a first open configuration to another or second open configuration.

Other embodiments of the invention may also be able to close from a first open configuration and reopen to another or second open configuration.

Figure 3:
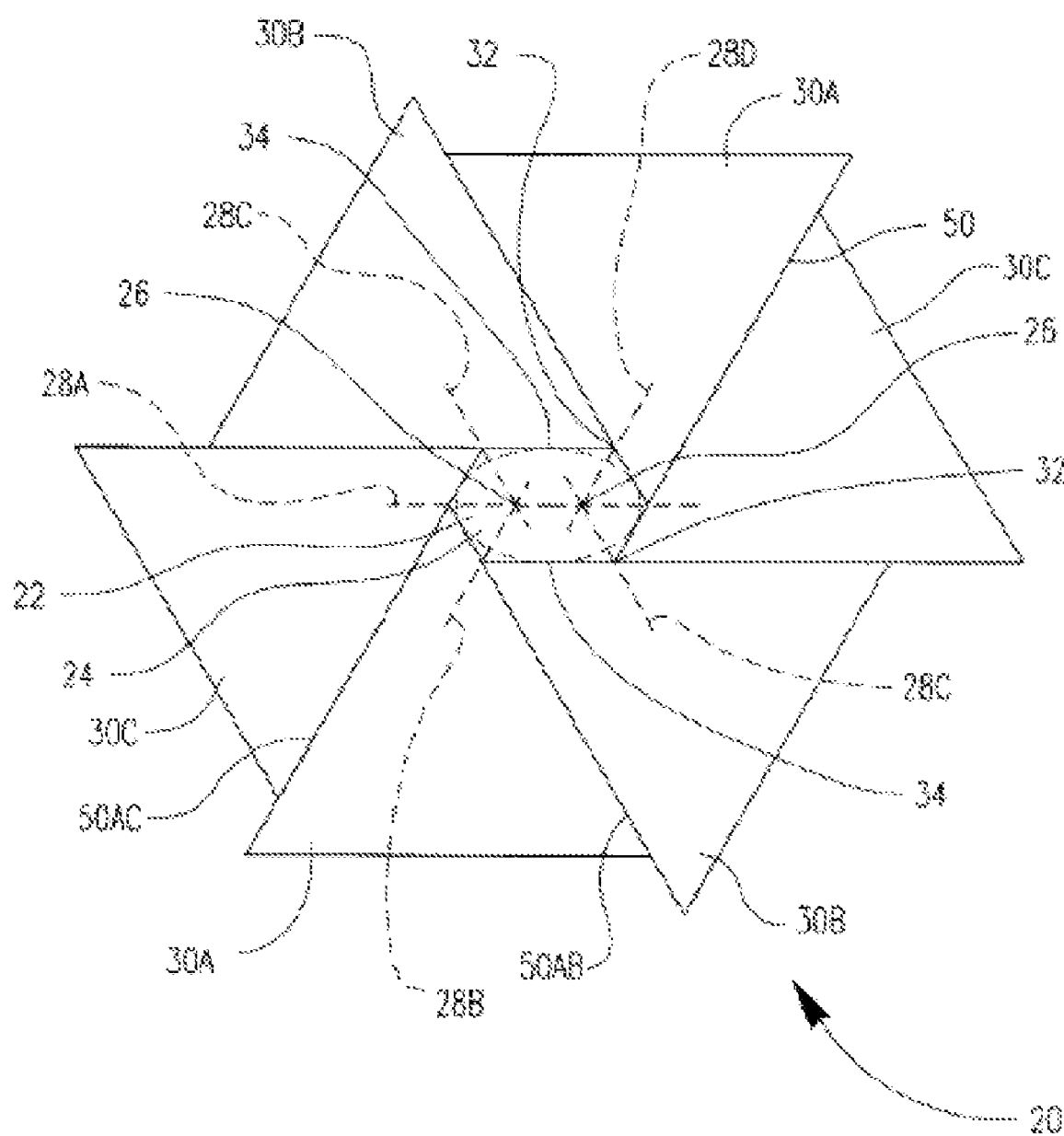
FIG. 3 is an end view of an apparatus for reducing the size of an article having an iris comprising a non-regular polygon.
Figure 4:
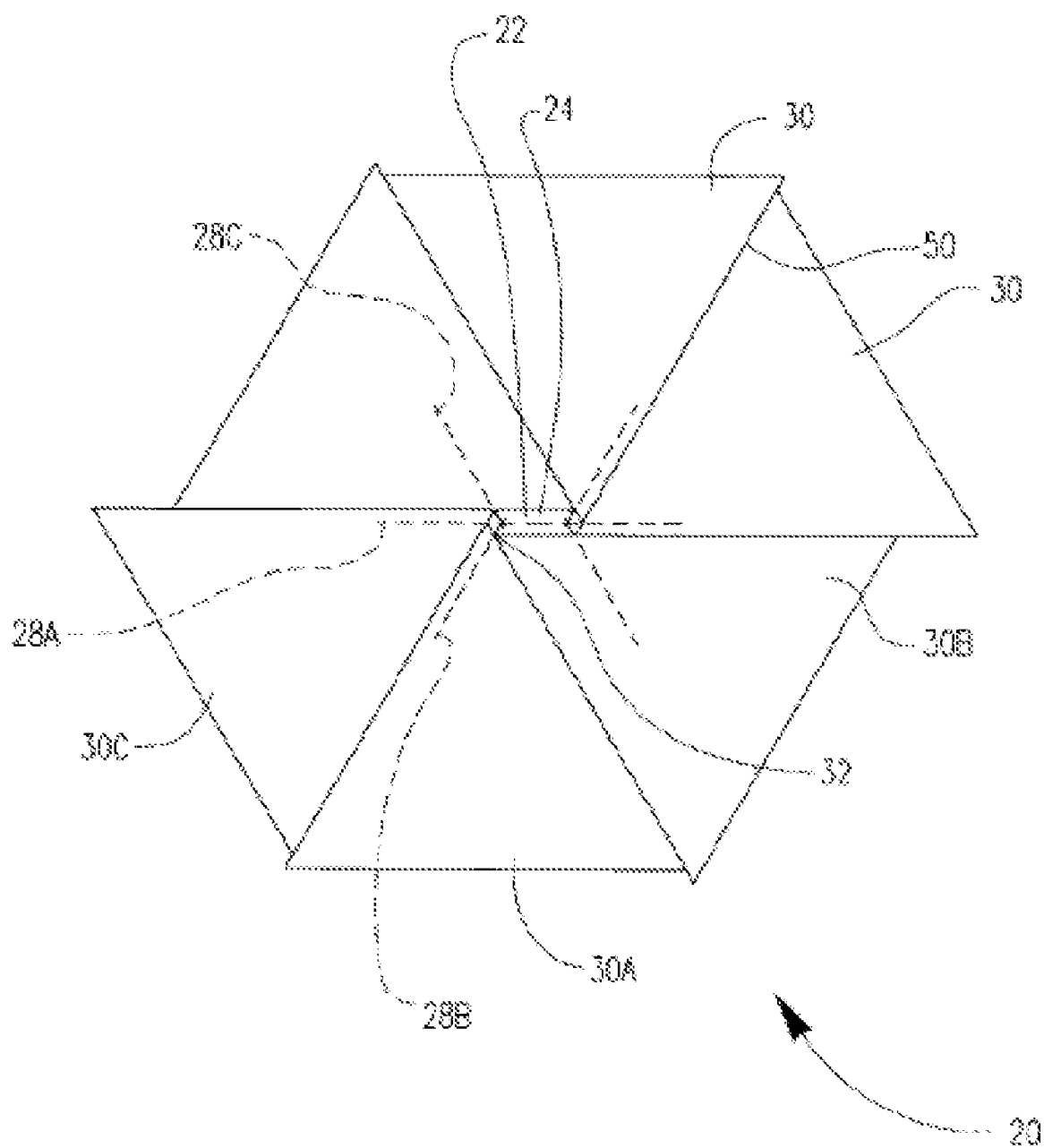
FIG. 4 is an end view of the apparatus of FIG. 3 in a more reduced state.

In another embodiment, the invention comprises an apparatus for shaping an article as shown in FIGS. 3 and 4. The apparatus 20 may comprise a plurality of movable dies 30. All of the dies 30 may have the same physical shape. Each die 30 may be adjacent to at least one other die 30a, 30b, etc. Adjacent dies 30 may be slidably engaged with one another along an area of engagement or engagement plane 50. For example, referring to FIG. 3, die 30a may be slidably engaged with a first adjacent die 30b along a first engagement plane 50ab, and may be slidably engaged with a second adjacent die 30c along a second engagement plane 50ac, etc. The dies 30 may be arranged to form a chamber 22 that may run the axial length of the device. As the dies 30 move and the size of the chamber 22 is varied, the various engagement planes 50 between various adjacent dies 30 may shift position according to the location of the dies 30.

Each die 30 may include an edge 32 and at least one wall surface or contacting surface 34 which may bound the chamber 22. A contacting surface 34 may contact and reduce the size of an article placed within the chamber 22, or contact the article to restrict expansion of the article. Contacting surfaces 34 which bound the chamber 22 may comprise an iris 24. Desirably, the dies 30 may be moved such that the iris 24 comprises a nonregular polygon, or a polygon wherein at least one side is of a different length than another side. The exact shape of the iris 24 is dependent upon the shape, arrangement and number of contacting surfaces 34 included in the apparatus 20. Each edge 32 may move along a movement path plane 28, such as movement path planes 28a, 28b, 28c, 28d and 28e depicted in FIG. 3. For example, the edge 32 of die 30c may move along movement path plane 28c.

It should be understood that although FIGS. 3 and 4 depict end views of the apparatus 20, each edge 32, contacting surface 34 and movement path plane 28 may extend along the length of the apparatus 20.

An intersection of movement path planes 28 may comprise a zero point 26 or a line comprised of zero points 26, wherein a plurality of die edges 32 may meet when the iris 24 is fully contracted. An iris 24 in the shape of a nonregular polygon may have one or more zero points 26. For example, as shown in FIG. 3, an iris 24 may have two zero points 26.

In some embodiments, the apparatus 20 may have an even number of dies 30. Dies 30 that have contacting surfaces 34 opposite one another across the iris 24 may have edges 32 that move along a common movement path plane 28. For example, movement path plane 28a in FIG. 3 comprises a movement path plane for two dies.

Dies 30 that have contacting surfaces 34 opposite one another across the iris 24 may also have edges 32 that move along separate movement path planes 28. Thus, a die edge 32 may have a movement path plane 28 that is independent from all other movement path planes 28. For example, in FIG. 3, the edge 32 of die 30d moves along movement path plane 28d. No other edge 32 shares movement path plane 28d. Desirably, the movement path planes 28 of dies 30 that are opposite one another across the iris 24 may be parallel, such as movement path plane 28d is parallel to movement path plane 28b.

Desirably, a movement path plane 28 of a first die tip 32 may be parallel to an engagement plane 50 between two other dies 30. For example, the edge 32 of die 30b may move along movement path plane 28b, which may be parallel to the engagement plane 50ac between die 30a and die 30c.

Desirably, angles formed between movement path planes 28 at a zero point 26 may all be similar. Angles formed between movement path planes 28 that intersect at a first zero point 26 may be similar to the angles formed between movement path planes 28 that intersect at a second zero point 26. For example, the angle formed between engagement planes 28b and 28c may be the same as the angle formed between engagement planes 28a and 28b, which may also be the same as the angle formed between engagement planes 28d and 28e.

Desirably, all of the dies 30 may be moved simultaneously such that each edge 32 may be the same predetermined distance away from its zero point line 26 as all other edges 32 are away from their respective zero point lines 26 at any given time.

FIG. 4 shows the apparatus 20 of FIG. 3 with the iris 24 in a more reduced configuration. The embodiment of FIGS. 3 and 4 is suited to reduce an article, such as a stent, that may be placed within the chamber 22. The article may be reduced to have a substantially oval cross-sectional shape.

Figure 5:
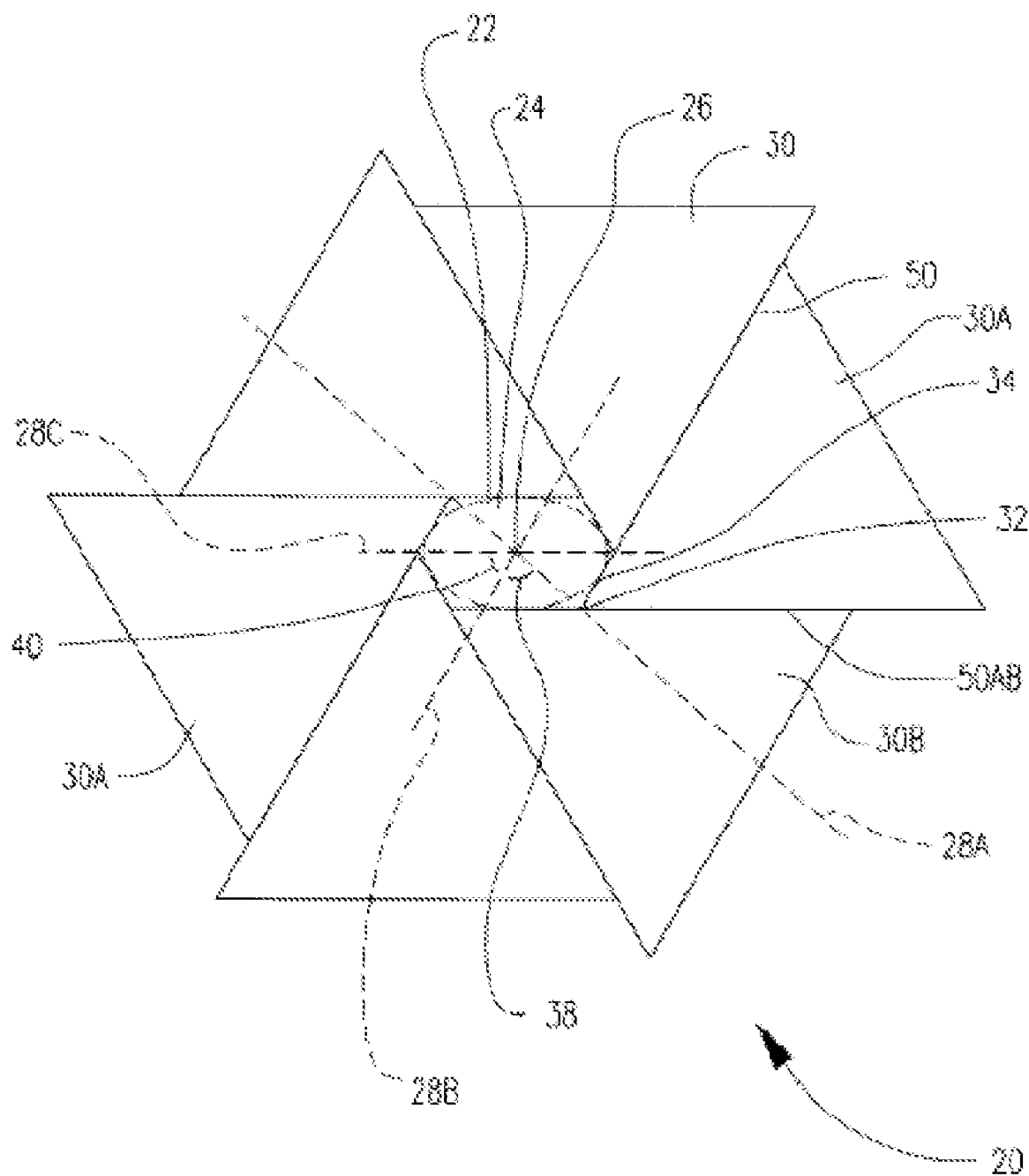
FIG. 5 is an end view of an apparatus for reducing the size of an article having an iris comprising a non-regular polygon.

In another embodiment, the invention comprises an apparatus for shaping an article as shown in FIG. 5. The apparatus 20 may comprise a plurality of movable dies 30. All of the dies 30 may have the same physical shape. Each die 30 may be adjacent to at least one other die 30. Adjacent dies 30 may be slidably engaged with one another along an engagement plane 50. Referring to FIG. 5, a die 30A may be slidably engaged with an adjacent die 30B along an engagement plane 50AB.

The dies 30 of the apparatus 20 may be arranged to form a chamber 22 that may run the length of the device. Wall surfaces or contacting surfaces 34 which bound the chamber 22 may comprise an iris 24. Desirably, the dies 30 may be moved such that the iris 24 comprises a nonregular polygon, or a polygon wherein at least one side is of a different length than another side.

Each die 30 may include an edge 32 and at least one contacting surface 34. The contacting surface 34 may contact and reduce the size of an article placed within the chamber 22. The exact shape of the iris 24 is dependent upon the shape, arrangement and number of contacting surfaces 34 included in the apparatus 20. Each edge 32 may move along a movement path plane 28, such as movement path planes 28A, 28B and 28C depicted in FIG. 3. For example, the edges 32 of dies 30A may move along movement path plane 28A. All of the movement path planes 28 may intersect at a zero point line 26. All of the edges 32 of the dies 30 may meet at the zero point line 26 when the chamber 22 is fully contracted.

Typically there will be an even number of dies 30. Dies 30 that are opposite one another across the iris 24 may have tips 32 that move along a common movement path line 28.

Desirably, a first angle 38 may be formed between a first movement path plane 28 and a second movement path plane 28, and a second angle 40 may be formed between the second movement path plane 28 and a third movement path plane 28. The first angle 38 may be different than the second angle 40. For example, the first angle 38 may be larger than the second angle 40.

At least one movement path plane 28 may be parallel to at least one engagement plane 50. For example, movement path plane 28c is parallel to engagement plane 50AB. At least one movement path plane 28 may be nonparallel to any engagement planes.

Desirably, all of the dies 30 may be moved simultaneously such that each edge 32 may be equidistant from the zero point line 26 while moving along its respective movement path plane 28. The angular relationship between the movement path planes 28 may be selected to determine the shape of the iris 24. For example, as shown in FIG. 5, the apparatus 20 may be able to reduce an article such as a stent in size, and to impart a non-circular cross-section to the stent, such as an ovular cross-section.

Figure 6:
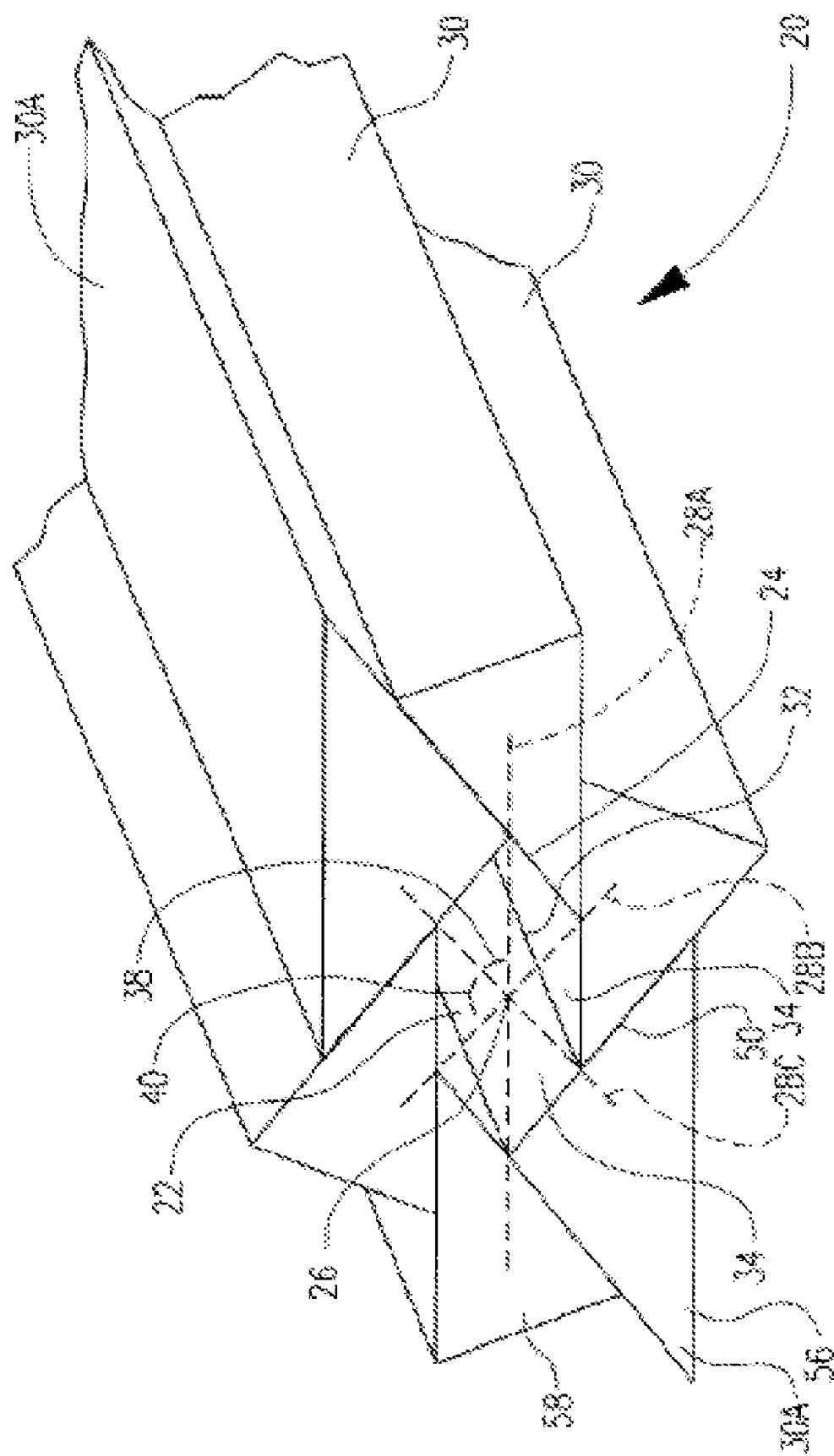
FIG. 6 is an isometric view of an apparatus for reducing the size of an article having an iris comprising a non-regular polygon.
Figure 7:
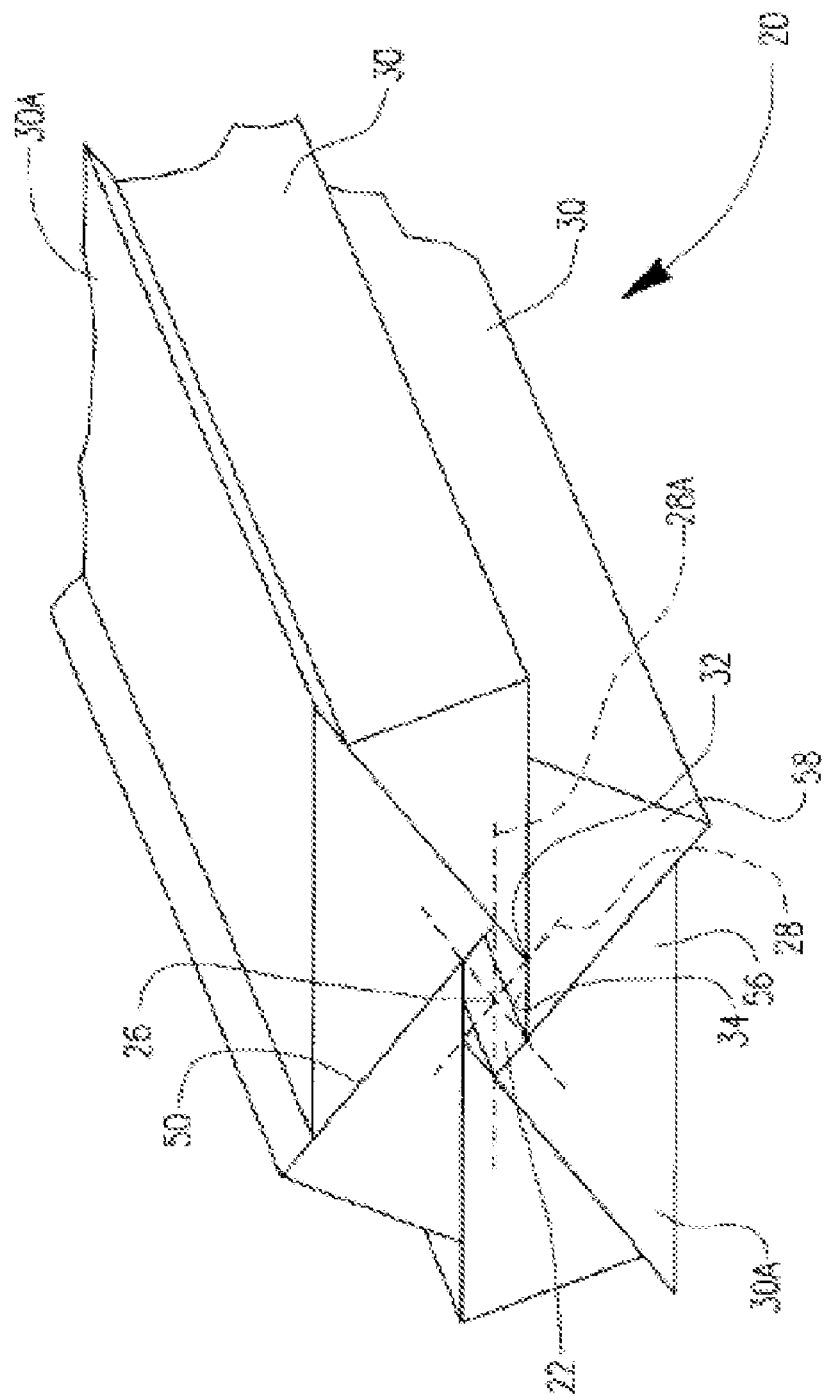
FIG. 7 is an isometric view of an apparatus for reducing the size of an article having an iris comprising a non-regular polygon in a more reduced state than that of FIG. 6.
Figure 8:
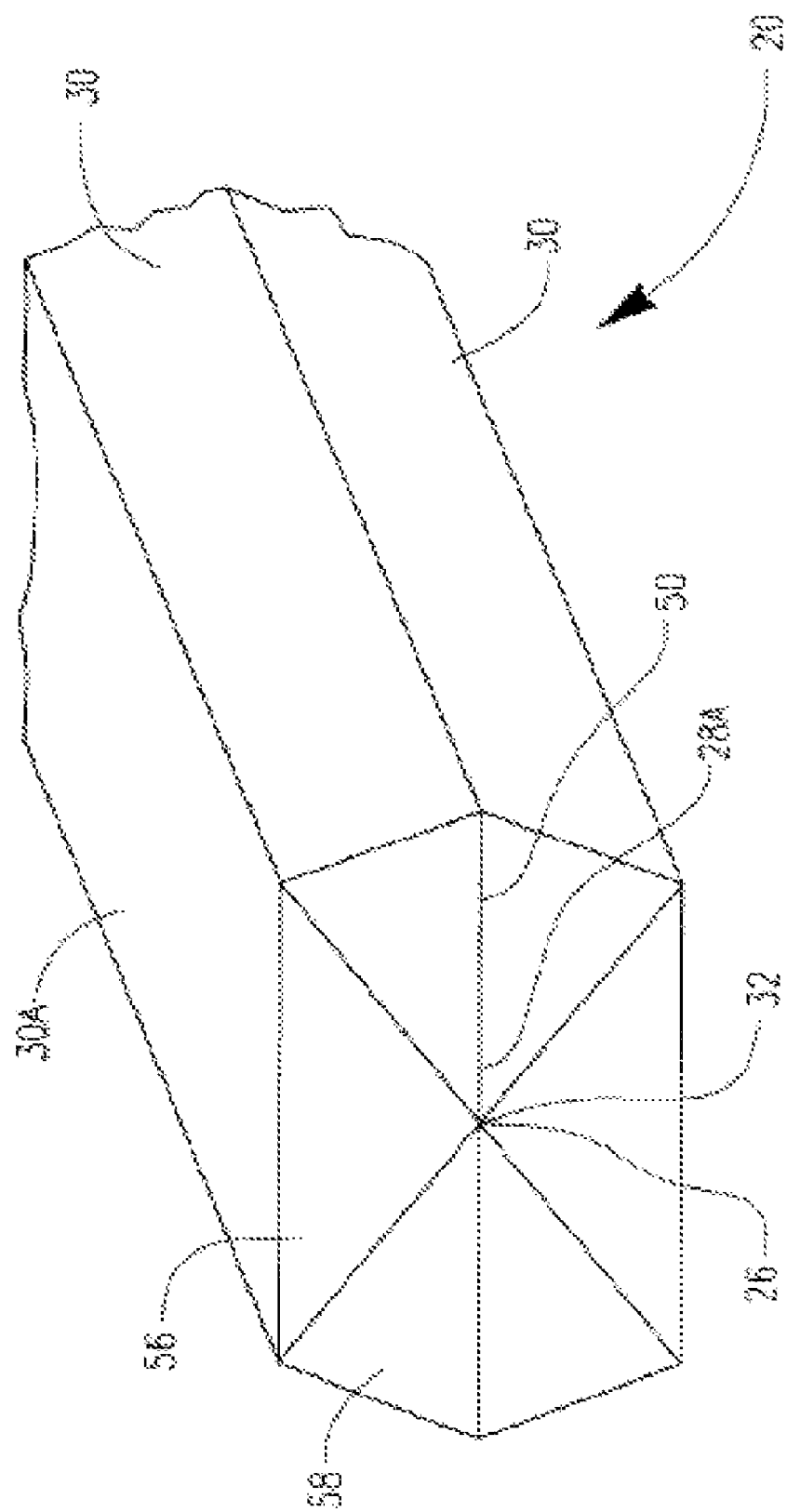
FIG. 8 is an isometric view of an apparatus for reducing the size of an article having an iris comprising a non-regular polygon in a more reduced state than that of FIG. 7.

FIGS. 6-8 show another embodiment of an apparatus 20, which may comprise a plurality of movable dies 30. Dies 30 may include a first shape 56 and a second shape 58. Each die 30 may be adjacent to at least one other die 30. Adjacent dies 30 may be slidably engaged with one another along an engagement plane 50. The dies 30 may be arranged to form a chamber 22 that may run the length of the device. Wall surfaces or contacting surfaces 34 which bound the chamber 22 may comprise an iris 24. The iris 24 may comprise a nonregular polygon, or a polygon wherein at least one side is of a different length than another side.

Each die 30 may include an edge 32 and at least one contacting surface 34. A contacting surface 34 may contact and reduce the size of an article placed within the chamber 22. The exact shape of the iris 24 is dependent upon the shape, arrangement and number of contacting surfaces 34 included in the apparatus 20. Each edge 32 may move along a movement path plane 28, such as movement path planes 28A, 28B and 28C as shown in FIG. 6. For example, the edge 32 of die 30A may move along movement path plane 28A. Movement path planes 28 may intersect at a zero point line 26, wherein a plurality of die edges 32 meet when the chamber 22 is fully reduced.

The apparatus 20 may optionally have an even number of dies 30. Dies 30 that have contacting surfaces 34 opposite one another across the iris 24 may comprise a pair. Dies 30 that comprise a pair may have a similar shape, and may have edges 32 that move along a common movement path plane 28. For example, dies 30A of FIG. 6 comprise a pair. Dies 30A have contacting surfaces 34 that are opposite one another across the iris 24, each comprise a first shape 56, and share a common movement path plane 28A.

Desirably, each movement path plane 28 may be parallel to at least one engagement plane 50 between two dies 30. Desirably, a first angle 38 may be formed between a first movement path plane 28A and a second movement path plane 28C, and a second angle 40 may be formed between the second movement path plane 28C and a third movement path plane 28B. The first angle 38 may be different than the second angle 40. For example, the first angle 38 may be smaller than the second angle 40.

Desirably, all of the dies 30 may be moved simultaneously such that each edge 32 may be equidistant from the zero point line 26 along its respective movement path plane 28. The angular relationship between the movement path planes 28 may be selected to determine the shape of the iris 24. For example, as shown in FIG. 6, the apparatus 20 may be able to reduce an article such as a stent in size, and to impart a non-circular cross-section to the stent, such as an ovular cross-section.

FIG. 7 shows the apparatus 20 of FIG. 6 with the chamber 22 in a more reduced configuration. FIG. 8 shows the apparatus of FIGS. 6 and 7 in a fully reduced configuration, wherein all die edges 32 have met at a zero point line 26, the size of the chamber 22 has been reduced to a minimum.

Figure 9:
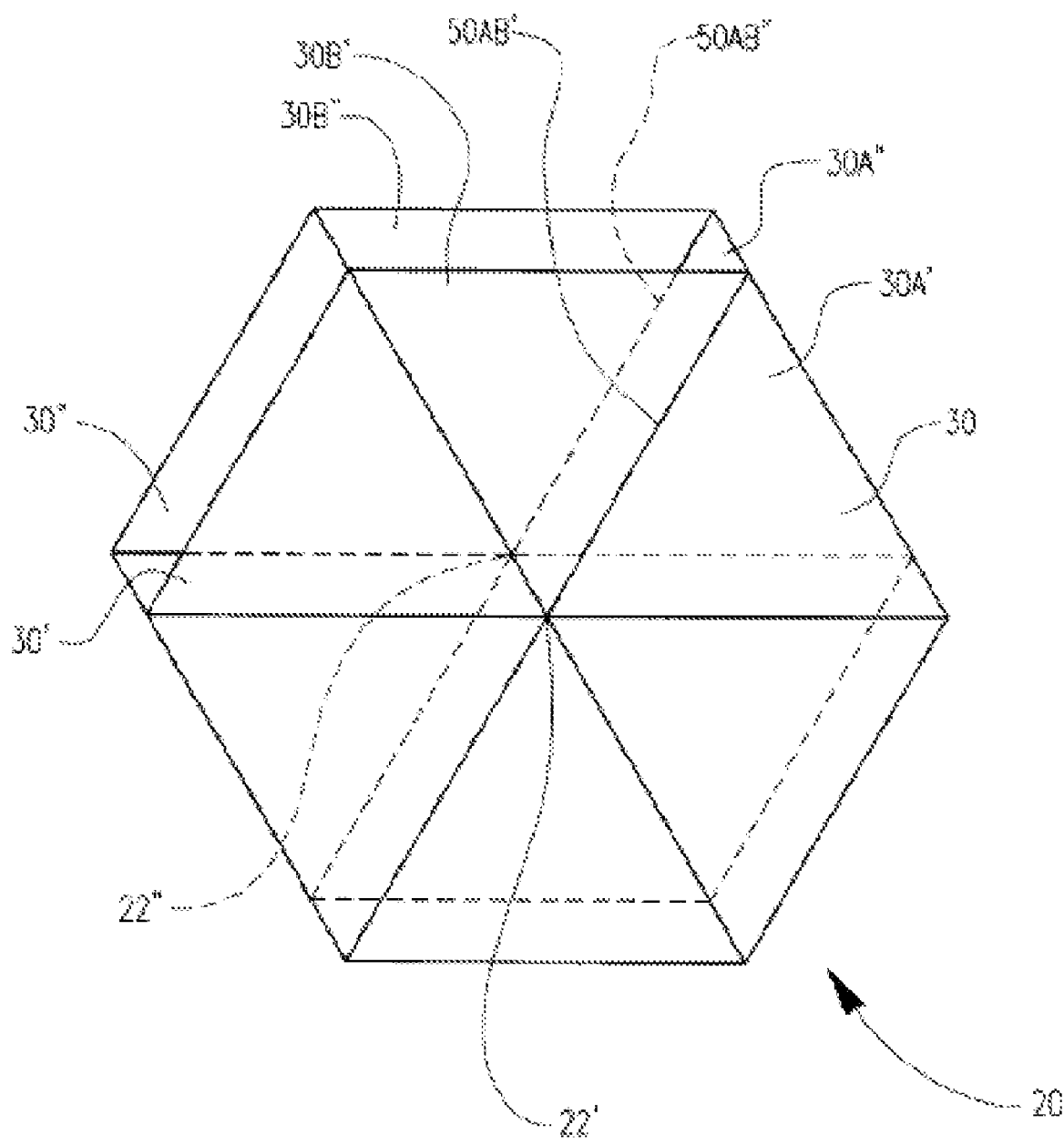
FIG. 9 is an end view of an apparatus for reducing the size of an article having a first portion of a chamber offset from a second portion of a chamber.
Figure 10:
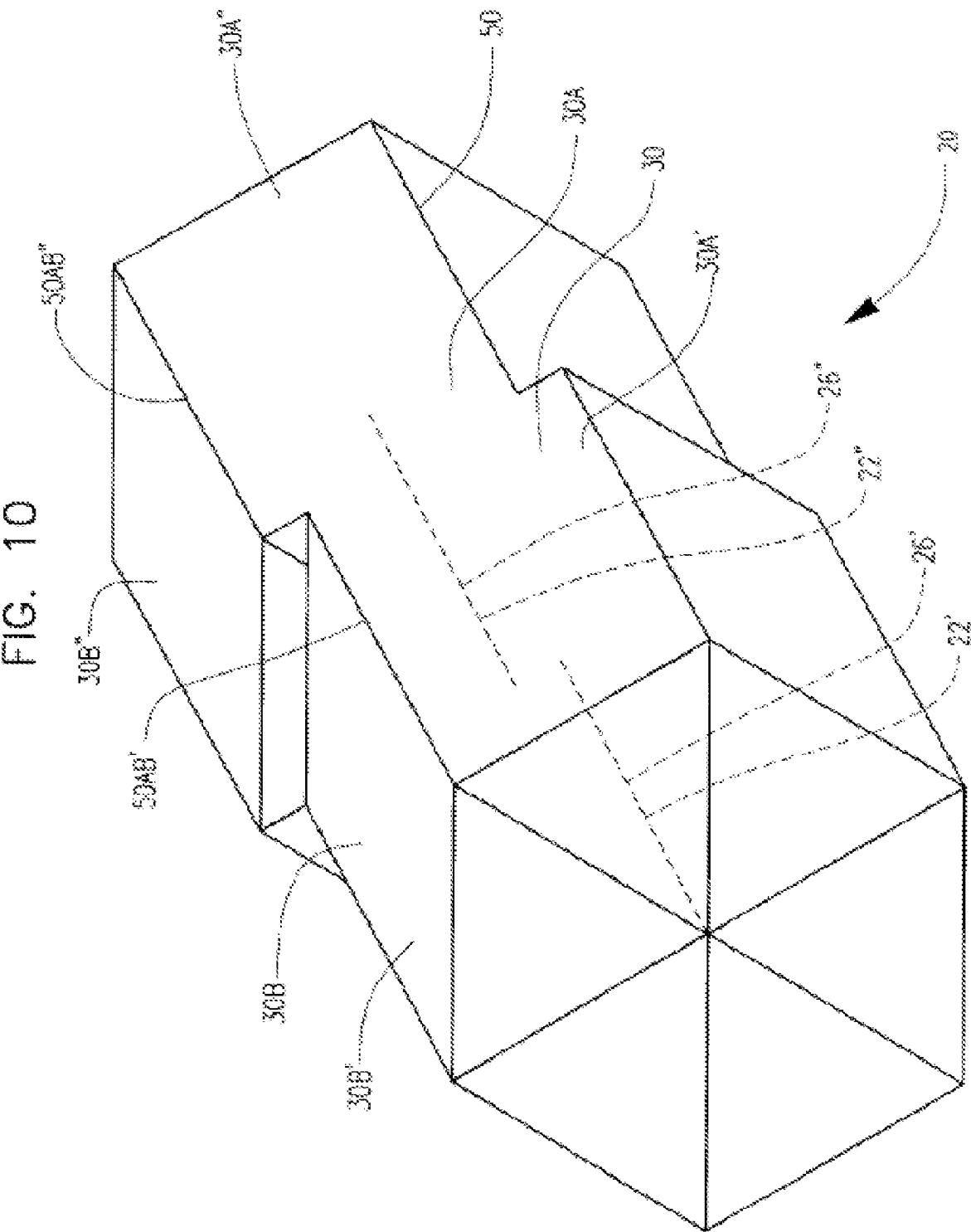
FIG. 10 is an isometric view of an apparatus for reducing the size of an article having a first portion of a chamber offset from a second portion of a chamber.

FIGS. 9 and 10 show an embodiment of an apparatus 20 for shaping an article having a first portion having a first chamber and a second portion having a second chamber, the longitudinal axis or zero point line 26' of the first chamber being offset from the longitudinal axis or zero point line 26" of the second chamber. The longitudinal axis of the first chamber may be parallel to the longitudinal axis of the second chamber.

The apparatus 20 may be formed from a plurality of dies 30. Each die 30 may have a first portion 30' and a second portion 30". The first portion 30' and second portion 30" of each die 30 may be similar to one another; however, the second portion 30" is generally offset from the first portion 30' by a predetermined amount.

Each die 30 may be adjacent to at least one other die 30. Adjacent dies 30 may be slidably engaged with one another along at least one engagement plane 50. Each first portion 30' of a die 30 may be slidably engaged along an engagement plane 50 with the first portion 30' of an adjacent die 30. Each second portion 30" of a die 30 may be slidably engaged along an engagement plane 50 with the second portion 30" of an adjacent die 30. For example, FIG. 10 shows adjacent dies 30A and 30B. First portions 30A' and 30B' may be slidably engaged with one another along engagement plane 50AB'. Second portions 30A" and 30B" may be slidably engaged with one another along engagement plane 50AB".

Desirably, all engagement planes 50 shared between two adjacent dies 30 may be parallel to one another. Thus, engagement plane 50AB' between dies 30A and 30B may be parallel to engagement plane 50AB".

The dies 30 of the apparatus 20 may be arranged such that the first portions 30' of the dies 30 form a first chamber 22' (see FIG. 14) and the second portions 30" of the dies 30 form a second chamber 22". Wall surfaces or contacting surfaces 34 which bound either chamber 22, 22' may comprise an iris 24. The iris 24 of the first chamber 22' may be the same shape as the iris 24 of the second chamber 22".

Figure 11:
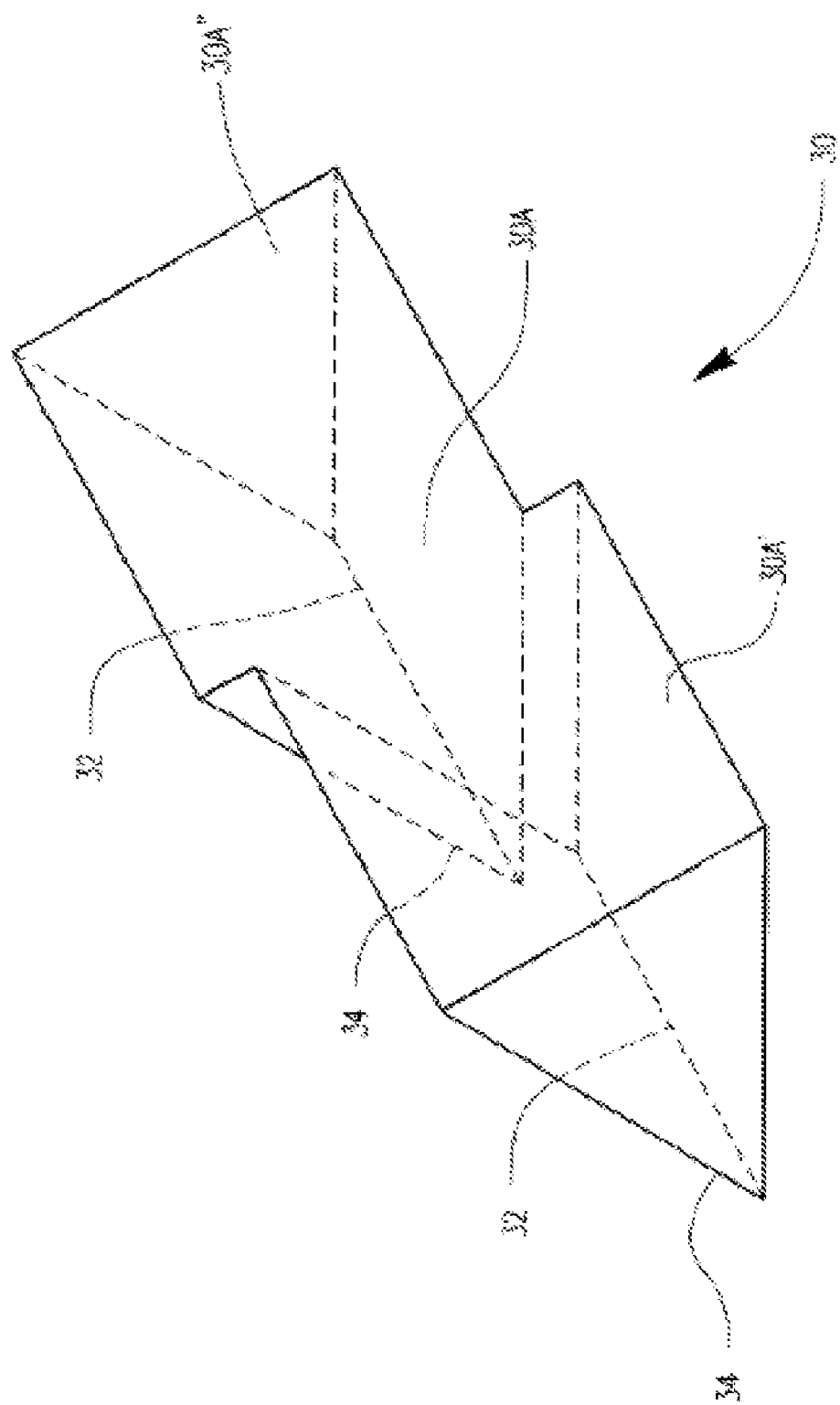
FIG. 11 shows an inventive die.
Figure 12:
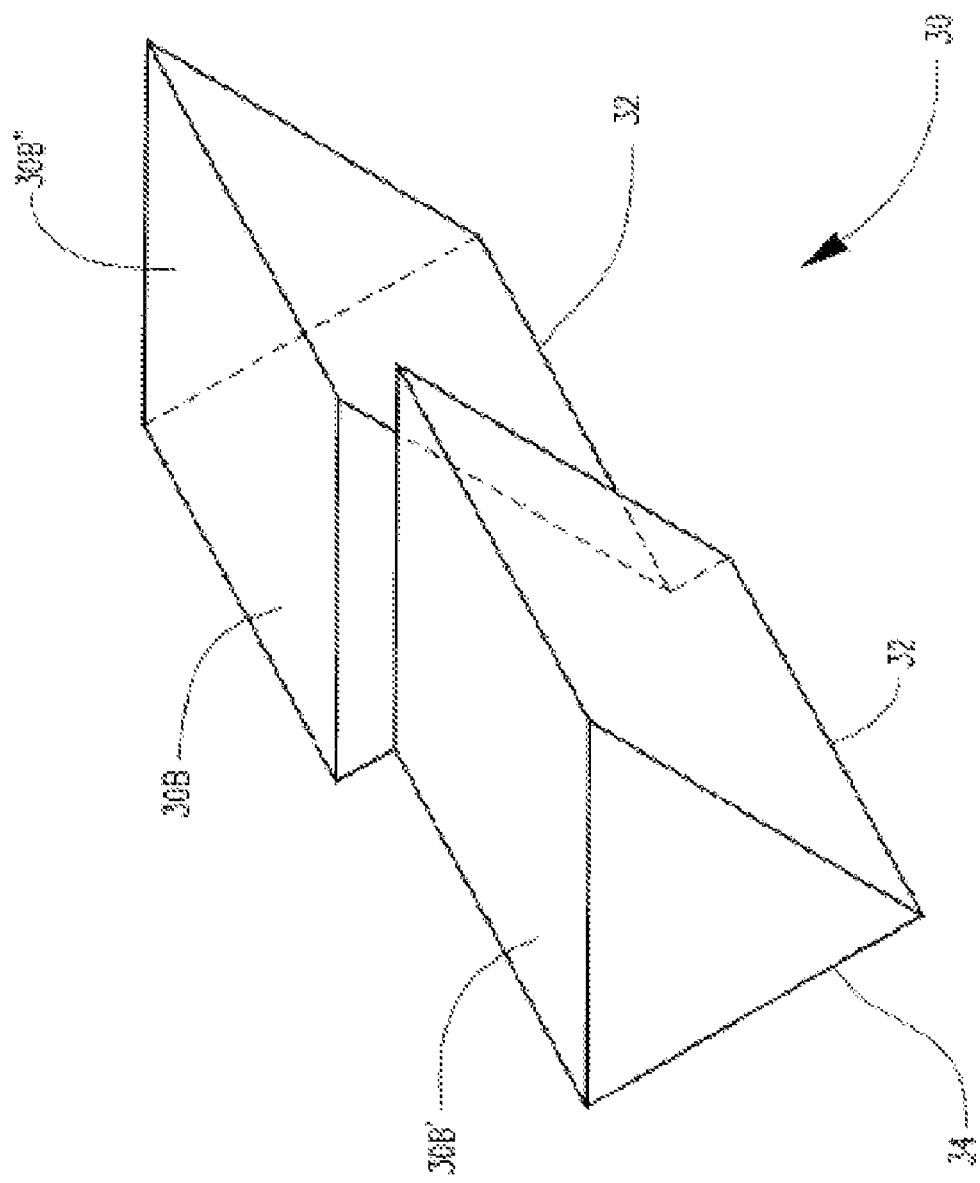
FIG. 12 shows another inventive die.

FIG. 11 shows a view of die 30A and FIG. 12 shows a view of die 30B as depicted in FIG. 10.

Each portion 30', 30" of a die 30 may include an edge 32 and at least one contacting surface 34. The contacting surface 34 may contact and reduce the size of an article placed within the chamber 22. The exact shape of the iris 24 is dependent upon the shape, arrangement and number of contacting surfaces 34 included in the apparatus 20.

Figure 13:
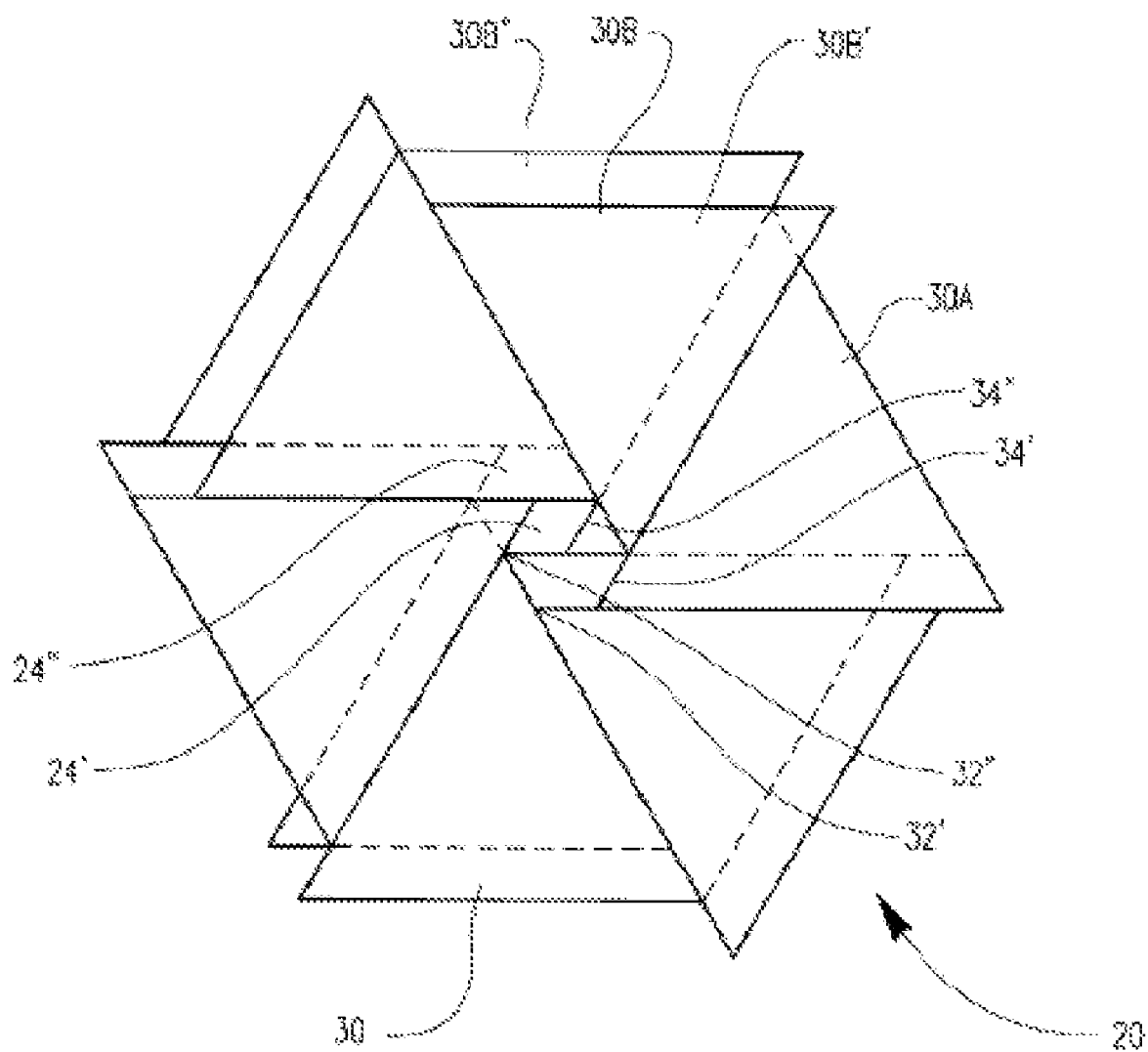
FIG. 13 is an end view of an apparatus for reducing the size of an article having a first portion of a chamber offset from a second portion of a chamber in a more open configuration than shown in FIG. 9.
Figure 14:
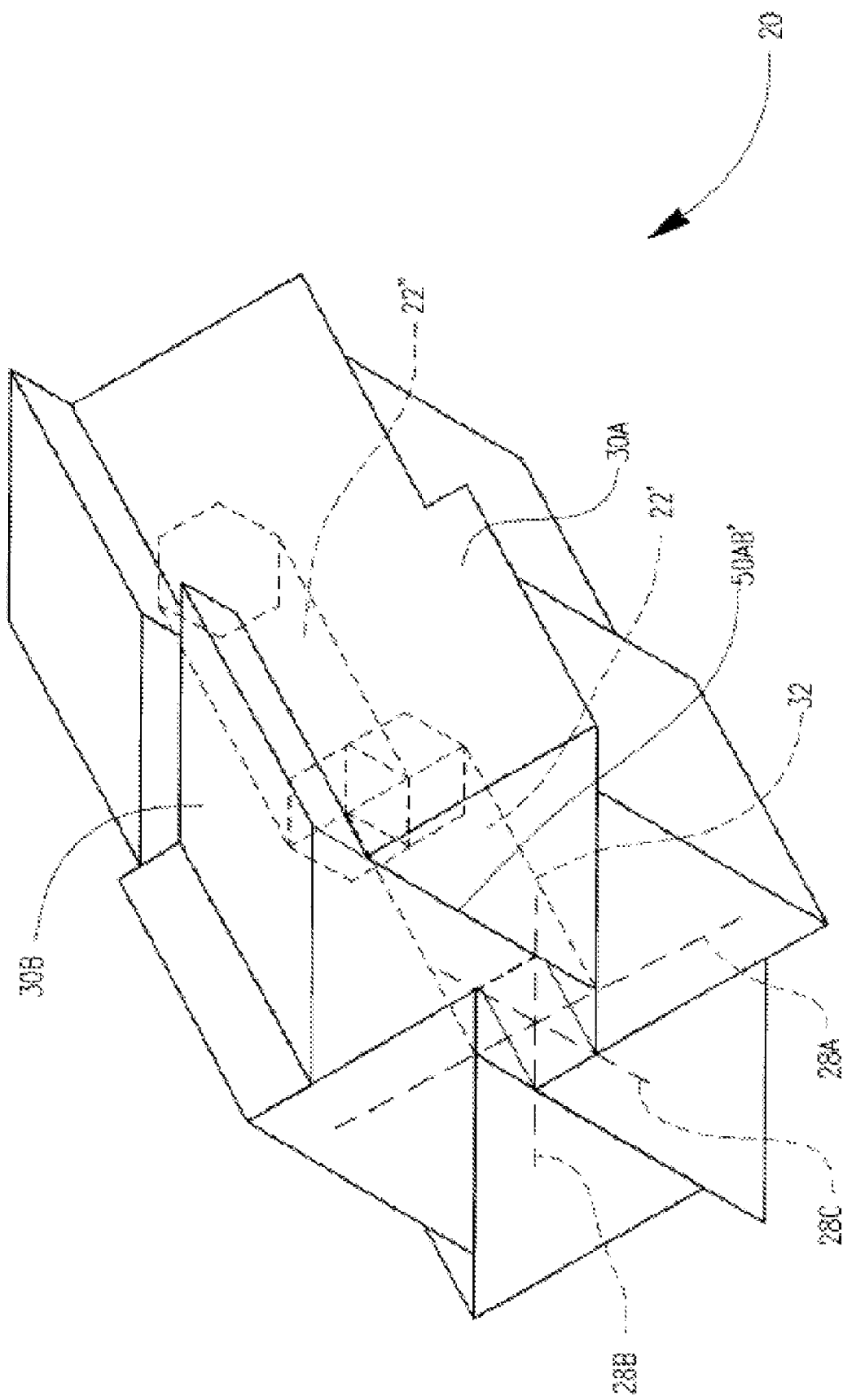
FIG. 14 is an isometric view of an apparatus for reducing the size of an article having a first portion of a chamber offset from a second portion of a chamber in a more open configuration than shown in FIG. 10.

FIGS. 13 and 14 show the embodiment of the apparatus 20 of FIGS. 9 and 10 arranged with the chambers in a more open state. The chamber 22 of the first portion of the apparatus 20 may have a cross-section or iris 24 that is shaped substantially similar to the iris 24 of the chamber of the second portion.

As shown in FIG. 13, the edge 32 of each portion 30', 30" of each die 30 may move along a movement path plane 28, such as movement path planes 28A, 28B and 28C. For example, an edge 32 of the first portion 30' of die 30A may move along movement path plane 28A. All of the movement path planes 28 may intersect at a zero point line 26 (as shown in FIG. 10). A zero point line 26 may comprise the central longitudinal axis of a chamber 22. All of the edges 32 of the first portion 30' or the second portion 30" of the dies 30 may meet at a respective zero point line 26 when the respective chamber 22 is fully contracted.

Generally, there may be an even number of dies 30. Dies 30 that are opposite one another across the iris 24 may have edges 32 that move along a common movement path plane 28.

Desirably, angles formed between movement path planes 28 at a zero point line 26 may all be similar.

At least one movement path plane 28 may be parallel to at least one engagement plane 50. For example, movement path plane 28C is parallel to engagement plane 50AB'.

Desirably, all of the dies 30 may be moved simultaneously such that each edge 32 may be equidistant from its zero point line 26 along its respective movement path plane 28.

As shown in FIGS. 13 and 14, the iris 24 formed by wall surfaces bounding the chamber 22 may comprise a regular polygon. In other embodiments, the iris 24 of each chamber 22 may comprise a nonregular polygon. For example, an apparatus having a first chamber offset from a second chamber, wherein the cross-section of each chamber comprises a nonregular polygon, may be formed by shaping portions 30', 30" of the dies 30 similarly to the dies shown in FIGS. 6-8.

In another embodiment, an apparatus shaped similarly to the apparatus of FIGS. 9-14 may be formed from two sets of dies. The first set of dies may be arranged to form the first chamber 22', and the second set of dies may be arranged to form the second chamber 22". When independent sets of dies are used to form each chamber, the size of the first chamber 22' may be adjusted independently from the size of the second chamber 22".

Figure 15:
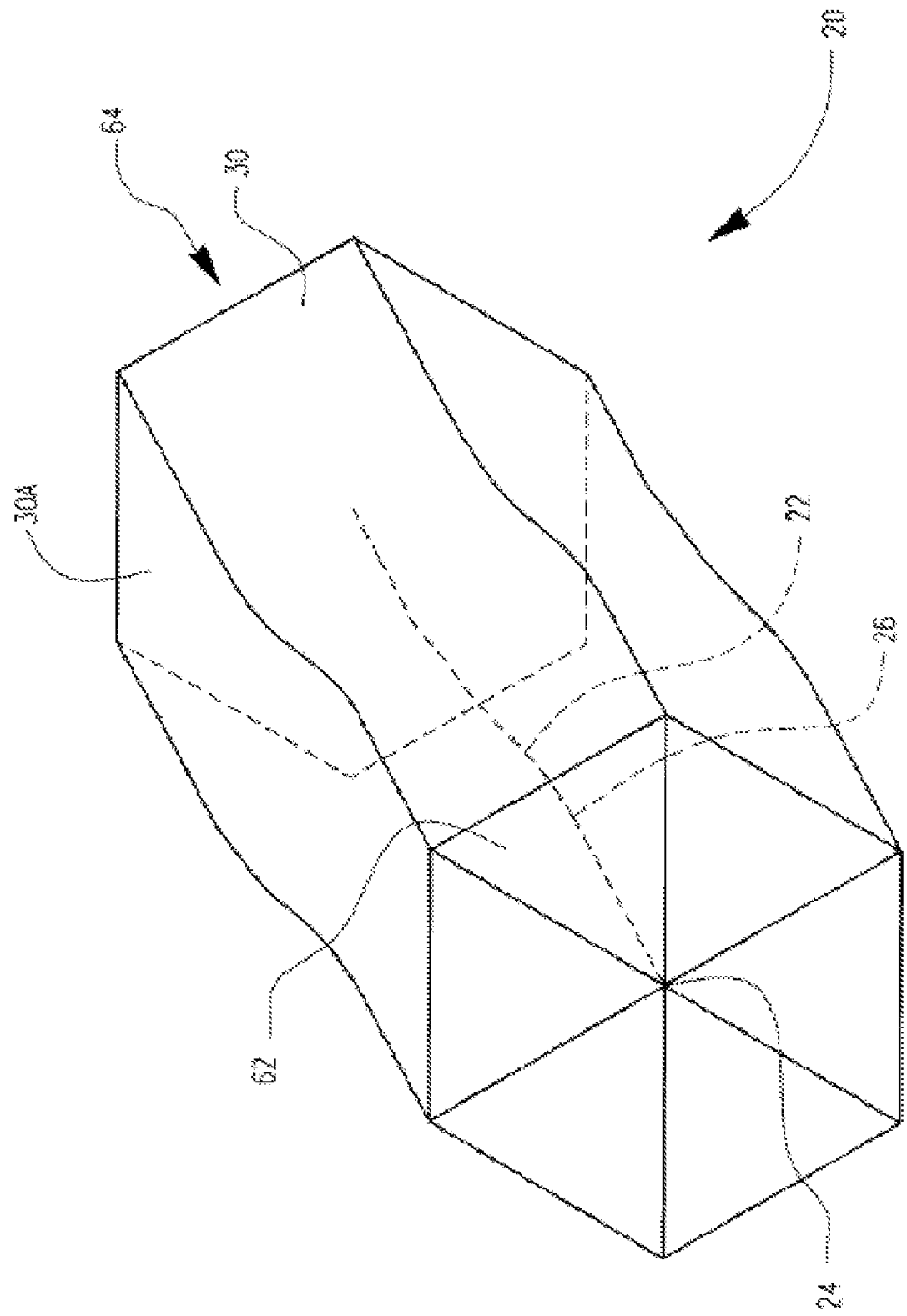
FIG. 15 is an isometric view of an apparatus for reducing the size of an article having chamber with curvature.
Figure 16:
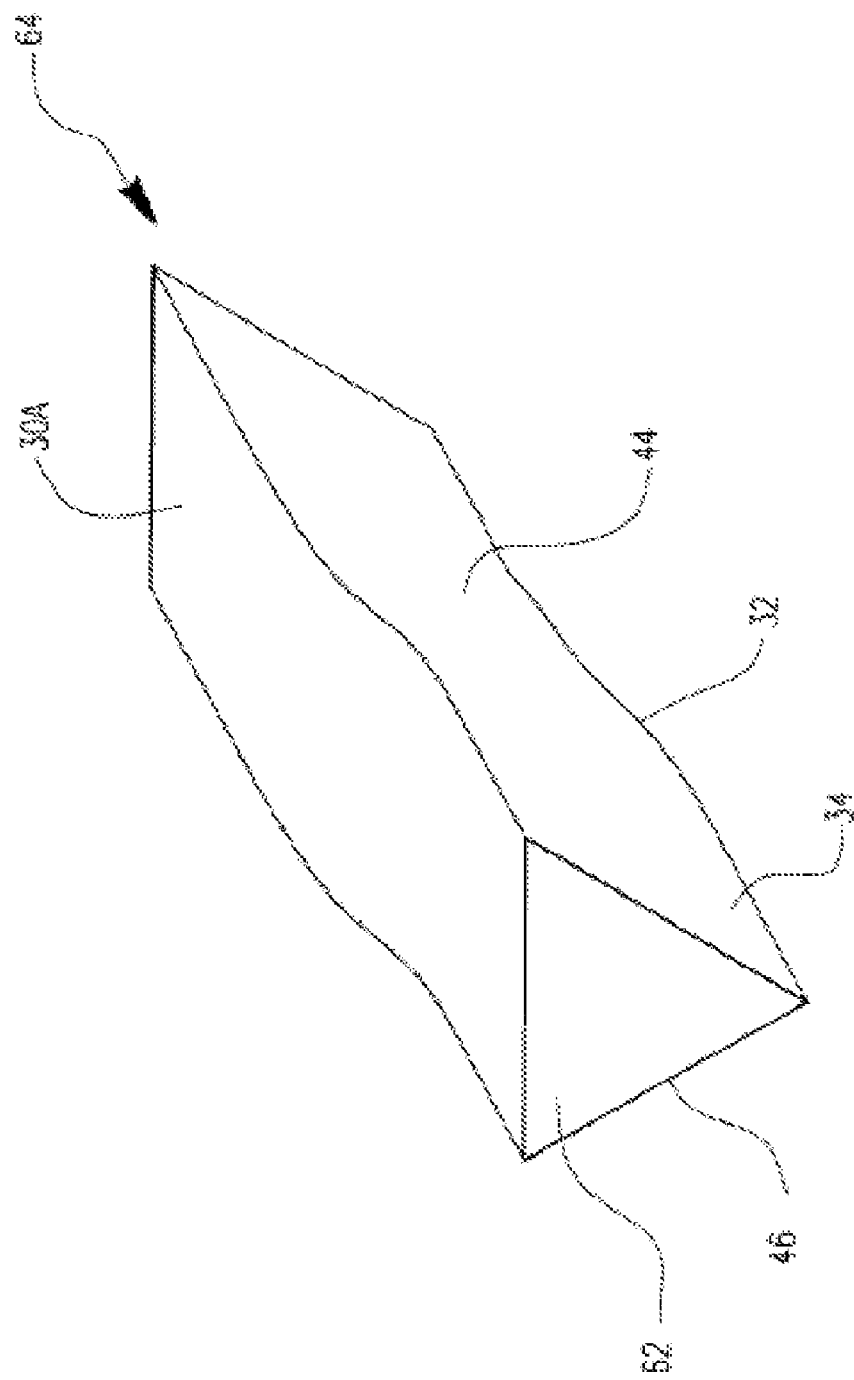
FIG. 16 shows an inventive die.
Figure 17:
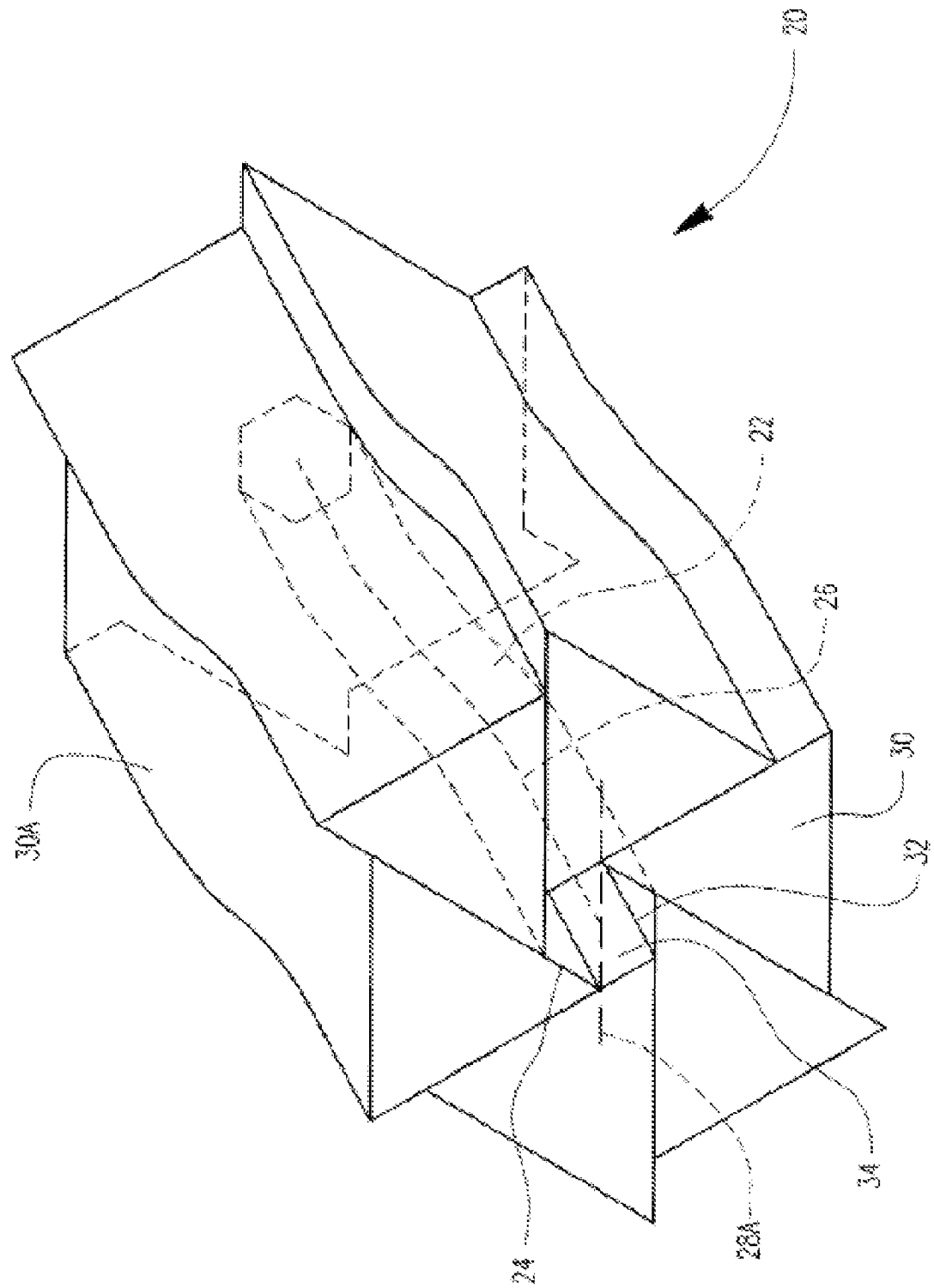
FIG. 17 is an isometric view of an apparatus for reducing the size of an article having chamber with curvature in a more open configuration than shown in FIG. 15.

FIGS. 15-17 show another embodiment of the invention having a chamber 22 (see FIG. 17) with curvature. An apparatus 20 for shaping an article may comprise a plurality of movable dies 30. Each die 30 may be adjacent to at least one other die 30. The dies 30 may be arranged to form a chamber 22 that may run the length of the device. Wall surfaces or contacting surfaces 34 which bound the chamber 22 may comprise an iris 24.

FIG. 16 shows die 30A from FIG. 15. Each die 30 may include an edge 32 and at least a first side 44 and a second side 46. A first side 44 may comprise a contacting surface 34. A contacting surface 34 may contact and reduce the size of an article placed within the chamber 22 formed by the plurality of dies 30. A contacting surface 34 may have a non-uniform curvature along its length or in the longitudinal direction of the chamber. The curvature of a contacting surface 24 may impart curvature to the chamber 22.

Adjacent dies 30 may be slidably engaged with one another. Generally, the first side 44 of a die 30 may be slidably engaged with a second side 46 of an adjacent die 30. The first side 44 of a die 30 may have a non-uniform curvature along its length. Thus, the second side 46 of an adjacent die 30 may have a non-uniform curvature along its length that is complimentary to the first side 44 of the first die 30.

The edge 32 of each die 30 may travel along a movement path 28, such as movement path 28A shown in FIG. 17. Dies 30 that are opposite one another across the iris 24 may have edges 32 that share a common movement path 28. The dies 30 may move uniformly relative to one another such that the size of the iris 24 may be reduced until all of the edges 32 meet at a zero point line 26. Generally, a zero point 26 comprises the center of an iris 24. Thus, some or all of the movement paths 28 may intersect at the zero point line 26.

Desirably, all of the dies 30 may be moved simultaneously such that each edge 32 may be the same predetermined distance away from the zero point line 26 as all other edges 32 at any given time.

Various cross-sections of the apparatus 20 may be offset from one another along the length of the apparatus 20, but the shape of the cross-section is desirably constant. The embodiment shown in FIGS. 15-17 may be better understood by comparing it to the embodiment shown FIG. 10. Each die 30 may have a first end 62 and a second end 64 as shown in FIGS. 15 and 16. The first end 62 of a given die 30 in FIG. 15 may correspond to the first end of a similarly placed die in FIG. 10. The second end 64 of the die 30 in FIG. 15 may correspond to the second end of the similarly placed die in FIG. 10. However, instead of having an abrupt offset in the edge 32 of the die as shown in the embodiment of FIG. 10, the edge 32 gradually and continuously curves. The sliding engagement between adjacent dies 30 is similar to the sliding engagement between adjacent dies in FIG. 10.

FIGS. 18-21B show an embodiment of an apparatus 20 for shaping an article having a first chamber and a second chamber. The first and second chambers may be offset from one another and may be sized differently from one another.

Figure 18:
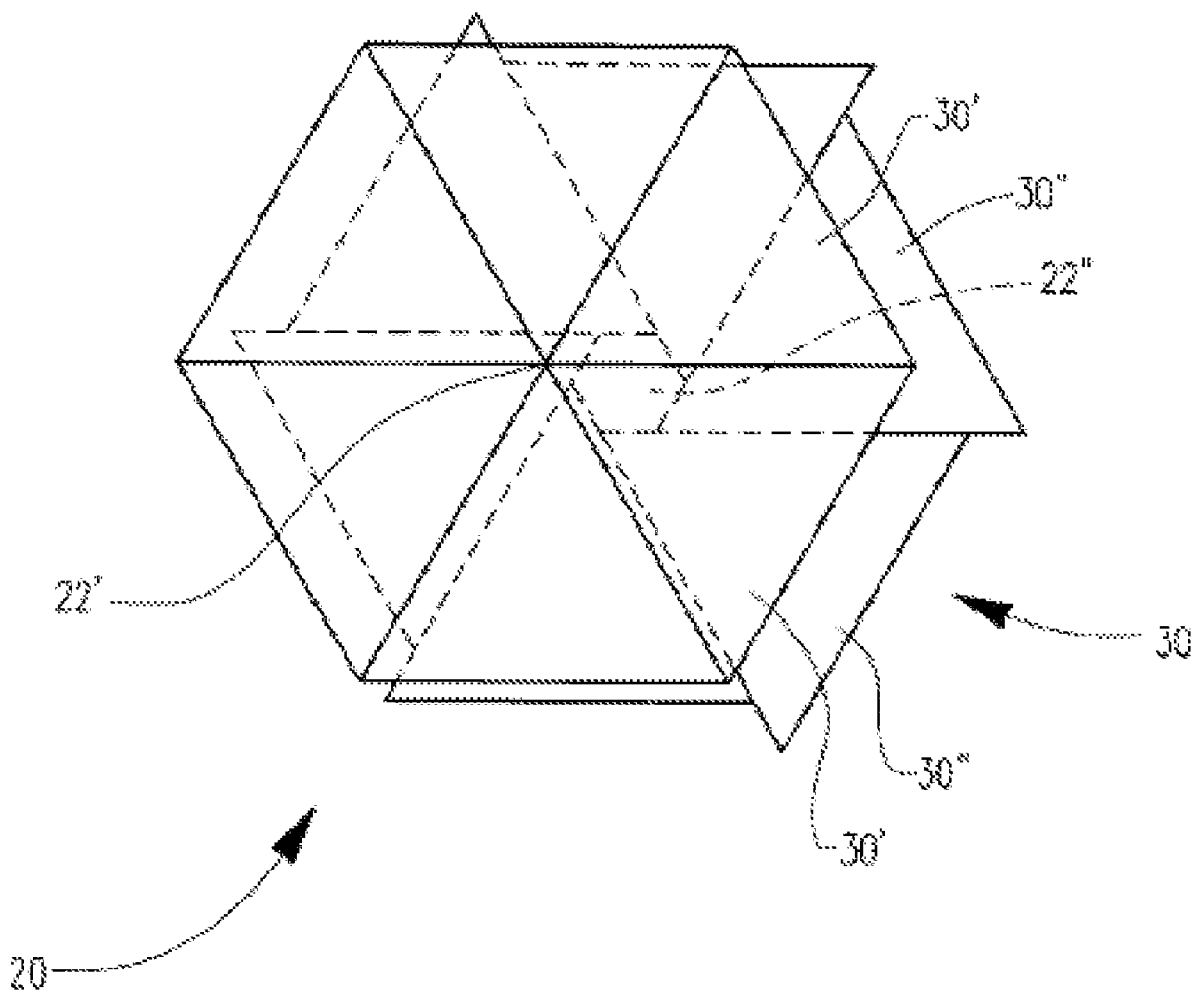
FIG. 18 is an end view of an apparatus for reducing the size of an article having a first portion of a chamber offset from a second portion of a chamber, the two portions having difference cross-sections.
Figure 19:
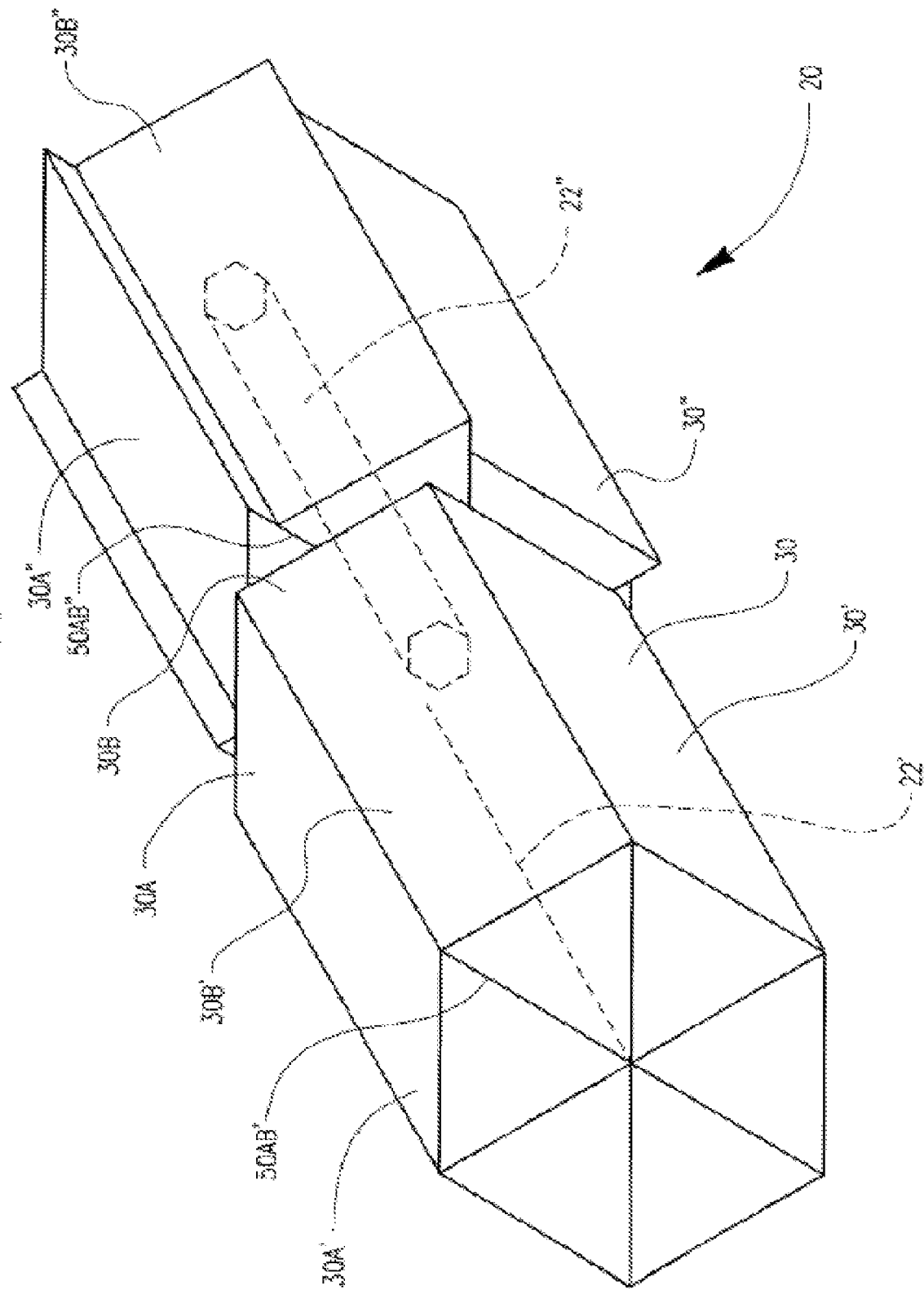
FIG. 19 is an isometric view of an apparatus for reducing the size of an article having a first portion of a chamber offset from a second portion of a chamber, the two portions having difference cross-sections.

FIGS. 18 and 19 depict the apparatus 20 in a configuration wherein one chamber is fully closed and another chamber is not closed. The apparatus 20 may be formed from a plurality of dies 30. Each die 30 may have a first portion 30' and a second portion 30". The first portion 30' and second portion 30" of each die 30 may be similar to one another; however, the second portion 30" may be laterally offset from the first portion 30' by a predetermined amount.

Each die 30 may be adjacent to at least one other die 30. Adjacent dies 30 may be slidably engaged with one another. Each first portion 30' of a die 30 may be slidably engaged along an engagement plane 50 with the first portion 30' of an adjacent die 30. Each second portion 30" of a die 30 may be slidably engaged along an engagement plane 50 with the second portion 30" of an adjacent die 30. For example, FIG. 19 shows adjacent dies 30A and 30B. First portions 30A' and 30B' may be slidably engaged with one another along engagement plane 50AB'. Second portions 30A" and 30B" may be slidably engaged with one another along engagement plane 50AB".

Desirably, all engagement planes 50 shared between two adjacent dies 30 may be parallel to one another. Thus, engagement plane 50AB' between dies 30A and 30B may be parallel to engagement plane 50AB".

The dies 30 of the apparatus 20 may be arranged such that the first portions 30' of the dies 30 form a first chamber 22' and the second portions 30" of the dies 30 form a second chamber 22". Wall surfaces or contacting surfaces 34 which bound either chamber 22, 22' may comprise an iris 24. The iris 24 of the first chamber 22' may be the same shape as the iris 24 of the second chamber 22". Desirably, the iris 24 of the second chamber 22" may have a larger area than the iris 24 of the first chamber 22'.

In a configuration wherein one chamber is closed, a first chamber 22' may be fully closed while a second chamber 22" may be partially open. Desirably, when the apparatus 20 is in a configuration wherein one chamber is closed, the closed chamber has reached a minimum size.

Figure 20:
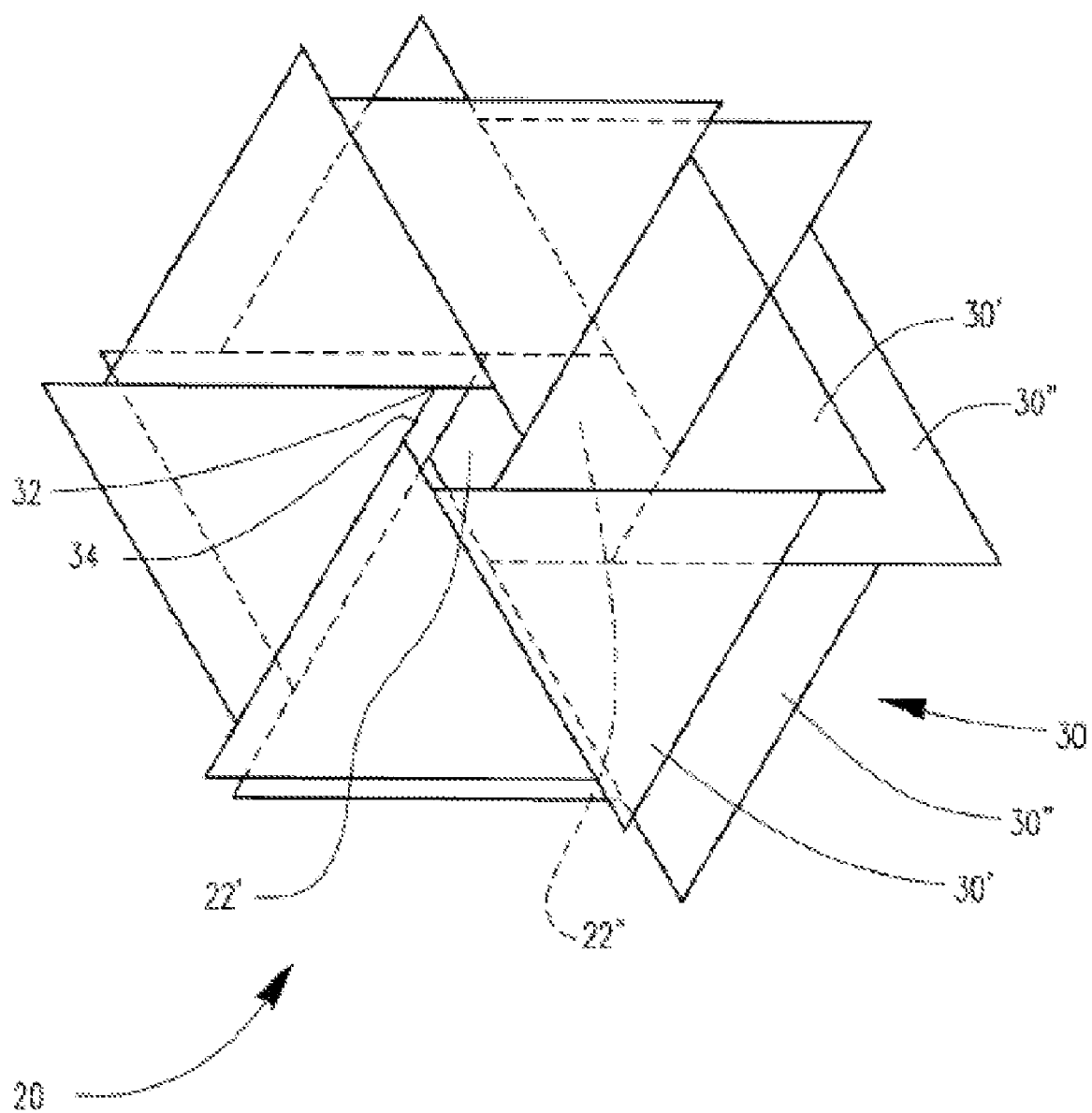
FIG. 20 is an end view of an apparatus for reducing the size of an article having a first portion of a chamber offset from a second portion of a chamber, the two portions having difference cross-sections, the apparatus in a more open configuration than shown in FIG. 18.
Figure 21:
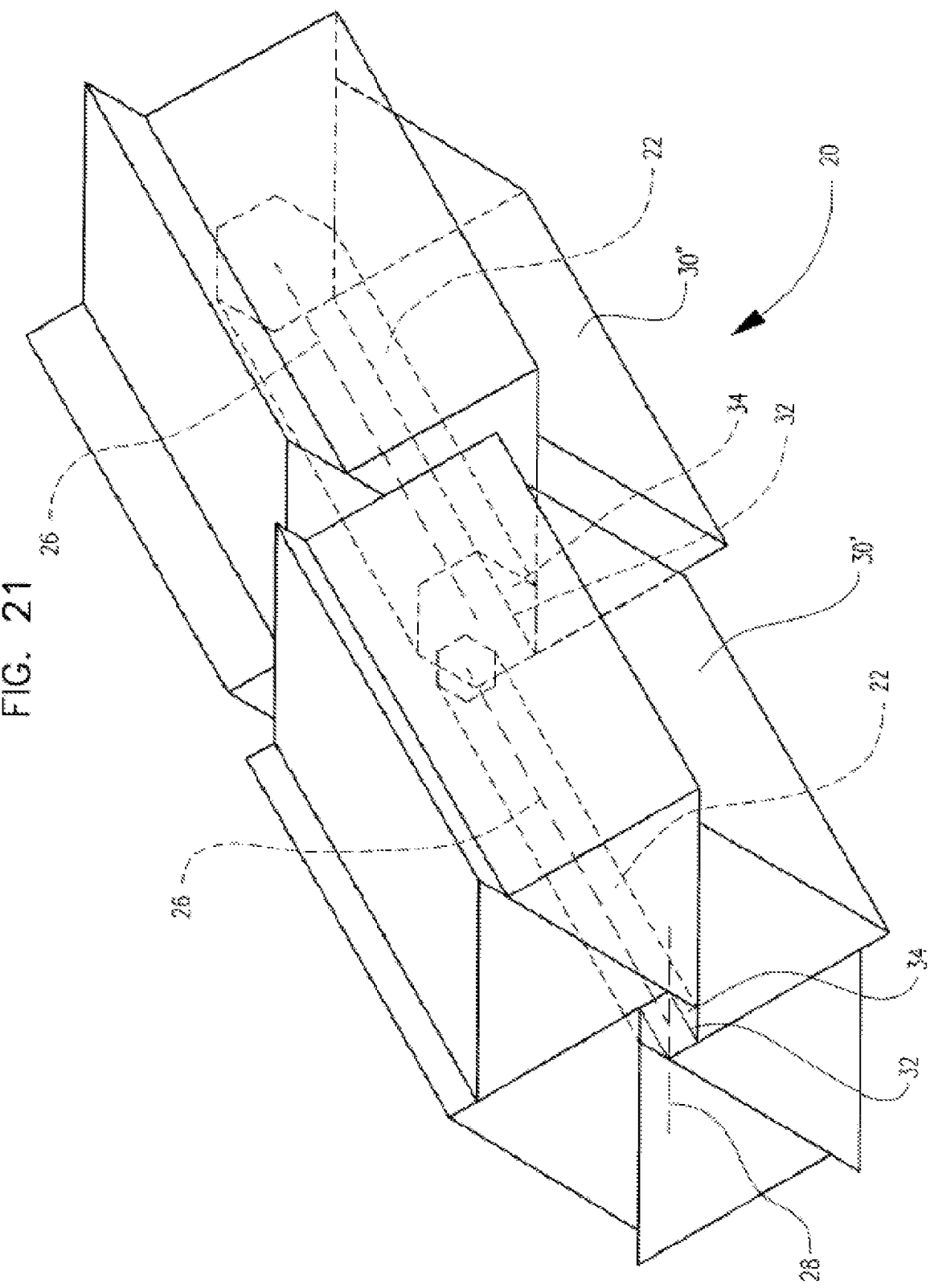
FIG. 21 is an isometric view of an apparatus for reducing the size of an article having a first portion of a chamber offset from a second portion of a chamber, the two portions having difference cross-sections, the apparatus in a more open configuration than shown in FIG. 19.

FIGS. 20 and 21 show the apparatus 20 partially open. Each portion 30', 30" of a die 30 may include an edge 32 and at least one contacting surface 34. The contacting surface 34 may contact and reduce the size of an article placed within the chamber 22. The exact shape of the iris 24 is dependent upon the shape, arrangement and number of contacting surfaces 34 included in the apparatus 20.

As shown in FIG. 21, the edge 32 of each portion 30', 30" of each die 30 may move along a movement path plane 28. All of the movement path planes 28 may intersect at a zero point line 26. A zero point line 26 may comprise the central longitudinal axis of a chamber 22. All of the edges 32 of the first portion 30' may meet at the zero point line 26 of the first portion 30' when the chamber 22 is fully contracted.

FIG. 21B shows the apparatus 20 wherein the first chamber 22' is open and the second chamber 22" is closed. The configuration of the first chamber 22' is another open configuration from the configuration shown in FIG. 21, as the edges 32 of the first portions 30' of the dies have moved through the zero point line 26 of the first chamber 22' and continued to reopen the first chamber 22' in the alternate open configuration. Thus, it is possible for the first chamber 22' to be opening as the second chamber 22" continues to close. As the dies 30 continue to travel, the edges 32 of the second portions 30" of the dies may move through the zero point line 26 of the second chamber 22" and reopen the second chamber 22" in another open configuration.

It can be seen by comparing FIGS. 19, 21 and 21B that the relation and placement of the first portion 30' and second portion 20" of each die with respect to one another remains constant.

The surface which comprises a contacting surface 34 for either portion 30', 30" of a die 30 may change as the chamber 22 configuration changes from a first open configuration to another or second open configuration.

Generally, there may be an even number of dies 30. Dies 30 that are opposite one another across the iris 24 may have edges 32 that move along a common movement path plane 28. Desirably, angles formed between movement path planes 28 at a zero point line 26 may all be similar.

At least one movement path plane 28 may be parallel to at least one engagement plane 50. For example, movement path plane 28C is parallel to engagement plane 50AB'.

Desirably, all of the dies 30 may be moved simultaneously such that each edge 32 of a portion 30', 30" may be equidistant from its zero point line 26 along its respective movement path plane 28.

The embodiment shown in FIGS. 18-21B is somewhat similar to the embodiment shown in FIG. 10 in that the zero point line 26 of the first section 30' is offset from the zero point line 26 of the second section 30". The embodiment of FIGS. 18-21 further arranges the chamber 22" of the second portion 30" in a configuration that is more open than the chamber 22' of the first portion 30'. As can be seen by comparing FIGS. 18 and 20, as the apparatus 20 opens and the cross-sections of both chambers 22 become larger, the first portion 30' and second portion 30" of each die 30 remain fixed with respect to one another.

A further embodiment of an apparatus may include a first chamber offset from a second chamber, the second chamber having a larger cross-sectional area than the first chamber, wherein each iris may comprise a nonregular polygon. The apparatus may have dies shaped similarly to the embodiment shown in FIGS. 18-21B, however, the dies may be moved according to the embodiments shown in FIGS. 3-5.

A further embodiment of an apparatus may include a first chamber offset from a second chamber, the second chamber having a larger cross-sectional area than the first chamber, wherein each iris may comprise a nonregular polygon. The apparatus may be formed using dies having a first portion offset from a second portion, wherein the portions of each die may be shaped according to the embodiment shown in FIGS. 6-8.

Referring to FIGS. 22-28, an embodiment of an apparatus 20 for reducing the size of an article may comprise a plurality of movable dies 30 having a chamber 22. The chamber 22 may be tapered along its length.

All of the dies 30 may have the same shape. Each die 30 may be adjacent to at least one other die 30. Adjacent dies 30 may be slidably engaged with one another along an engagement plane 50. The dies 30 may be arranged to form a chamber 22 that may run the length of the device. Each engagement plane 50 may be nonparallel to the central longitudinal axis 26 of the chamber 22. Wall surfaces or contacting surfaces 34 which bound the chamber 22 may comprise an iris 24.

Figure 22:
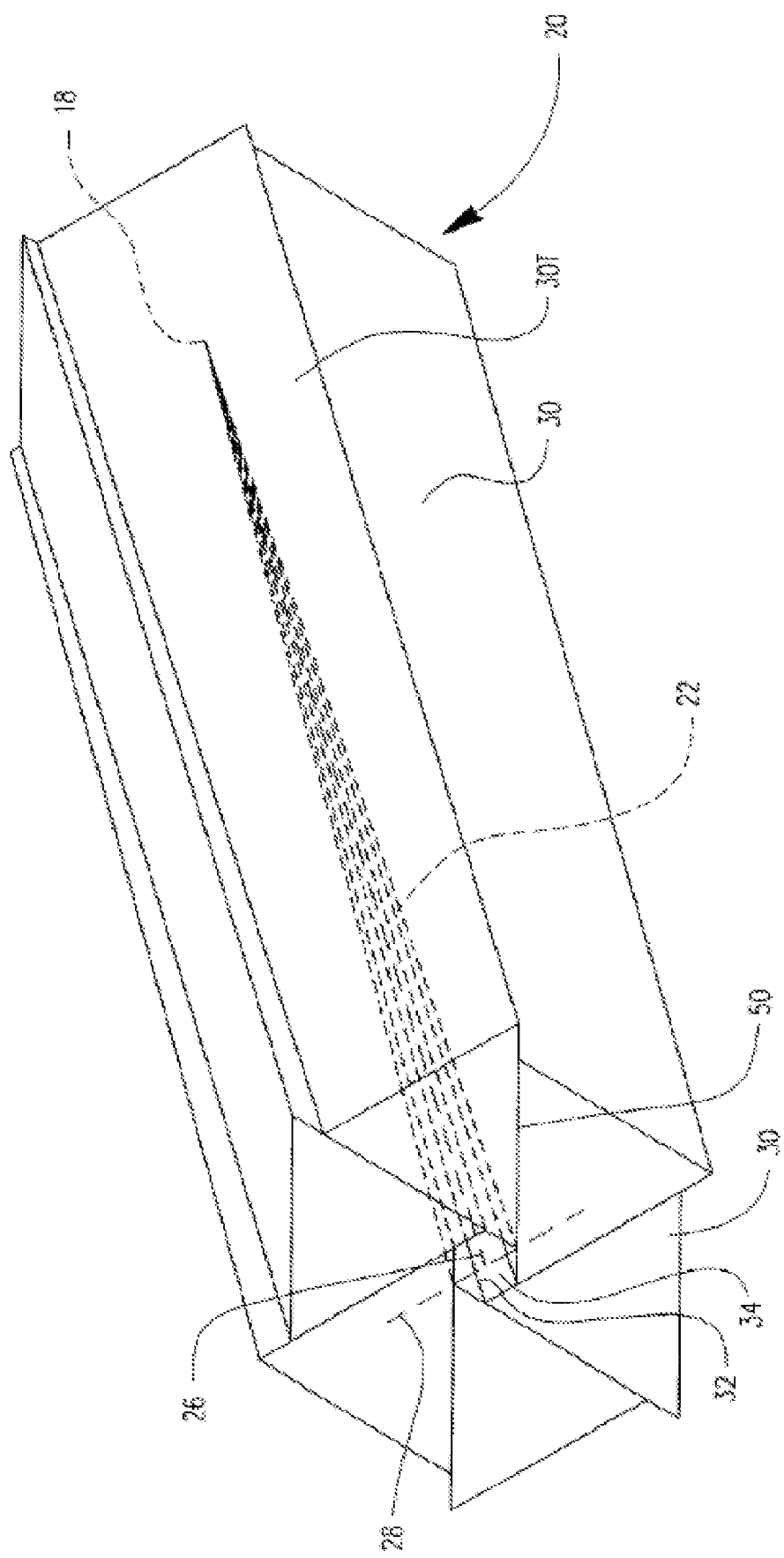
FIG. 22 is an isometric view of an apparatus for reducing the size of an article having a tapered chamber.

Each die 30 may include an edge 32 and at least one contacting surface 34. A contacting surface 34 may contact and reduce the size of an article placed within the chamber 22. Each edge 32 may move along a movement path plane 28. For example, the edge 32 of die 30c may move along the movement path plane 28 as shown in FIG. 22. A movement path plane 28 may extend along the length of the apparatus 20.

An intersection of movement path planes 28 may comprise a zero point line 26. A zero point line 26 may comprise the central longitudinal axis of the chamber 22. A plurality of portions of die edges 32 may meet at a point on the zero point line 26 when the chamber 22 is fully contracted, such as represented at meeting point 18 of FIG. 22.

The edge 32 of each die 30 may be oriented at an angle to the zero point line 26. The edge 32 of each die 30 may offset laterally along its movement path plane 28 as the die 30 is traversed from one end to the other.

Figure 23:
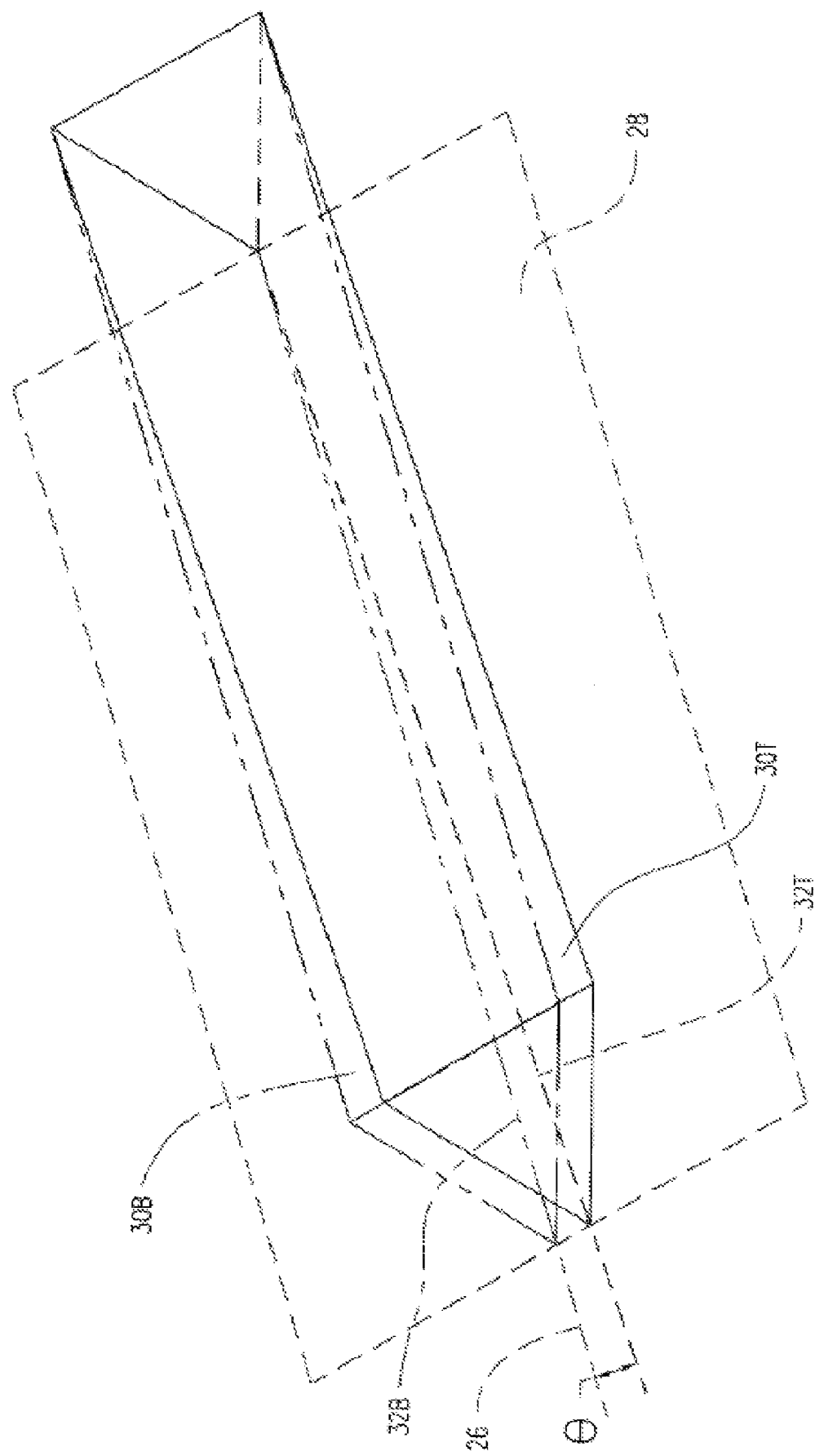
FIG. 23 shows an inventive die from the embodiment of FIG. 22 as compared to a die from the embodiment of FIG. 2.

FIG. 23 compares a die 30T according to an embodiment of the invention having a tapered chamber with a die 30B according to an embodiment having a nontapered chamber. Die 30T represents die 30T from FIG. 22. Die 30B is similar to die 30B of FIG. 2. In the die 30B which may be used to form a nontapered chamber, the edge 32B may be parallel to the zero point line 26 or central longitudinal axis of the chamber. In the die 30T which may be used to form a tapered chamber, the edge 32T may be oriented at a non-zero angle θ to the zero point line 26. The edge 32T may offset along its movement path plane 28 along the length of the die.

Figure 24:
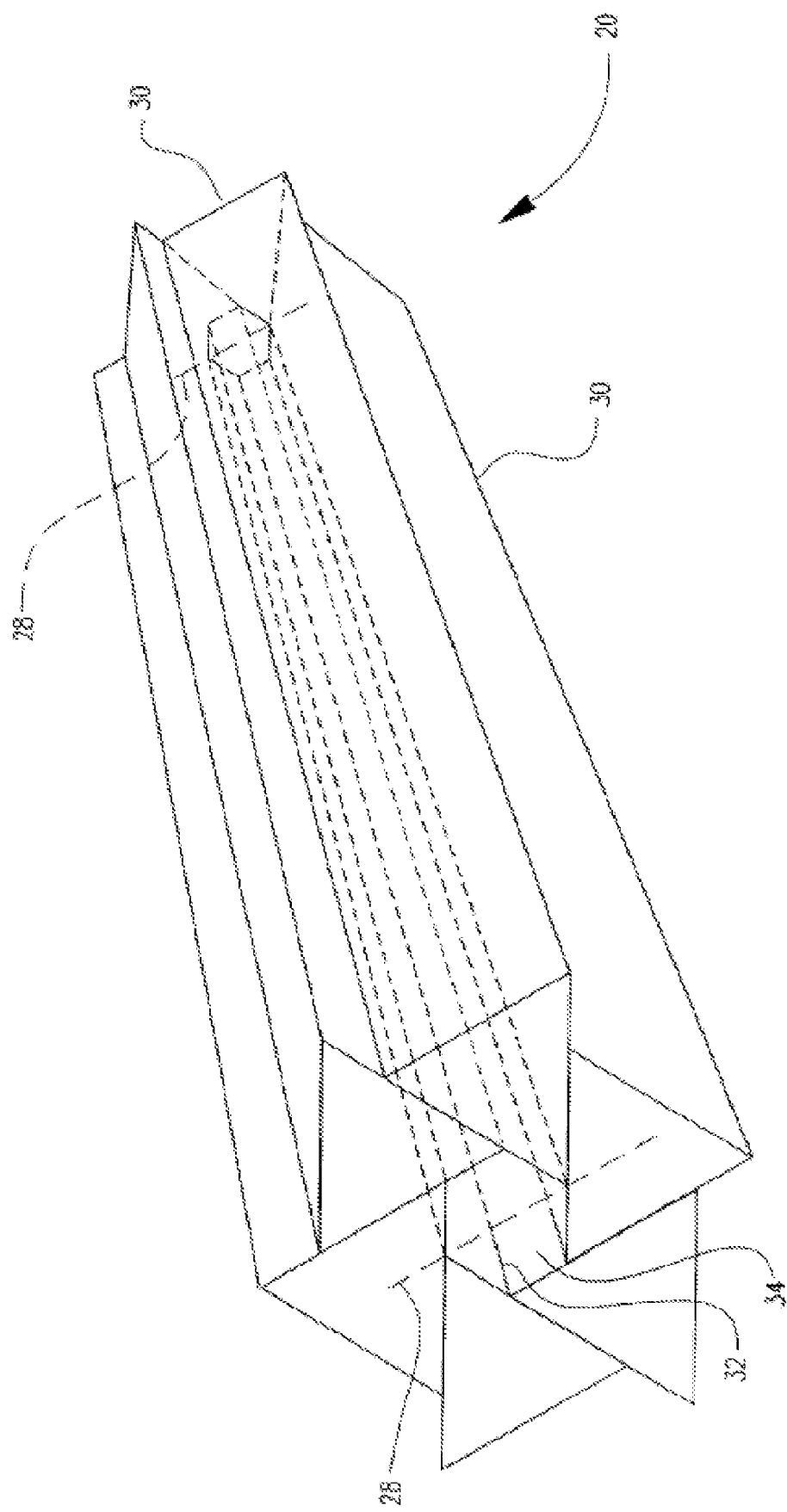
FIG. 24 is an isometric view of an apparatus for reducing the size of an article having a tapered chamber in a more open configuration than shown in FIG. 22.

FIG. 24 shows the apparatus 20 of FIG. 22 in a more opened configuration. An iris 24 may comprise a regular polygon. The size of the iris 24 may change along the length of the apparatus 20.

The apparatus 20 may have an even number of dies 30. Dies 30 that have contacting surfaces 34 opposite one another across the iris 24 may have edges 32 that move along a common movement path plane 28. Desirably, angles formed between movement path planes 28 at a zero point line 26 may all be similar.

Figure 25:
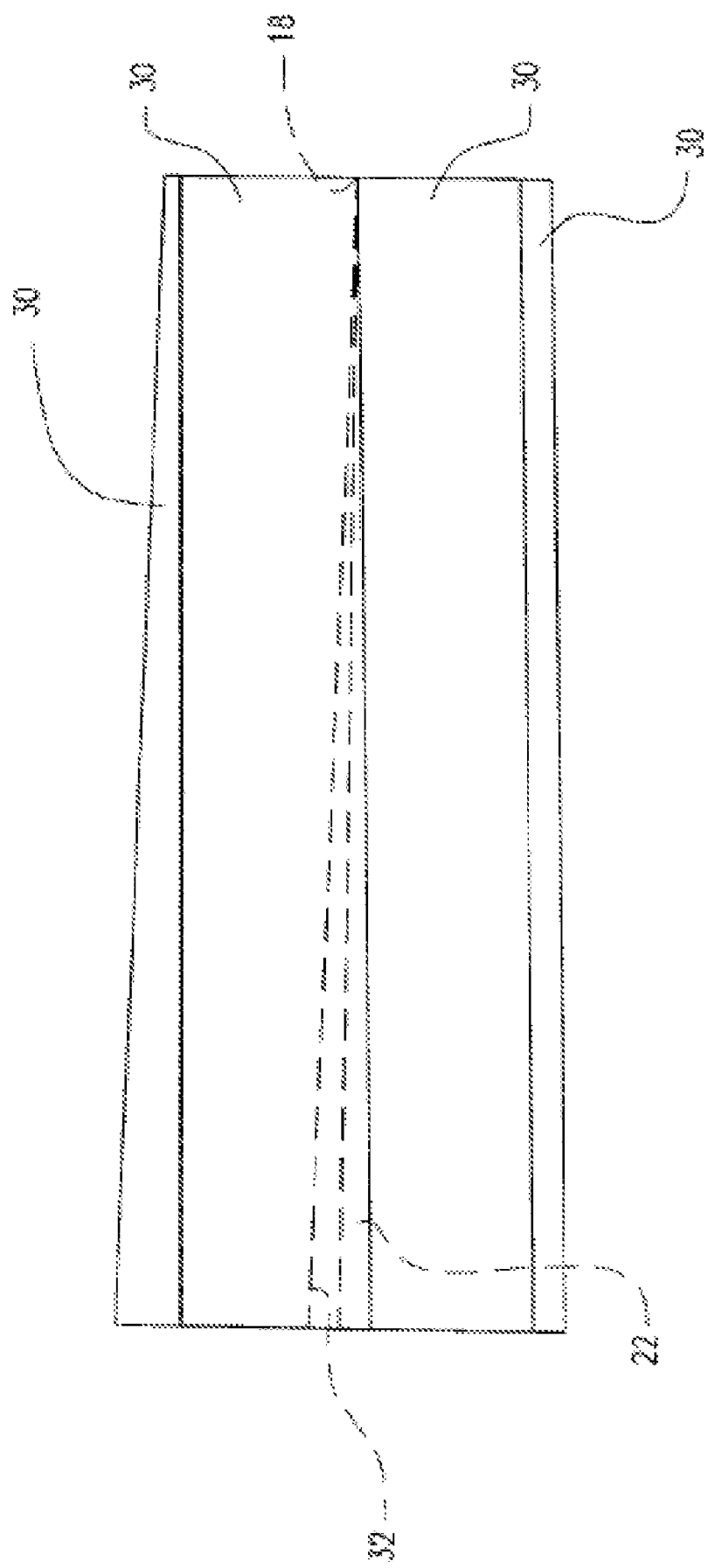
FIG. 25 shows a side view of an apparatus for reducing the size of an article having a tapered chamber.
Figure 26:
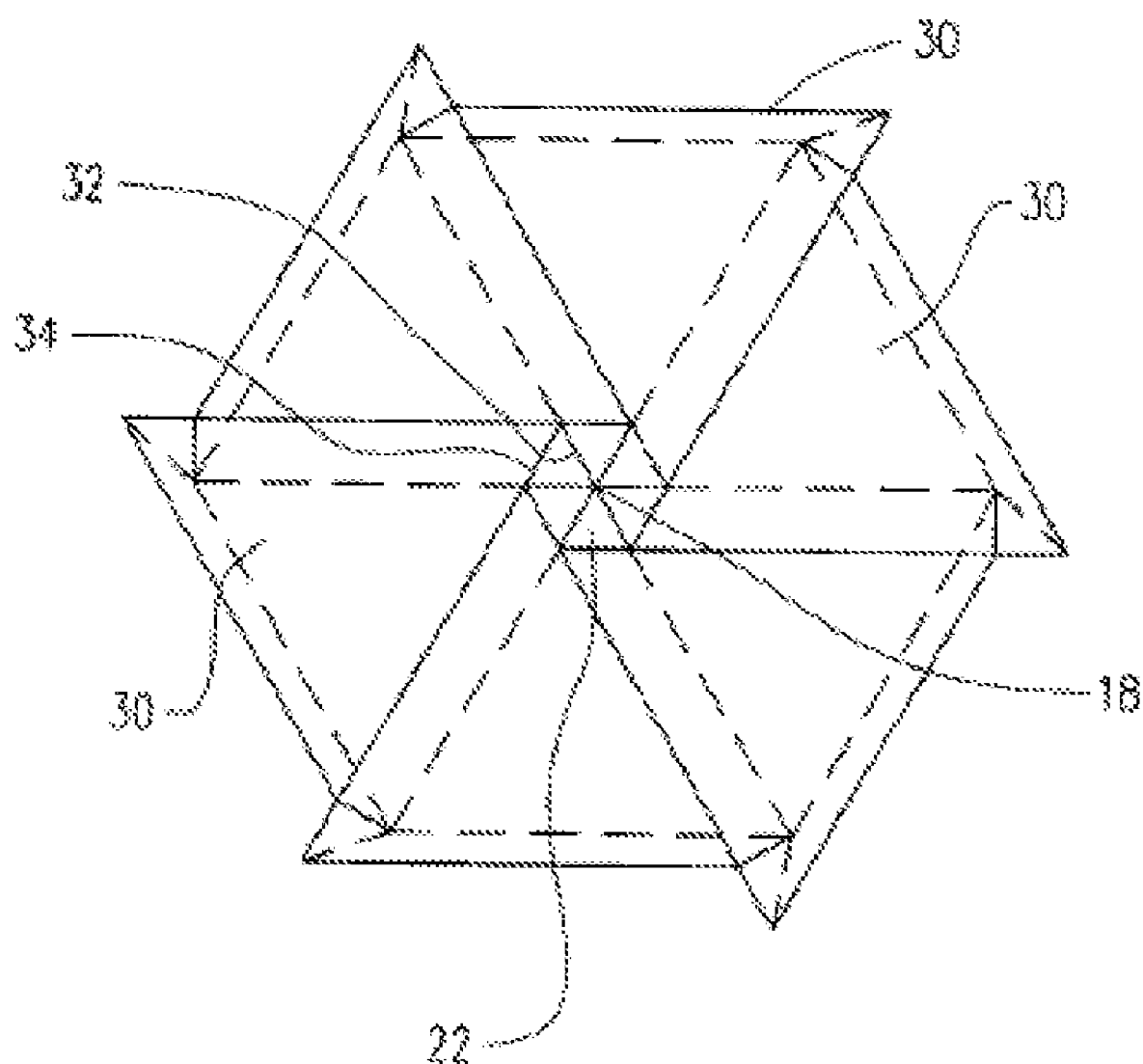
FIG. 26 shows an end view of an apparatus for reducing the size of an article having a tapered chamber.

FIGS. 25 and 26 depict the apparatus 20 in a closed configuration where a portion of all edges 32 meet at a meeting point 18 on the zero point line 26.

Figure 27:
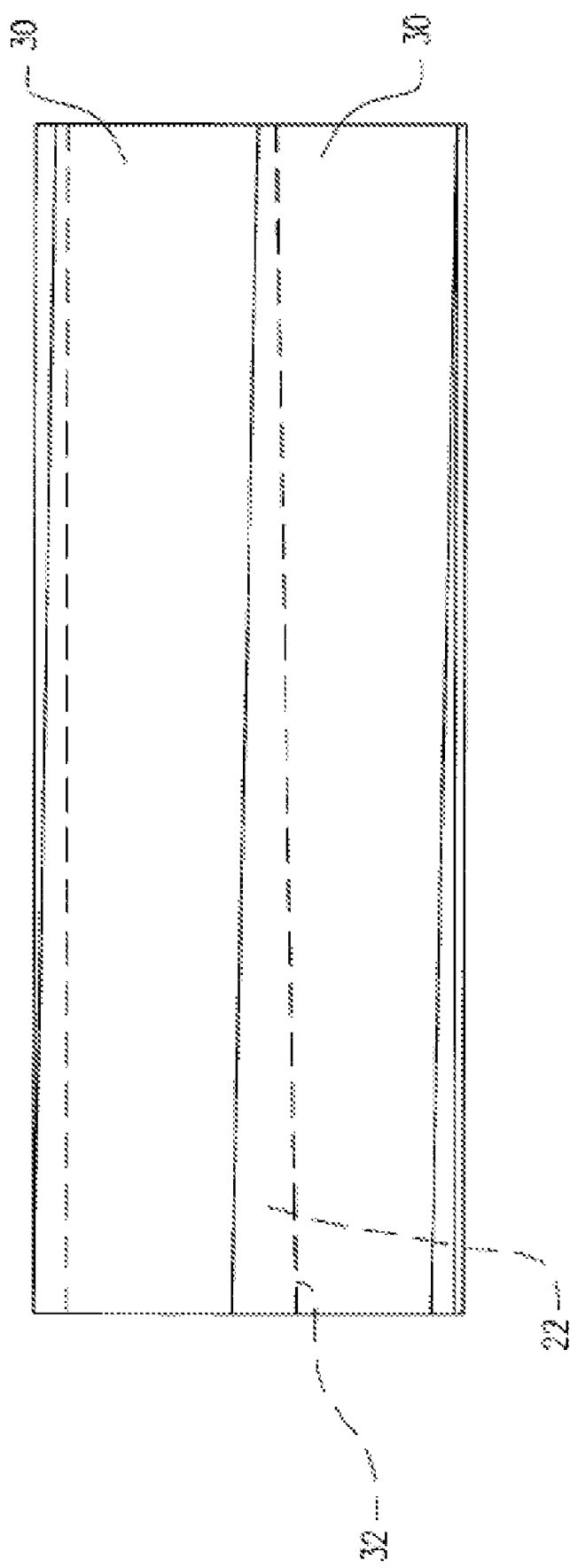
FIG. 27 shows a side view of an apparatus for reducing the size of an article having a tapered chamber in a more open configuration than shown in FIG. 25.
Figure 28:
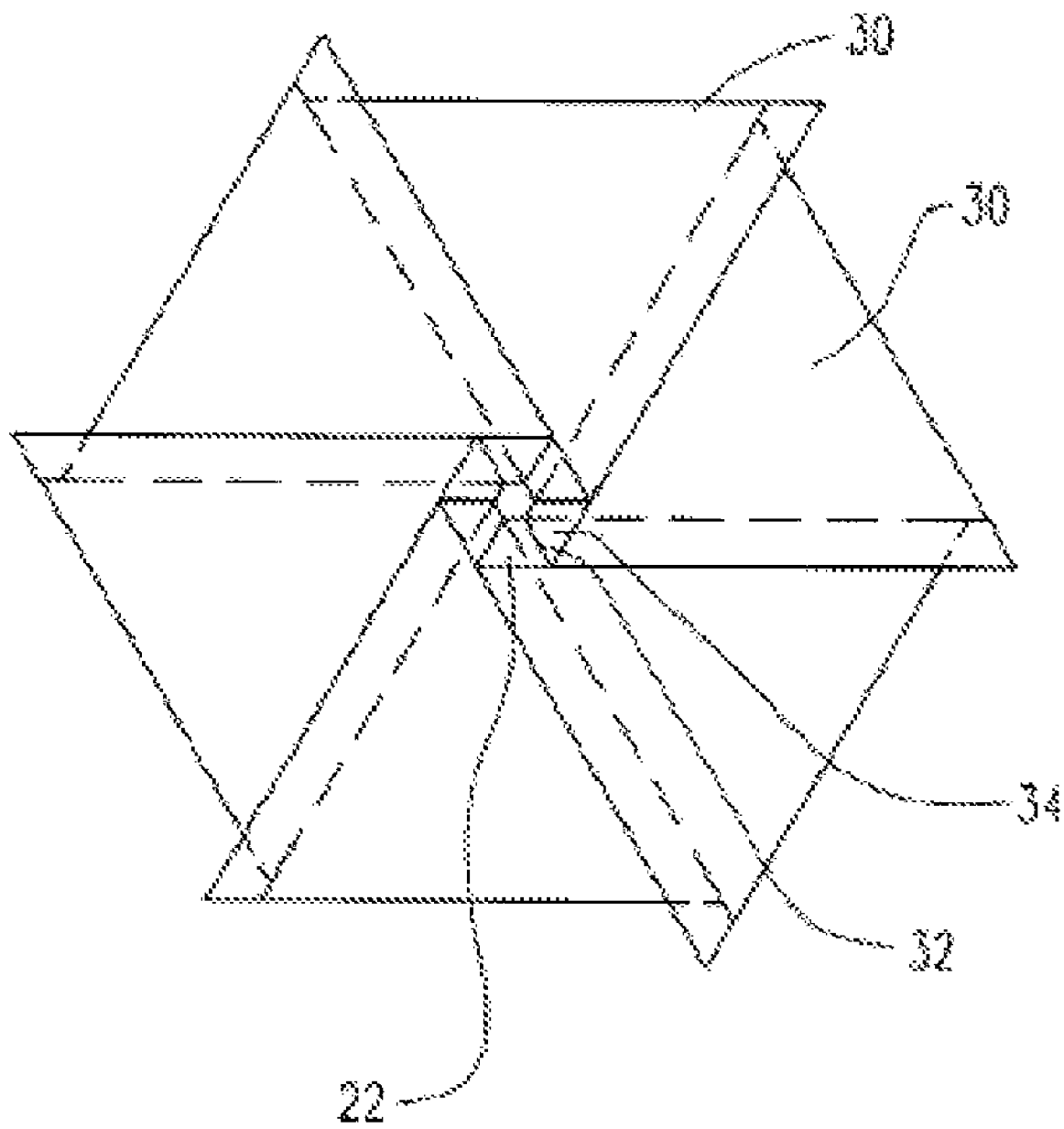
FIG. 28 shows an end view of an apparatus for reducing the size of an article having a tapered chamber in a more open configuration than shown in FIG. 26.

FIGS. 27 and 28 depict the apparatus 20 in a more open configuration.

A further embodiment may be formed having a chamber that is tapered along the length of the device, wherein a cross-section of the chamber comprises a nonregular polygon. Such an embodiment may be formed by modifying the dies of the embodiment shown in FIGS. 6-8 to include edges 32 that are oriented at an angle to the zero point line. The edge may offset along its movement path plane along the length of the die.

Figure 29:
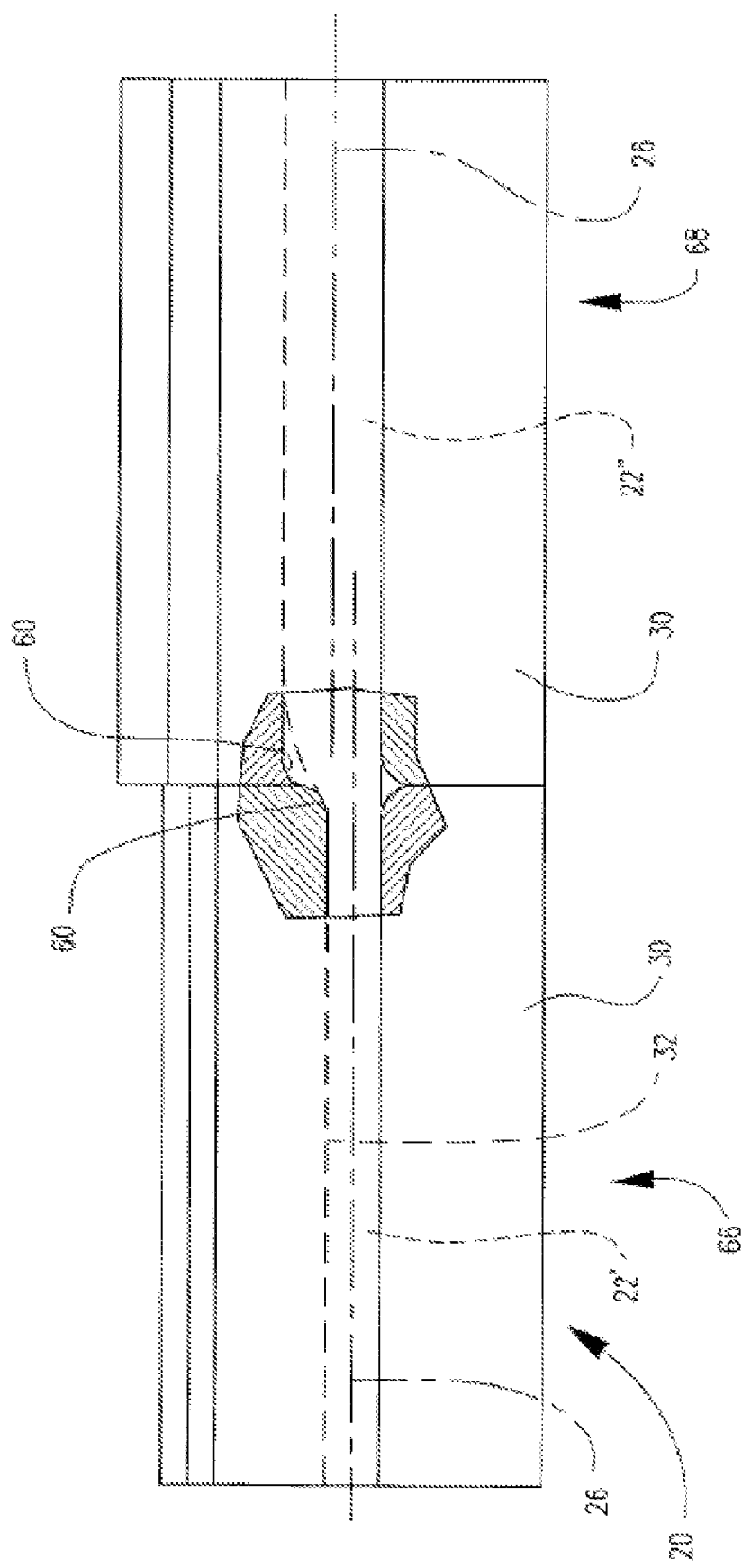
FIG. 29 shows a side view and partial sectional view of an apparatus for reducing the size of an article having a first chamber and a second chamber.
Figure 30:
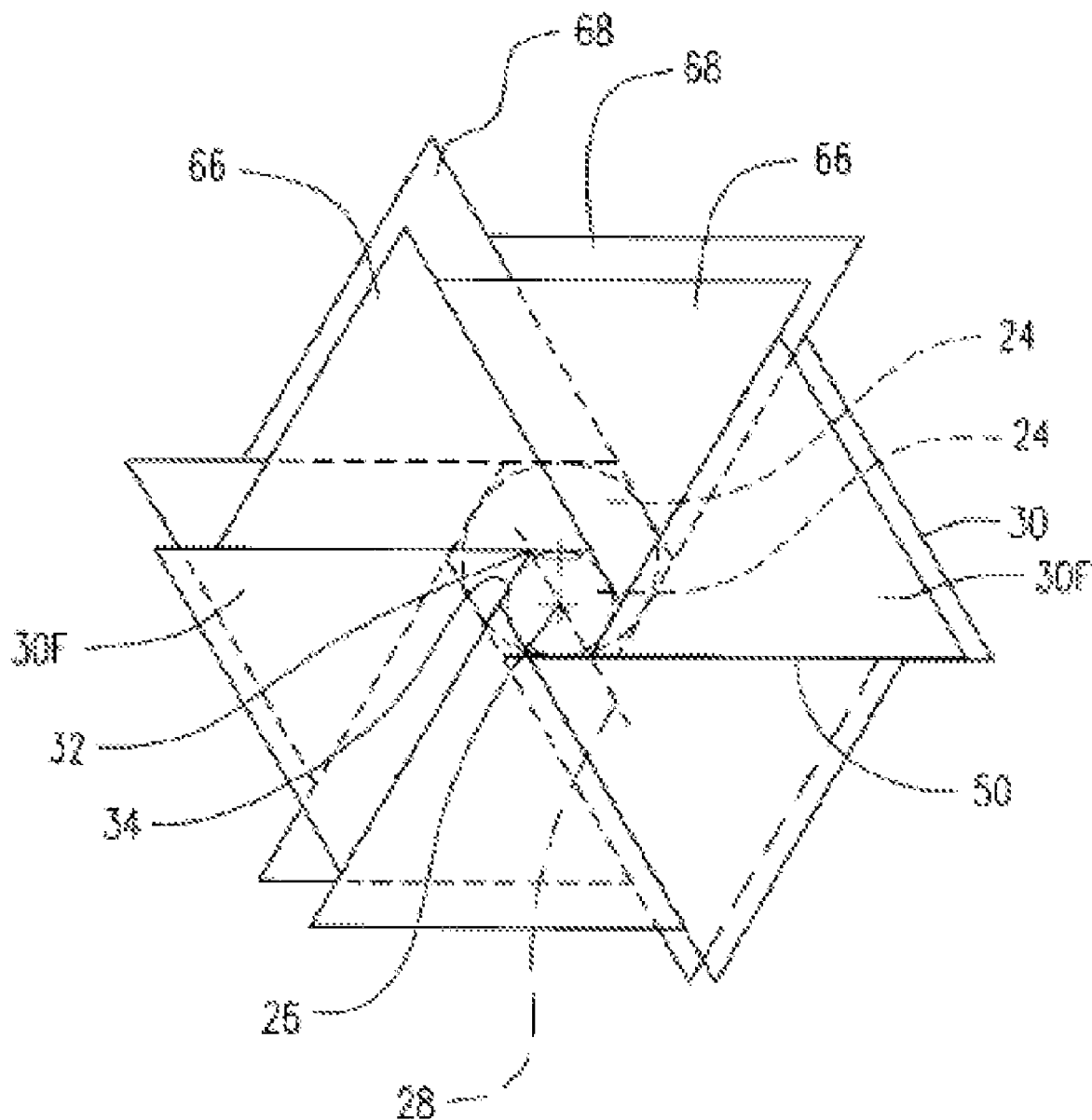
FIG. 30 shows an end view of an apparatus for reducing the size of an article having a first chamber and a second chamber.

FIGS. 29 and 30 show an apparatus 20 comprising a first group 66 of dies 30 arranged to form a first chamber 22' and a second group 68 of dies 30 arranged to form a second chamber 22''. The dies 30 of the first group 66 may be adjusted independently from the dies 30 of the second group 68, or in concert with the dies 30 of the second group 68. The dies of any of the embodiments described herein may be used to form the first group 66 and/or the second group 68.

Each die 30 may be adjacent to at least one other die 30 from the same group 66, 68. Adjacent dies 30 of a group 66, 68 may be slidably engaged with one another along an engagement plane 50. Wall surfaces or contacting surfaces 34 which bound either chamber 22, 22' may comprise an iris 24.

Each die 30 may include an edge 32 and at least one contacting surface 34. A contacting surface 34 may contact and reduce the size of an article placed within the chamber 22', 22''. Each edge 32 may move along a movement path plane 28. An intersection of movement path planes 28 may comprise a zero point line 26, wherein a plurality of die edges 32 meet when the iris 24 is fully contracted.

Each group 66, 68 of the apparatus 20 may have an even number of dies 30. Dies 30 that have contacting surfaces 34 opposite one another across an iris 24 may have edges 32 that move along a common movement path plane 28. For example, the movement path plane 28 in FIG. 30 comprises a movement path plane for the two dies labeled 30F.

Desirably, all of the dies 30 of a group 66, 68 may be moved simultaneously such that each edge 32 may be the same predetermined distance away from its zero point line 26 as all other edges 32 are away from their respective zero point lines 26 at any given time.

In some embodiments, the longitudinal axis of the first chamber 22' may be offset from the longitudinal axis of the second chamber 22''.

In some embodiments, the iris 24 of the first chamber 22' may be a different shape than the iris 24 of the second chamber. For example, the iris 24 of the first chamber 22' may comprise a regular polygon, while the iris 24 of the second chamber 22'' may comprise a nonregular polygon. The exact shape of the iris 24 of either chamber 22', 22'' is dependent upon the shape, arrangement and number of contacting surfaces 34 included in the apparatus 20.

The apparatus 20 may be used to reduce the size of an article placed within either chamber 22', 22''. The apparatus may also be used to reduce the size of a first portion of an article within the first chamber 22' to a first size and a second portion of an article within the second chamber 22'' to a second size.

The dies 30 of either group 66, 68 may include a rounded edge end portion 60, as shown in FIG. 29. Rounded edge end portions 60 may provide a more gradual transition between the first chamber 22' and the second chamber 22''. A rounded edge portion 60 may be rounded in a direction toward the center of the chamber or away from the center of the chamber.

Figure 31:
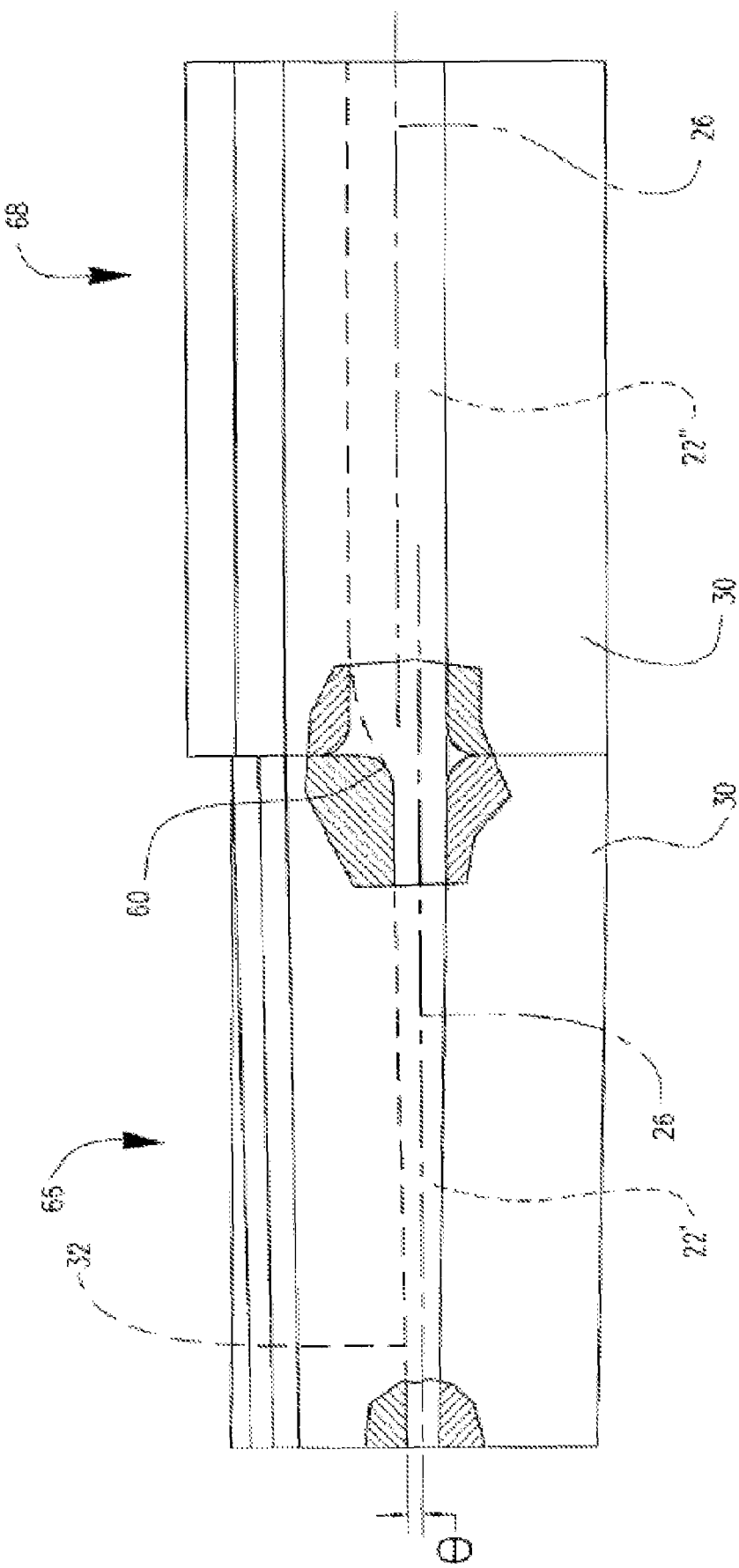
FIG. 31 shows a side view and partial sectional view of an apparatus for reducing the size of an article having a first chamber and a second chamber, the first chamber having a taper.

FIG. 31 shows another embodiment of an apparatus 20 for reducing the size of an article. The embodiment is similar to the embodiments described with respect to FIGS. 29 and 30, but further includes a tapered first chamber 22'. A taper may be achieved by providing dies 30 having an edge 32 that is oriented at a non-zero angle θ to the zero point line 26 and having a lateral offset along its movement path plane 28 along the length of the die 30, as described herein with respect to the embodiments of FIGS. 22-24.

FIGS. 32-35 show an embodiment of an apparatus 20 having a chamber 22. The chamber 22 may have portions of increased cross-sectional area 70.

The apparatus 20 may comprise a plurality of movable dies 30. All of the dies 30 may have the same physical shape. Each die 30 may be adjacent to at least one other die 30. Adjacent dies 30 may be slidably engaged with one another. The dies 30 may be arranged to form a chamber 22 that may run the length of the device. Wall surfaces or contacting surfaces 34 which bound the chamber 22 may comprise an iris 24.

Figure 32:
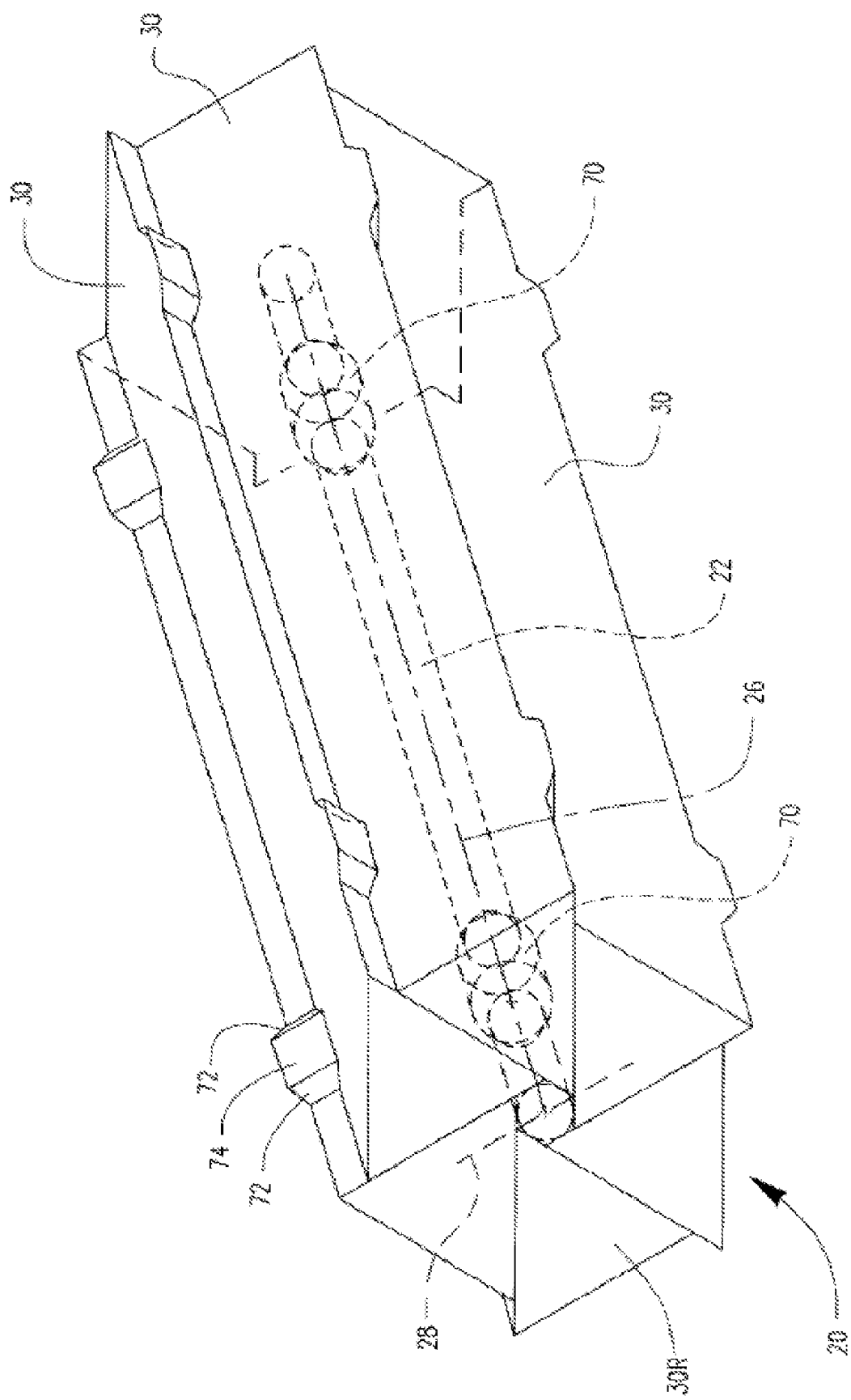
FIG. 32 shows an isometric view of an apparatus for reducing the size of an article having a chamber with portions of a first size and portions of a second size.
Figure 33:
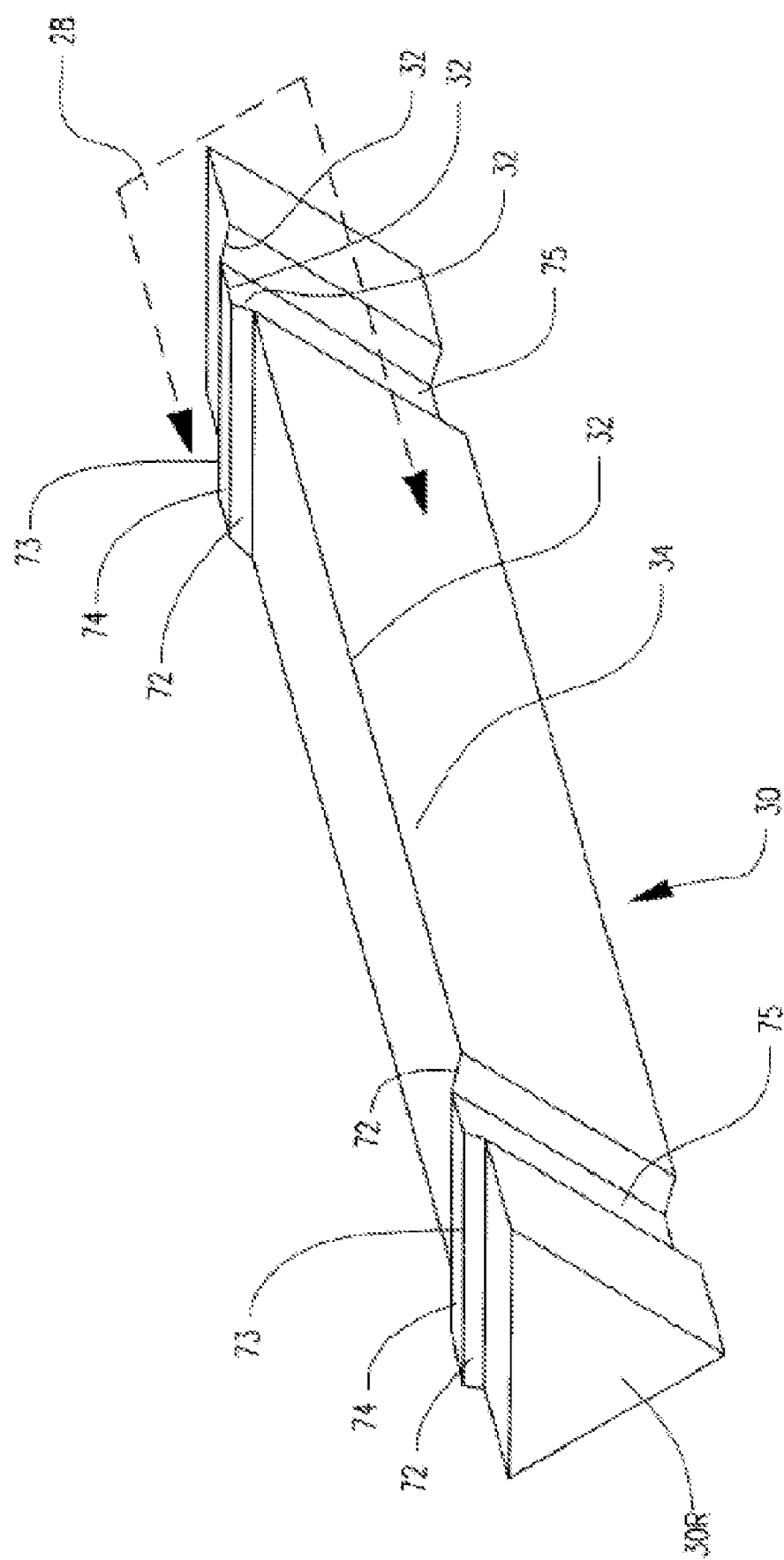
FIG. 33 shows an inventive die.
Figure 34:
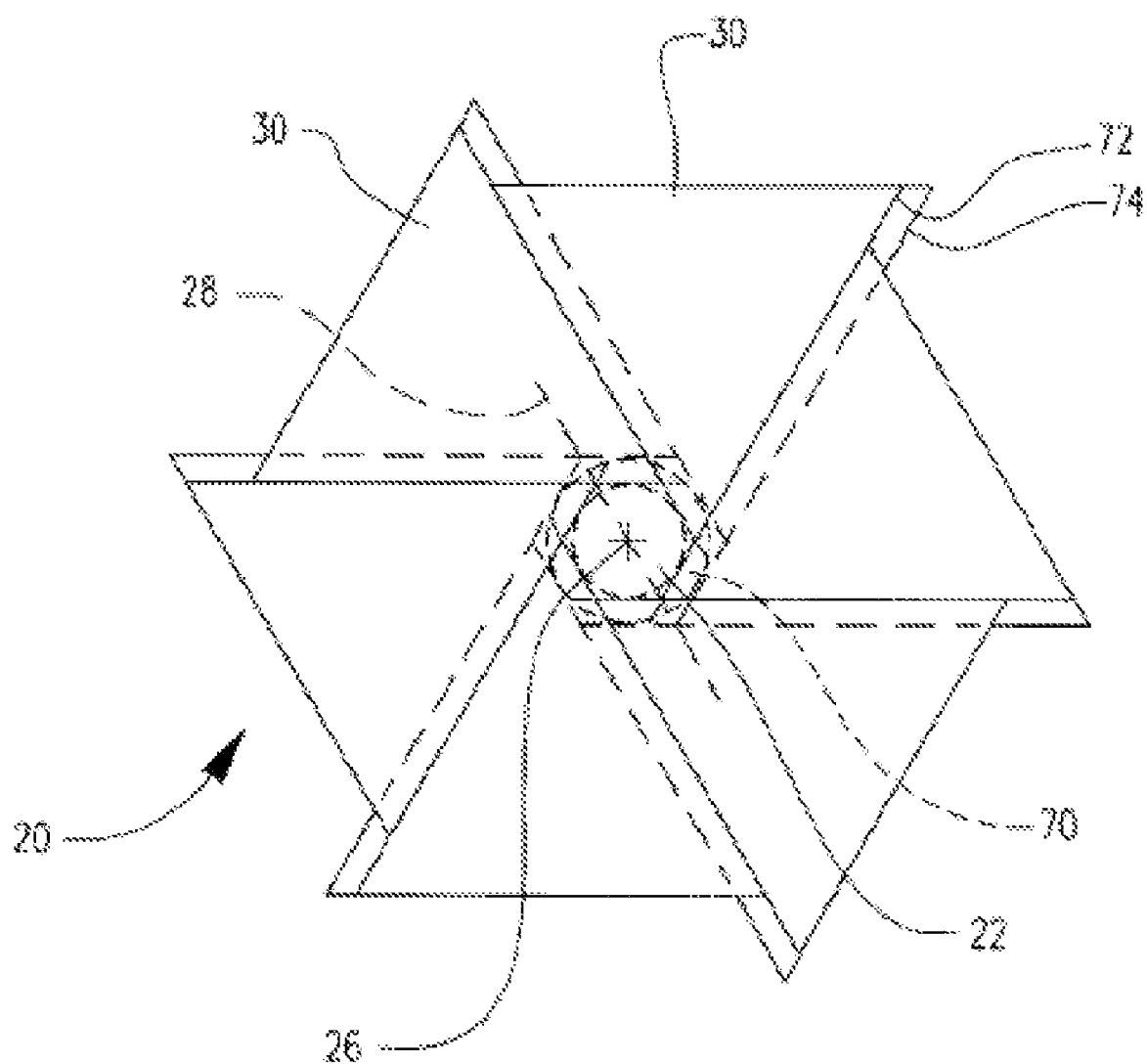
FIG. 34 shows an end view of an apparatus for reducing the size of an article having a chamber with portions of a first size and portions of a second size.

FIG. 33 shows die 30R of FIG. 32 in greater detail. Each die 30 may include at least one offset portion 74. Each die 30 may further include a transition portion 72 on either side of each offset portion 74. Transition portions 72 may provide a transition segment in the chamber 22 between portions of nominal cross-sectional area and portions of increased cross-sectional area 70. In some embodiments, a transition portion 72 may provide the chamber 22 with a taper. Offset portions 74 and transition portions 72 may have the same cross-sectional shape as other portions of the die 30. Offset portions 74 may create a raised portion 73 in one side of the die 30 and an indented portion 75 in another side of a die 30. An indented portion 75 of a first die 30 may receive a raised portion 73 of an adjacent die 30.

Each die 30 may include an edge 32 in proximity to the chamber and a plurality of contacting surfaces 34. The edge 32 may extend across transition portions 72 and offset portions 74. A contacting surface 34 may contact and reduce the size of an article placed within the chamber 22.

The shape of the chamber 22 is dependent upon the exact shape and number of dies 30 used in the apparatus. The shape of the chamber 22 is further dependent upon the number of offset portions 74 and transition portions 72 of each die 30. Although the chamber 22 represented by hidden lines in FIG. 32 depicts a circular cross-sectional shape for simplicity, it should be understood that an actual iris 24 may comprise a polygon. The number of sides of the iris 24 may be equal to the number of dies 30 that form the iris 24. It should also be understood that the polygonal iris 24 may be used to reduce the size of an article, such as a stent, having a circular or ovular cross-section.

The edge 32 of each die 30 may move along a movement path plane 28 as the apparatus 20 is opened or closed, thereby adjusting the cross-sectional size of the chamber 22. Desirably, offset portions 74 and transition portions 72 include edge 32 portions that lie in the movement path plane 28 of the die 30. Thus, all portions of a die edge 32 may be located in the movement path plane 28 of the die 30.

An intersection of movement path planes 28 may comprise a zero point line 26, wherein a plurality of die edge 32 portions may meet when the iris 24 is fully contracted. As shown in FIGS. 32-35, the offset portions 74 create portions of increased cross-sectional area 70 in the chamber 22.

Portions of increased cross-sectional area 70 may be used to crimp marker bands, such as radiopaque markers or MRI markers. For example, a catheter tube having at least one marker band disposed thereabout may be placed in the chamber 22, the marker band being disposed in a portion of increased cross-sectional area 70. The size of the chamber 22 may then be reduced so as to contact the marker band and crimp it onto the catheter.

Multiple marker bands may also be used. Multiple marker bands may be disposed within a common portion of increased cross-sectional area 70, or bands may be disposed within separate portions of increased cross-sectional area 70. Thus, a plurality of marker bands may be crimped simultaneously, each marker band being crimped to specific predetermined tolerances according to the size and shape of the portion of increased cross-sectional area 70 in which the band is disposed.

The crimping tolerances for each marker band may be similar to or dissimilar from other bands being crimped, and the distances between bands along the length of the catheter are predetermined and common between catheters formed using the apparatus 20. Thus, variations in marker shape, size and placement upon the catheter may be reduced when using the apparatus 20.

Portions of increased cross-sectional area 70 may also be shaped to allow a predetermined shaping of a marker band during crimping. For example, marker bands may be reduced to a noncircular cross section, such as an ellipse. Marker bands may also be crimped to include a tapered shape along the longitudinal axis of the catheter.

The apparatus 20 may have an even number of dies 30. Dies 30 that have contacting surfaces 34 opposite one another across the iris 24 may have edges 32 that move along a common movement path plane 28. The angles formed between intersecting movement path planes 28 at a zero point line 26 may all be similar. Desirably, all of the dies 30 may be moved simultaneously such that an iris 24 may comprise a regular polygon.

Figure 35:
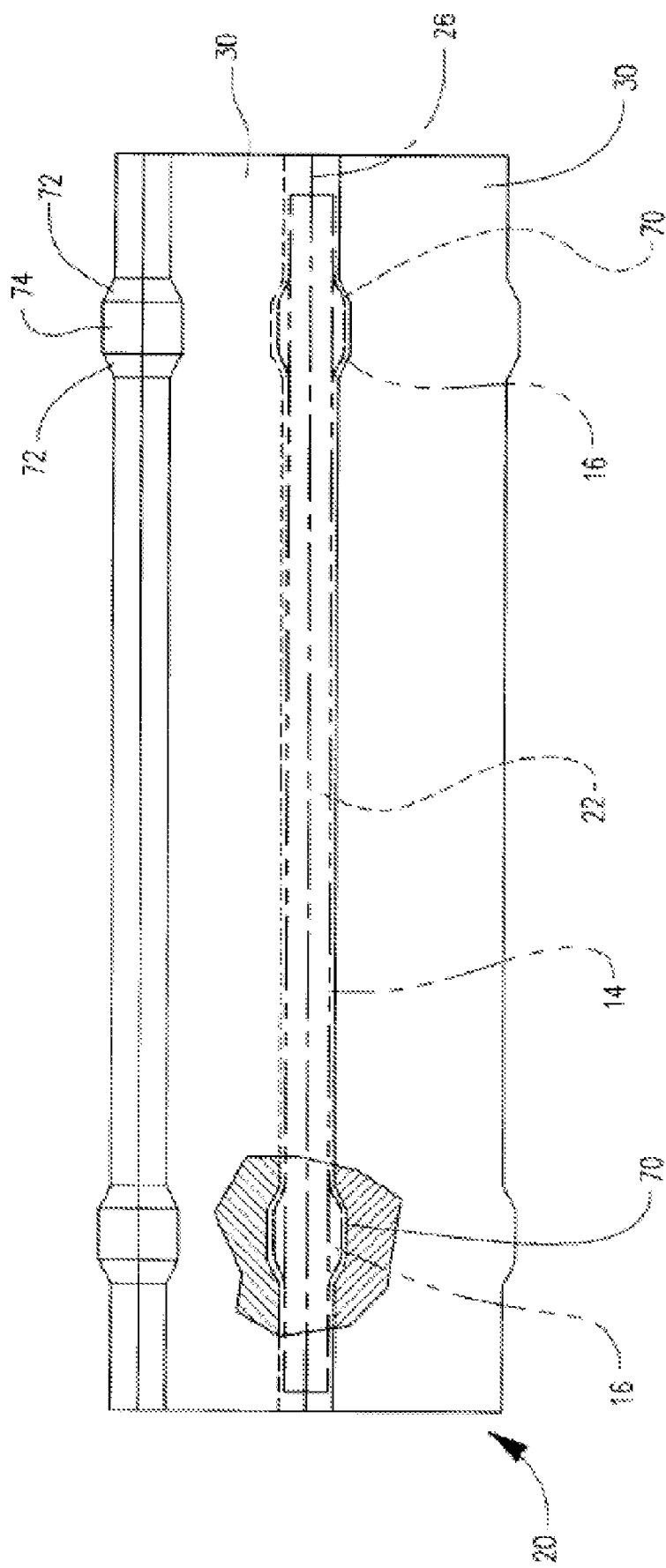
FIG. 35 shows a side and partial section view of an apparatus for reducing the size of an article having a chamber with portions of a first size and portions of a second size.

FIG. 35 shows the apparatus 20 with a stent 14 disposed within the chamber 22. The apparatus 20 may be used to reduce the size of a stent 14. A stent 14 may include elements 16 which may have a greater diameter than other portions of the stent 14, or may desirably have a greater diameter than other portions of the stent 14 after the apparatus 20 reduces the diameter of the stent 14. For example, elements 16 may comprise radiopaque or MRI markers or marker bands, hubs, bifurcations, grafts, sidebranch ports and the like. The stent 14 may be positioned such that any elements 16 are within portions of increased cross-sectional area 70 in the chamber 22. Thus, the elements 16 may retain a larger size than other portions of the stent 14 after the apparatus 20 is contracted.

In another embodiment, the dies 30 of the embodiment having a nonregular polygonal iris, such as shown in FIGS. 6-8, may be modified to include offset portions 74 and transition portions 72 as described with respect to the embodiment shown in FIGS. 32-35. Thus, an apparatus may include a chamber having a nonregular polygonal cross-section and portions of increased cross-sectional area 70.

Figure 36:
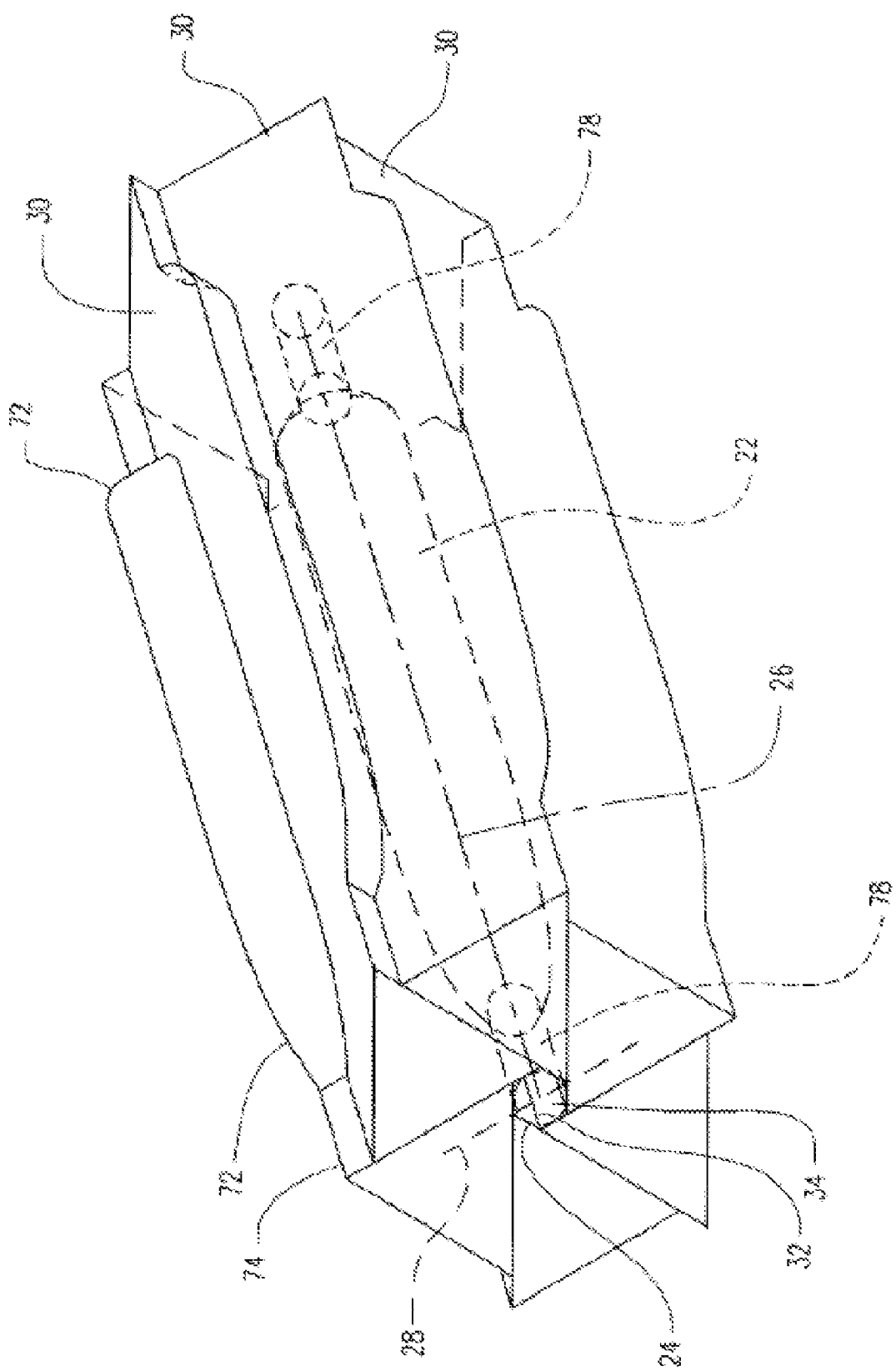
FIG. 36 shows an isometric view of an apparatus for reducing the size of an article having a chamber with portions of varying cross-section.

FIG. 36 shows another embodiment of an apparatus 20 having a chamber 22. The chamber 22 may have portions of reduced cross-sectional area 78.

The apparatus 20 may comprise a plurality of movable dies 30. All of the dies 30 may have the same physical shape. Each die 30 may be adjacent to at least one other die 30. Adjacent dies 30 may be slidably engaged with one another. The dies 30 may be arranged to form a chamber 22 that may run the length of the device. Wall surfaces or contacting surfaces 34 which bound the chamber 22 may comprise an iris 24.

Each die 30 may include at least one offset portion 74. Each die 30 may further include a transition portion 72 adjacent to an offset portion 74. When a portion of reduced cross-sectional area 78 is not located at the end of a chamber 22, transition portions 72 may be located on both sides of the offset portion 74. Transition portions 72 may provide a transition segment in the chamber 22 between portions of nominal cross-sectional area and portions of reduced cross-sectional area 78. In some embodiments, a transition portion 72 may provide the chamber 22 with a taper. Offset portions 74 and transition portions 72 may have the same cross-sectional shape as other portions of the die 30. Offset portions 74 may create a raised portion in one side of the die 30 and an indented portion in another side of a die 30. An indented portion of a first die 30 may receive a raised portion of an adjacent die 30.

Each die 30 may include an edge 32 in proximity to the chamber and a plurality of contacting surfaces 34. The edge 32 may extend across transition portions 72 and offset portions 74. A contacting surface 34 may contact and reduce the size of an article placed within the chamber 22.

The shape of the chamber 22 is dependent upon the exact shape and number of dies 30 used in the apparatus. The shape of the chamber 22 is further dependent upon the number of offset portions 74 and transition portions 72 of each die 30. The number of sides of an iris 24 may be equal to the number of dies 30 that form the iris 24.

The edge 32 of each die 30 may move along a movement path plane 28 as the apparatus 20 is opened or closed, thereby adjusting the cross-section of the chamber 22. Desirably, offset portions 74 and transition portions 72 include edge 32 portions that lie in the movement path plane 28 of the die 30. Thus, all portions of a die edge 32 may be located in the movement path plane 28 of the die 30.

An intersection of movement path planes 28 may comprise a zero point line 26. A zero point line 26 may comprise a central longitudinal axis of a chamber. A plurality of die edge 32 portions of offset portions 74 may meet at a zero point line 26 when the iris 24 is fully contracted.

The apparatus 20 may have an even number of dies 30. Dies 30 that have contacting surfaces 34 opposite one another across the iris 24 may have edges 32 that move along a common movement path plane 28. The angles formed between intersecting movement path planes 28 at a zero point line 26 may all be similar. Desirably, all of the dies 30 may be moved simultaneously such that an iris 24 may comprise a regular polygon.

Figure 37:
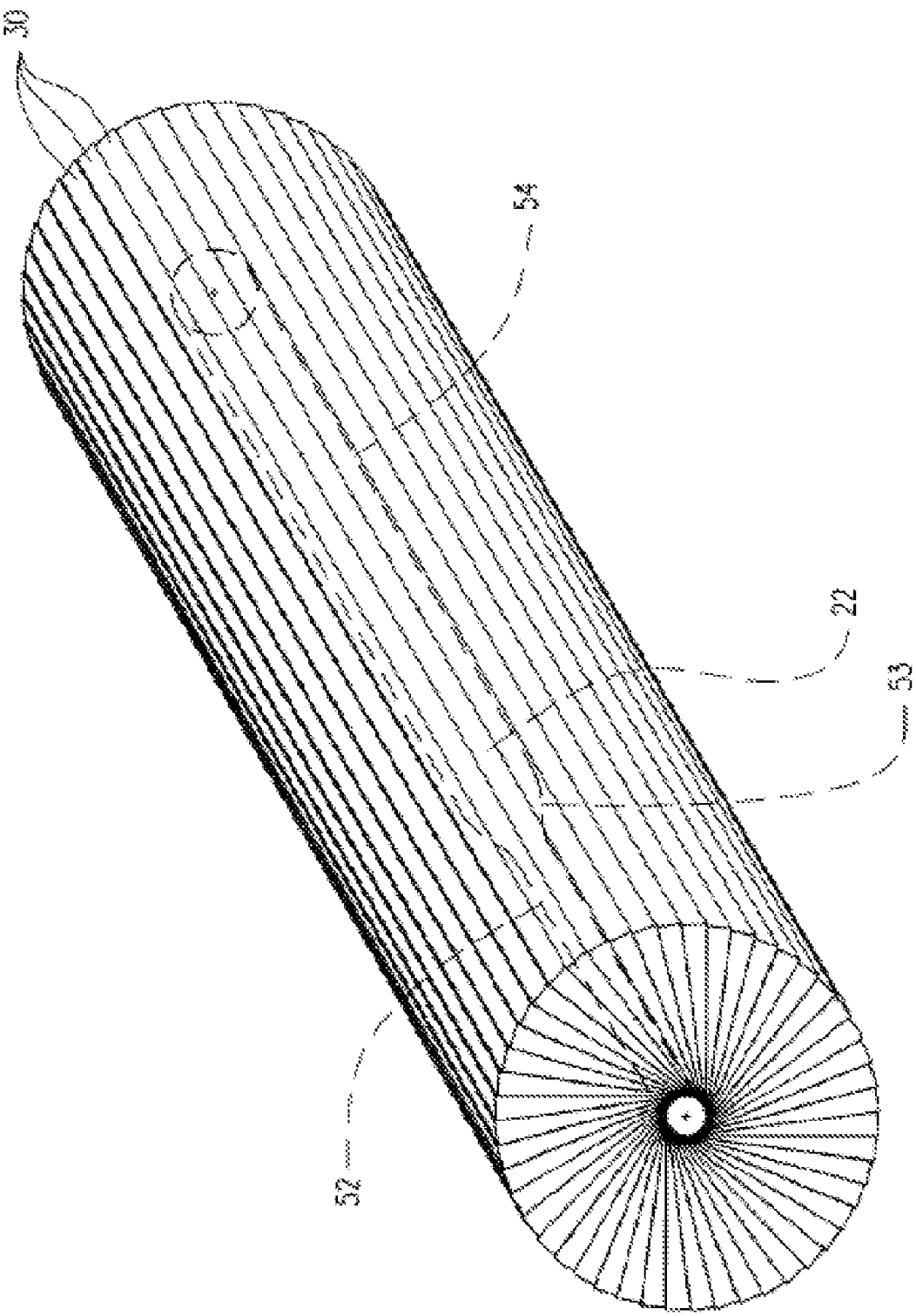
FIG. 37 shows an isometric view of an apparatus for reducing the size of an article having a chamber with portions of varying cross-section.
Figure 38:
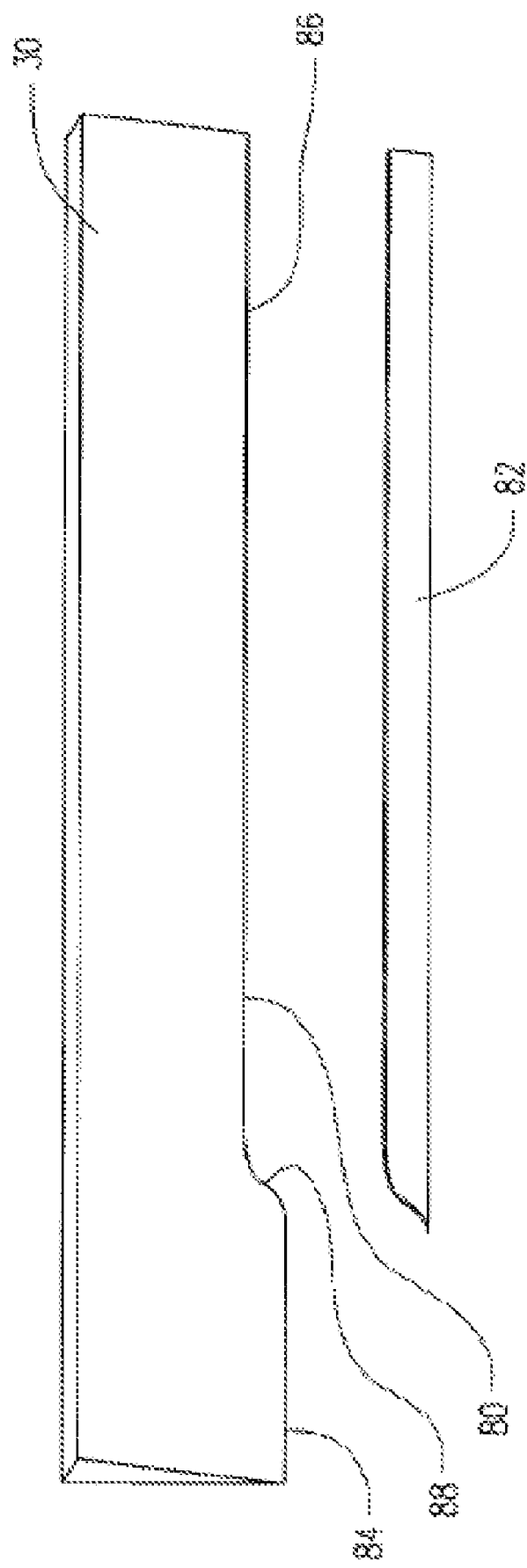
FIG. 38 shows an inventive die.
Figure 39:
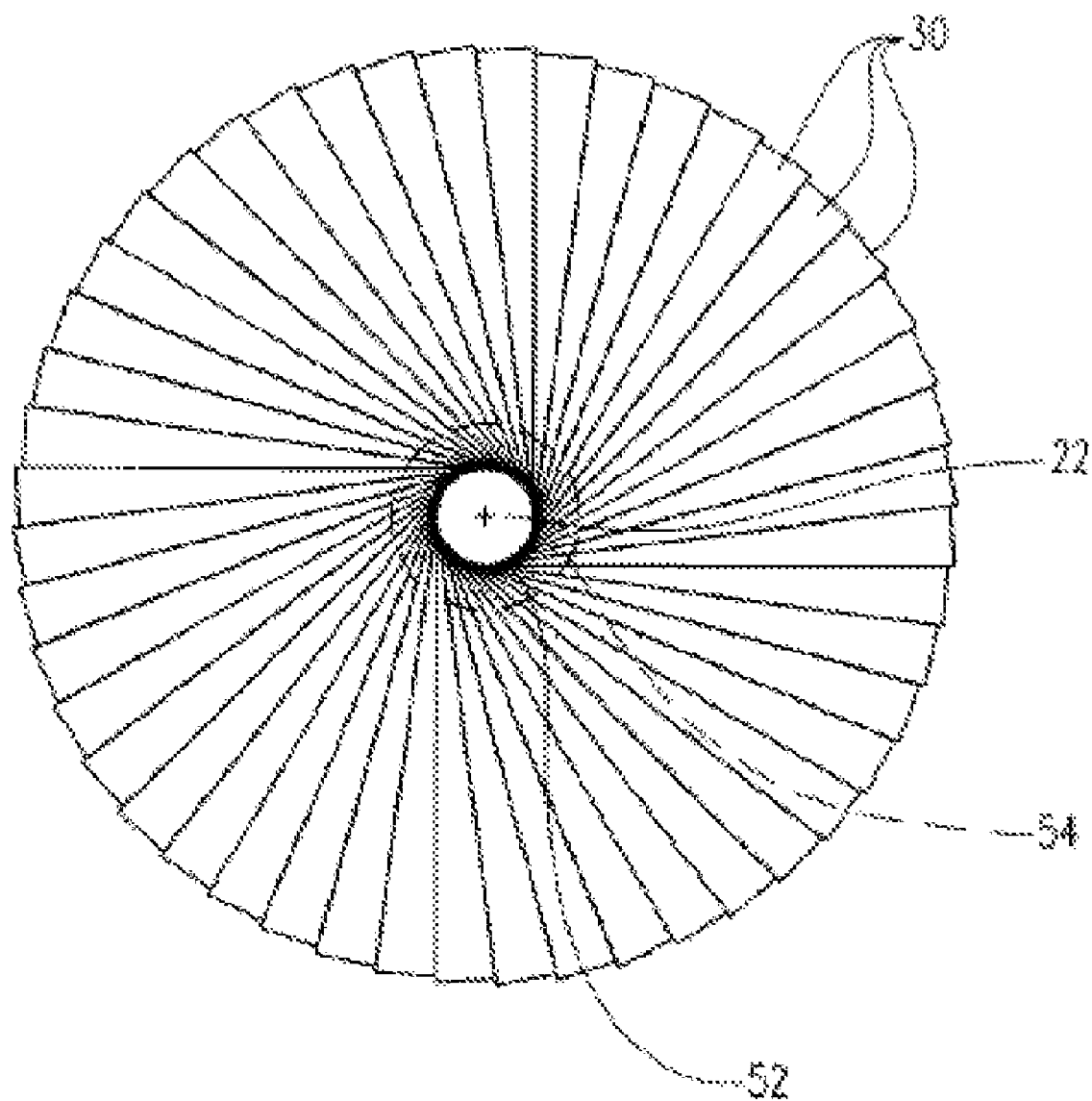
FIG. 39 shows an end view of an apparatus for reducing the size of an article having a chamber with portions of varying cross-section.

FIGS. 37-39 show an embodiment of an apparatus 20 having a chamber 22 with a varying cross-sectional area along its length.

The apparatus 20 may comprise a plurality of movable dies 30. All of the dies 30 may have the same physical shape. Each die 30 may be adjacent to at least one other die 30. Adjacent dies 30 may be slidably engaged with one another. The dies 30 may be arranged to form a chamber 22 that may run the length of the device. Wall surfaces or contacting surfaces 34 which bound the chamber 22 may comprise an iris 24.

FIG. 38 shows a single die 30 in greater detail. Each die 30 may include a contoured edge 80 and a contacting surface. A contoured edge 80 may impart changes in cross-sectional area to the chamber 22. A die 30 having a contoured edge 80 may be formed by beginning with a die having a constant cross-section along its length and selectively removing waste portions 82.

The shape of the chamber 22 is dependent upon the exact shape and number of dies 30 used in the apparatus. The shape of the chamber 22 is further dependent upon the shape of the contoured edges 80 of the dies. The number of sides of an iris 24 may be equal to the number of dies 30 that form the iris.

The embodiment of the apparatus shown in FIGS. 37-39 includes dies 30 wherein the contoured edge 80 comprises a leading portion 84 that is closest to the central longitudinal axis 26 of the apparatus 20, an offset portion 86 that is offset from the leading portion 84 and desirably parallel to the leading portion 84, and a transition portion 88 between the leading portion 84 and the offset portion 86. FIG. 37 shows the changes in the cross-section of the chamber 22 due to the contoured edges 80 of the dies 30. The leading portions 84 may impart a first diameter 52 to the chamber 22, the offset portions 86 may impart a second diameter 54 to the chamber 22 which may be larger than the first diameter 52, and the transition portions 88 may provide a taper 53 to the chamber 22 and a gradual transition from the first chamber diameter 52 to the second chamber diameter 54.

The apparatus 20 includes a larger number of dies 30 than some other embodiments described herein. A greater number of dies 30 may provide a greater number of contacting surfaces which contact an article placed within the chamber 22. A greater number of contacting surfaces may reduce the focal pressure placed upon the article and reduced the possibility of damaging the article or coatings applied to the article, such as drug coatings on a stent. A greater number of contacting surfaces may also provide for greater uniformity in the shape an article after the article has been reduced in size or otherwise operated upon by the apparatus.

Figure 40:
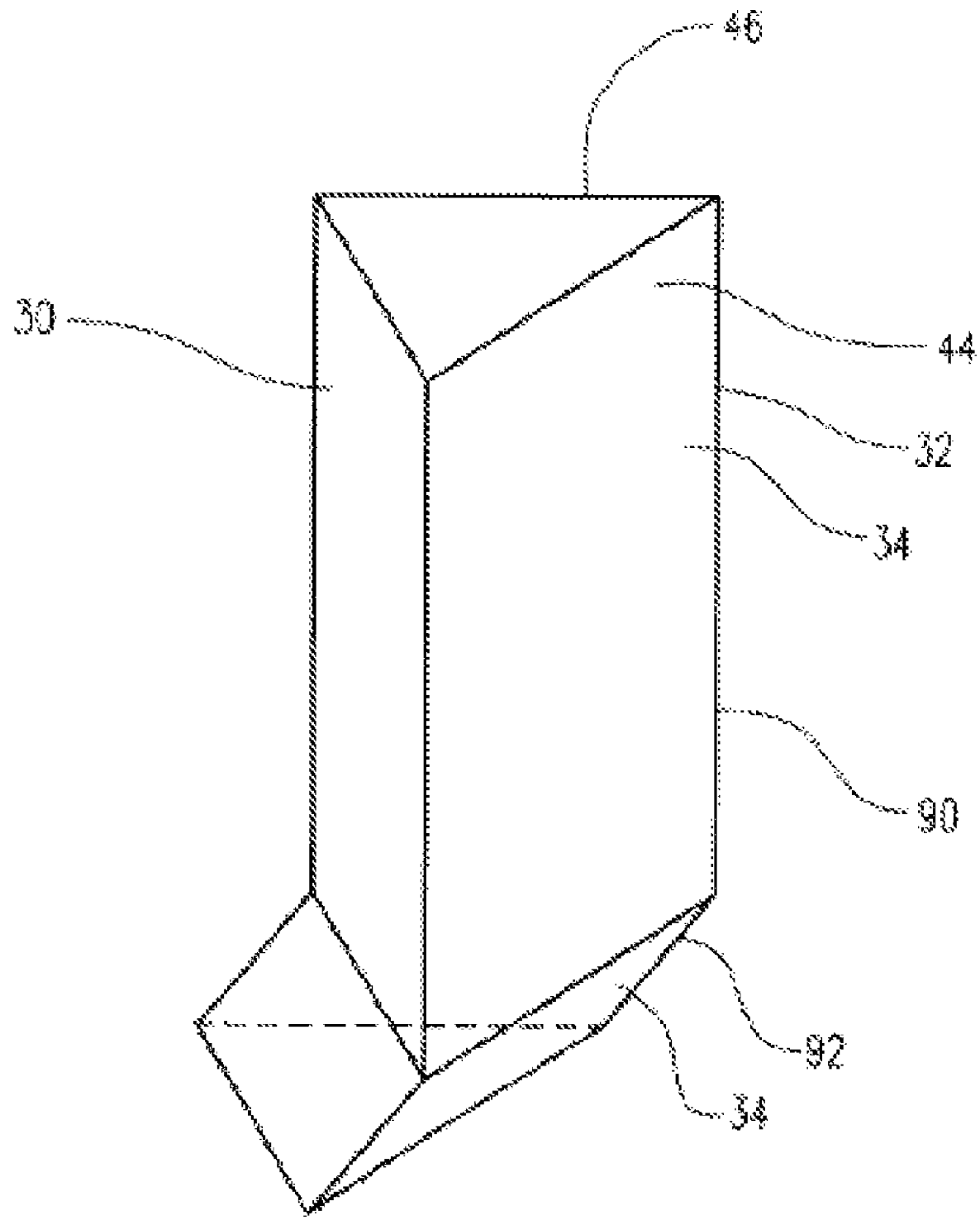
FIG. 40 shows an inventive die.

Another embodiment of an apparatus for shaping an article may be formed from a plurality of dies according to FIG. 40. Each die 30 may be adjacent to at least one other die 30. Adjacent dies 30 may be slidably engaged with one another. Desirably, a die 30 may be slidably engaged on a first side 44 with an adjacent die, and slidably engaged on a second side 46 with another adjacent die. The dies 30 may be arranged to form a chamber that may run the length of the device. Wall surface portions of the dies 30 which bound the chamber 22 may comprise an iris 24.

Each die 30 may include an edge 32 in proximity to the chamber and at least one contacting surface 34. The edge 32 may comprise a first portion 90 and a second portion 92. The first portion 90 may be parallel to the central longitudinal axis of the chamber. The second portion 92 may be oriented at an angle with respect to the first portion 90.

The shape of the chamber 22 is dependent upon the exact shape and number of dies 30 used in the apparatus. The shape of the chamber 22 is further dependent upon the angle between the first portion 90 and second portion 92 of the edge 32. The first portions 90 of dies 30 arranged to form a chamber may provide the chamber with a portion of constant cross-section along its length, while the second portions 92 may provide the chamber with a taper.

Figure 41:
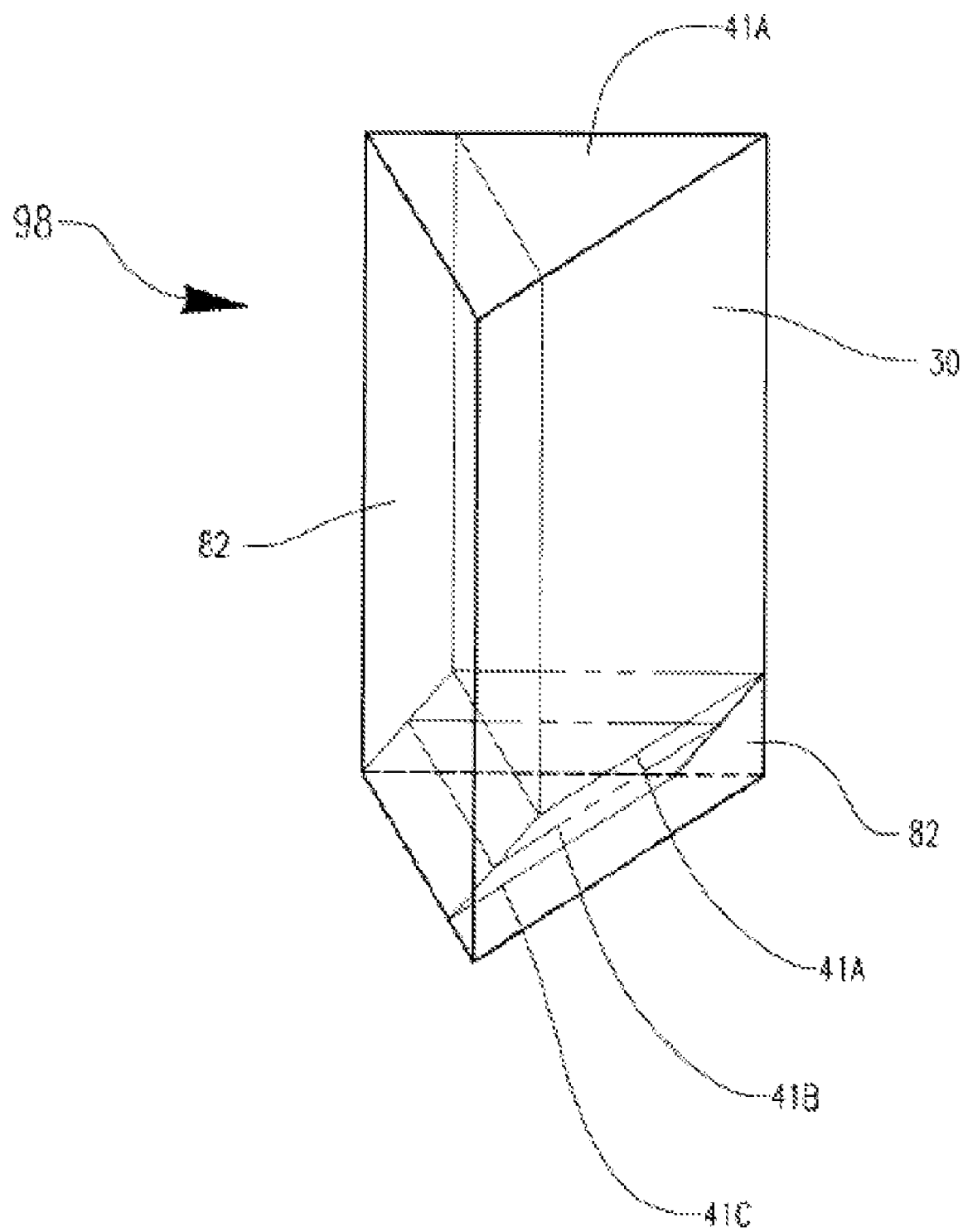
FIG. 41 shows a workpiece that may be modified to form the die of FIG. 40.
Figure 41A:
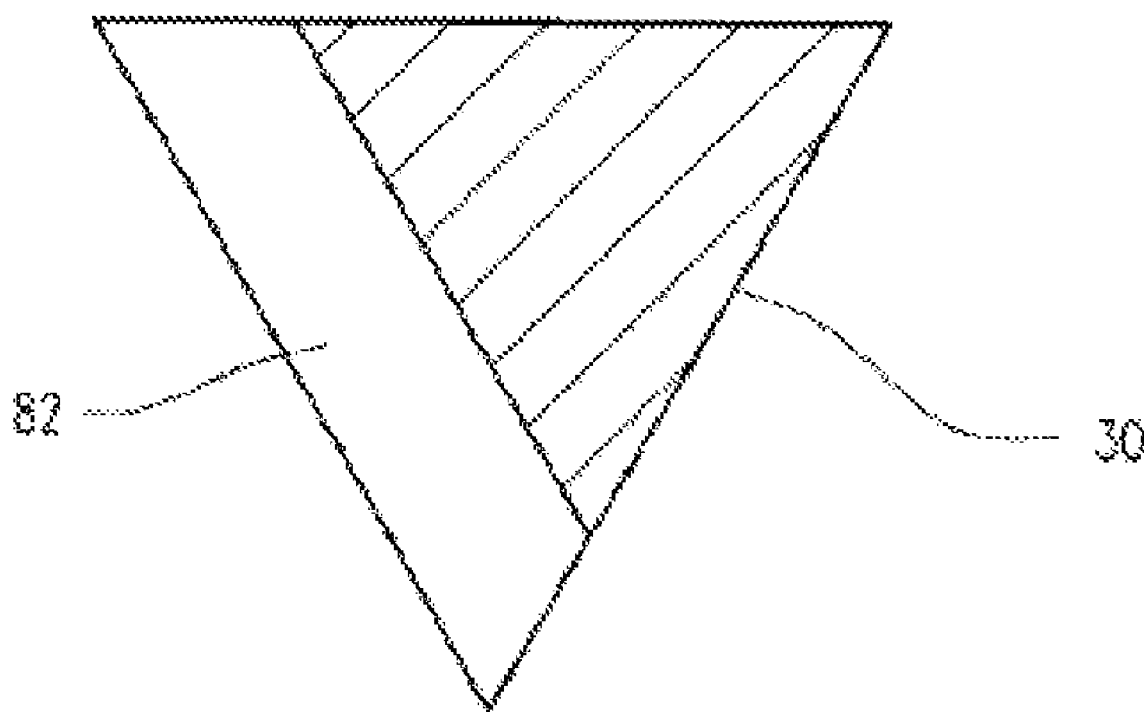
FIG. 41A is a sectional plane view taken from FIG. 41.
Figure 41B:
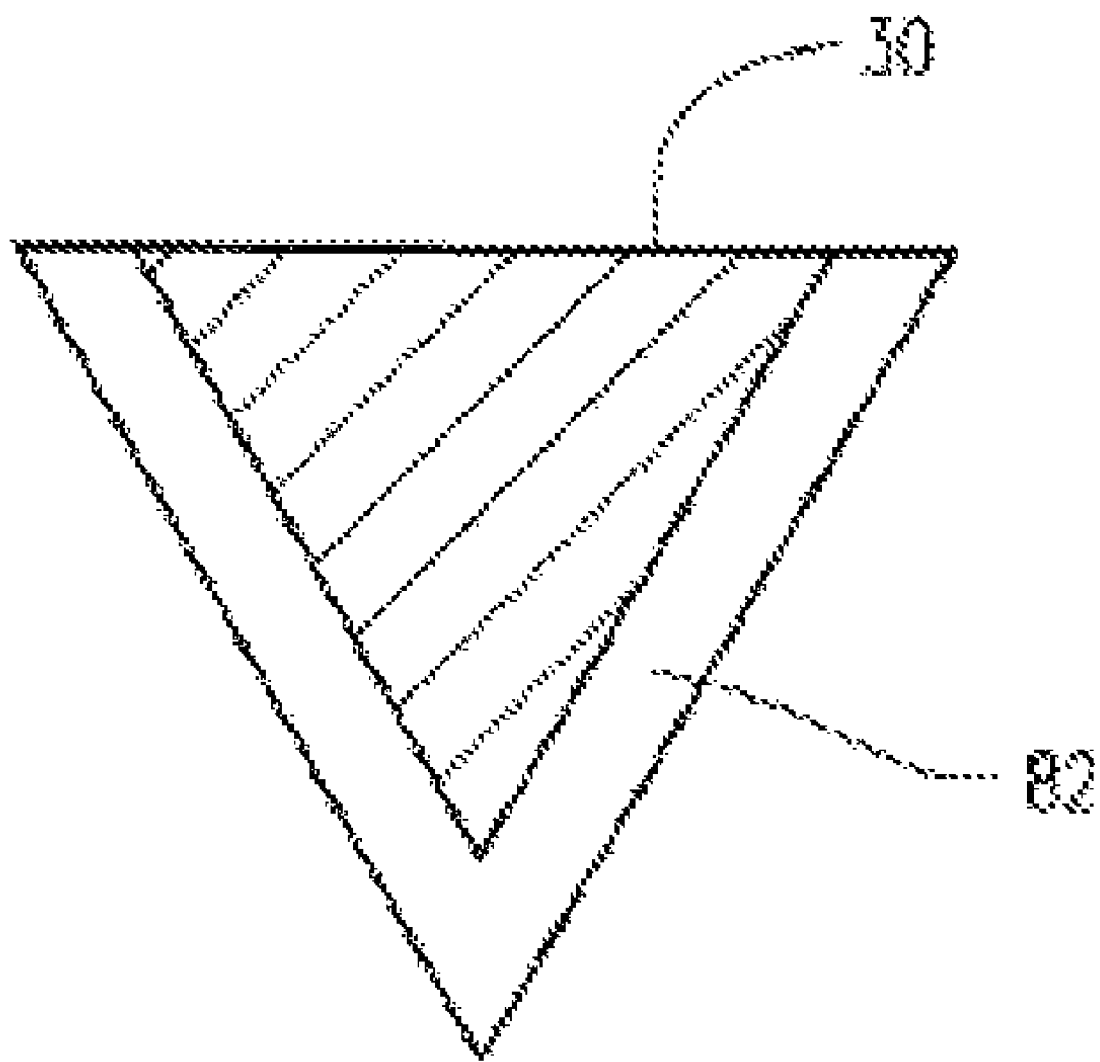
FIG. 41B is a sectional plane view taken from FIG. 41.
Figure 41C:
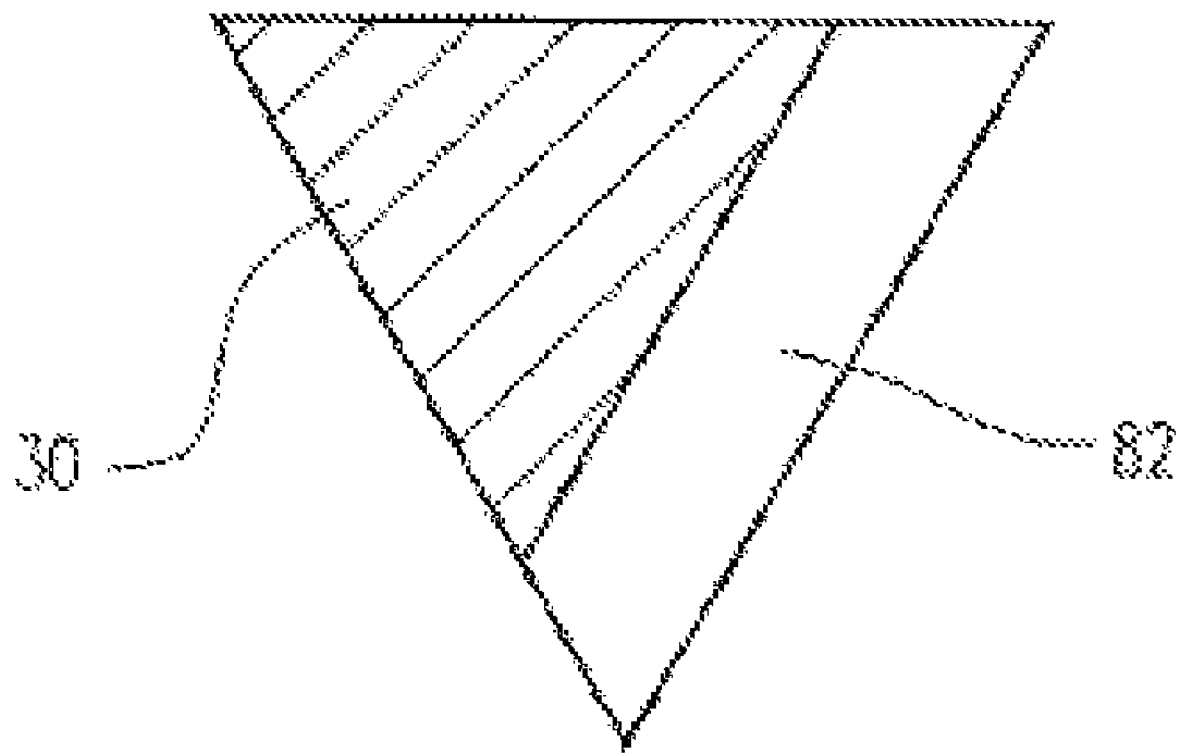
FIG. 41C is a sectional plane view taken from FIG. 41.
Figure 42:
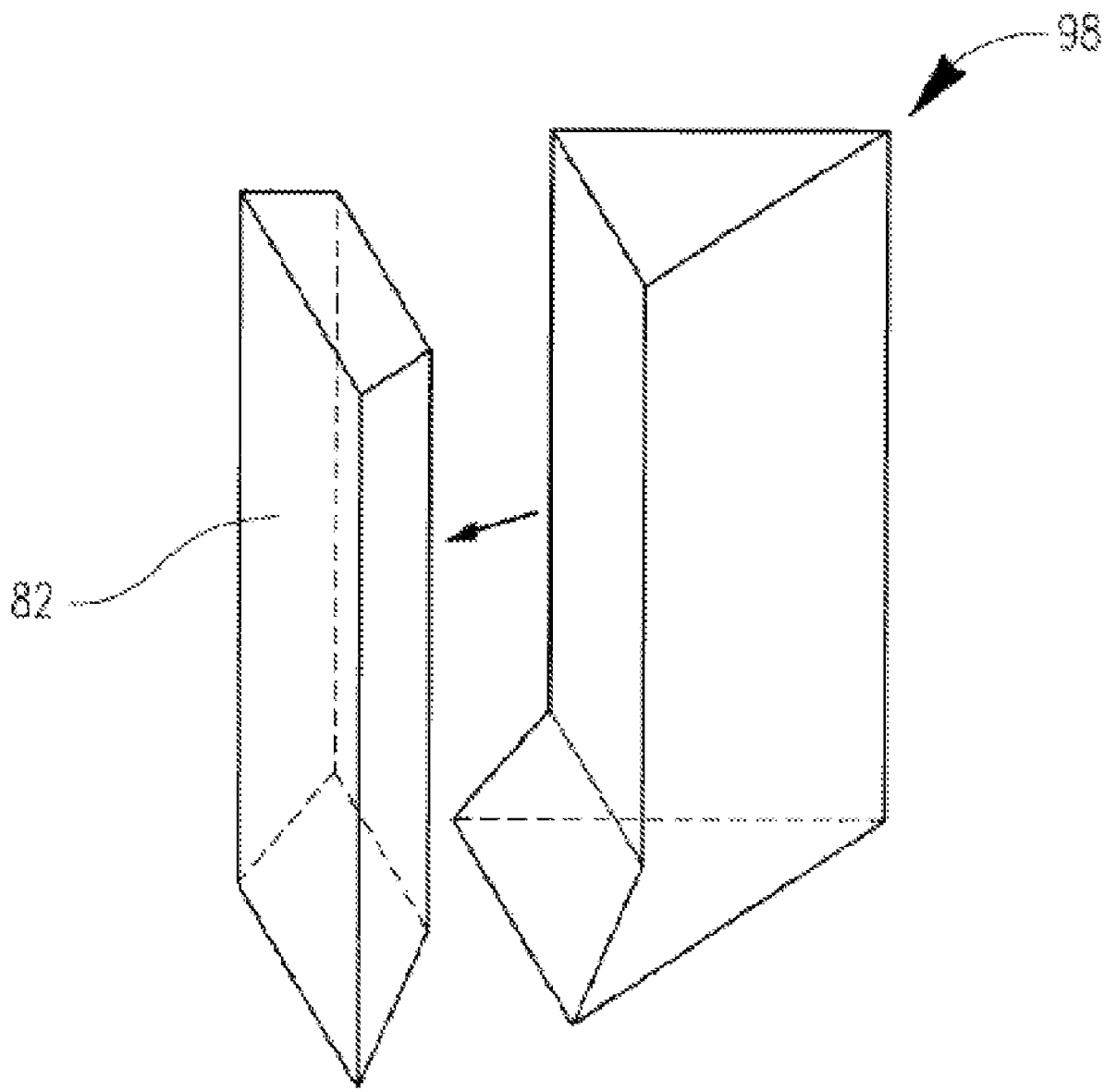
FIG. 42 shows a workpiece being modified to form the die of FIG. 40.
Figure 43:
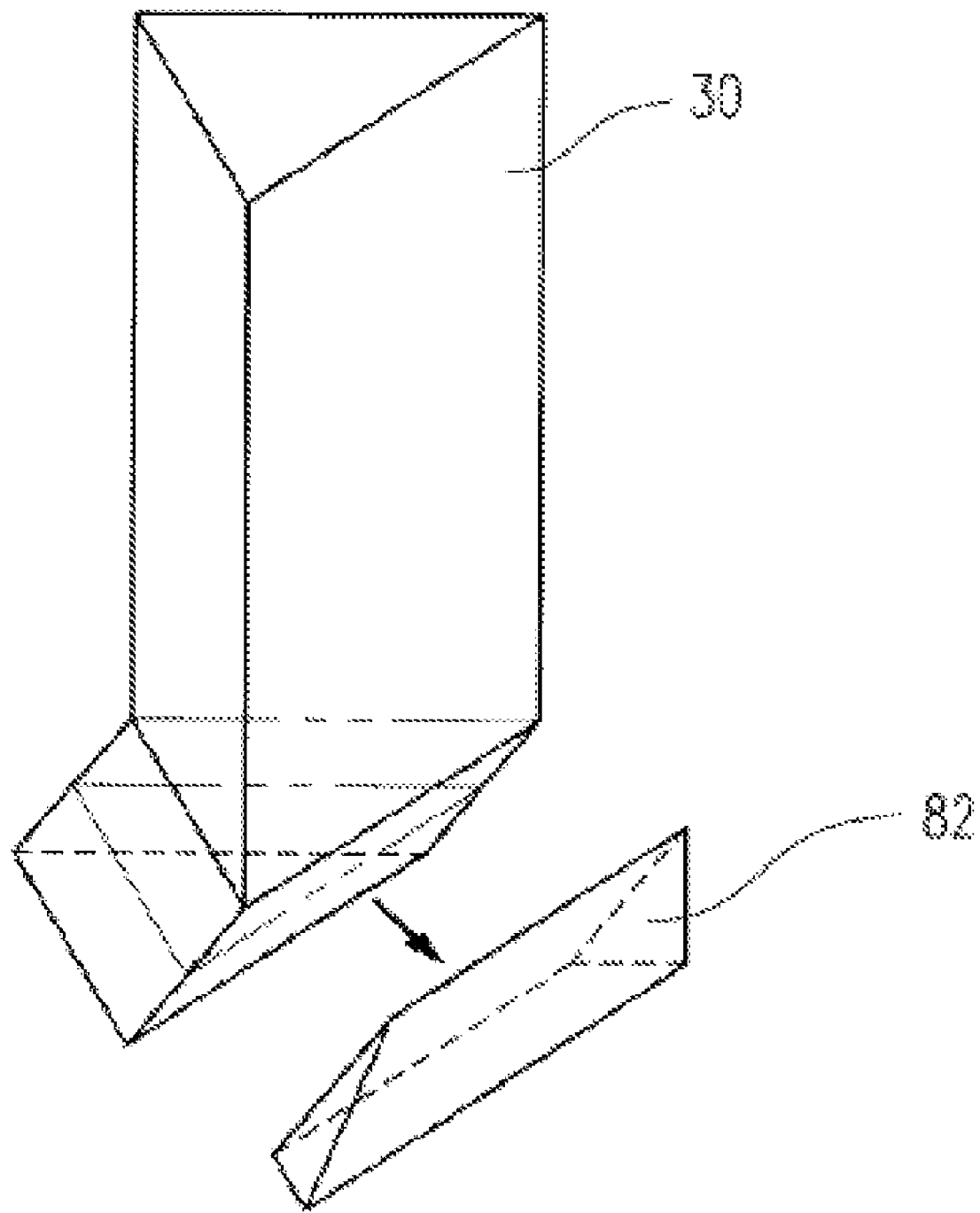
FIG. 43 shows a workpiece being modified to form the die of FIG. 40.

FIGS. 41-43 illustrate one method of forming the die 30 of FIG. 40. FIG. 41 shows a workpiece 98 that may be used to form a die 30. Waste portions 82 may be selectively removed to form the final die 30 shape. As indicated on FIG. 41, FIGS. 41A-41C show plane segments of the workpiece 98 indicating die portions 30 and waste portions 82. FIGS. 42 and 43 show the removal of waste portions 82 from the workpiece 98 to form the die 30.

Figure 44:
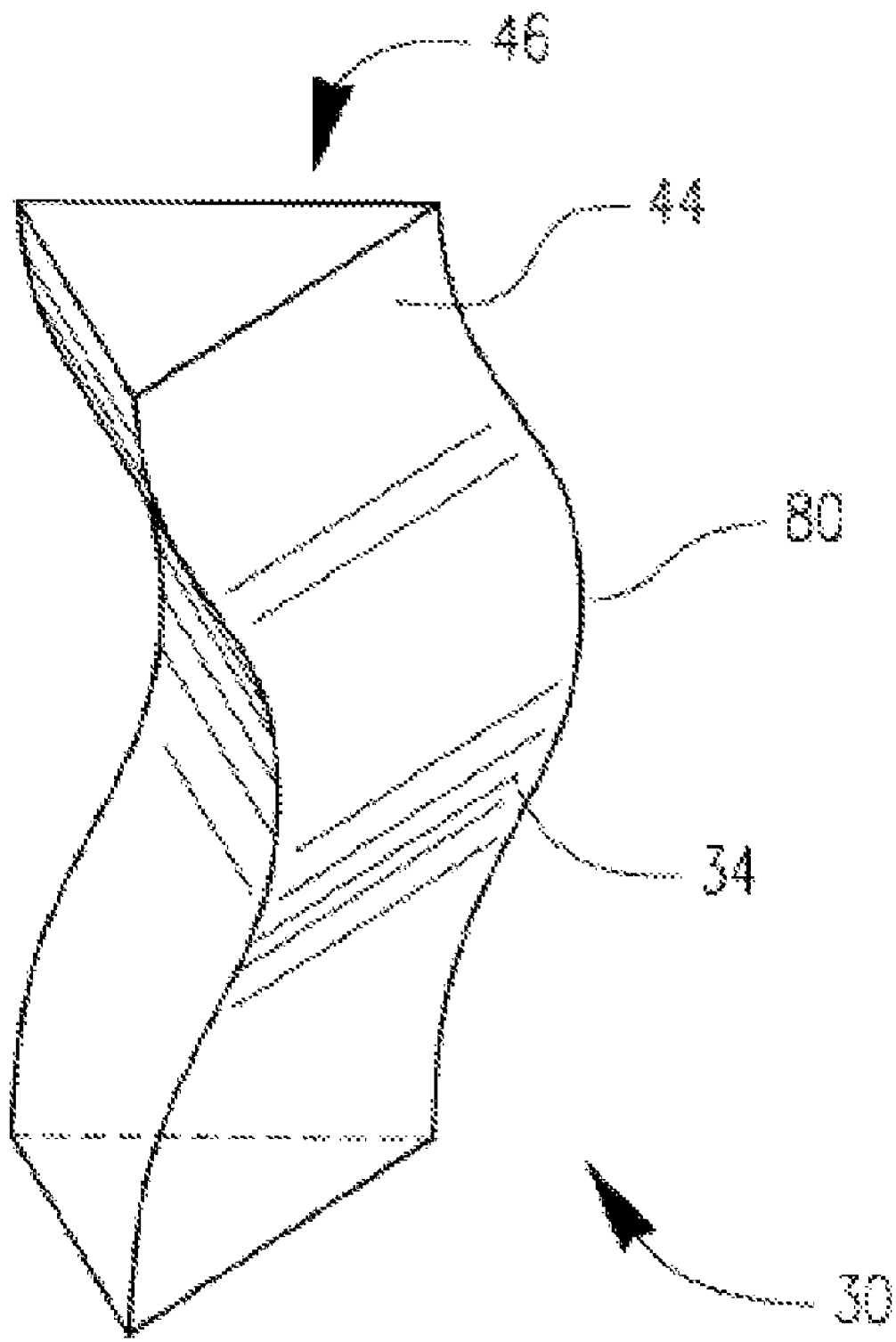
FIG. 44 shows an inventive die.

Another embodiment of an apparatus for shaping an article may be formed from a plurality of dies, at least one die having the shape of the die 30 shown in FIG. 44. Each die 30 may be adjacent to at least one other die 30. Adjacent dies 30 may be slidably engaged with one another. Desirably, a die 30 may be slidably engaged on a first side 44 with an adjacent die, and slidably engaged on a second side 46 with another adjacent die. The dies 30 may be arranged to form a chamber that may run the length of the device. Wall surface portions of the dies 30 which bound the chamber 22 may comprise an iris 24.

Each die 30 may include a contoured edge 80 in proximity to the chamber and at least one contacting surface 34. The contacting surface 34 may be non-planar or have curvature along its length. The curvature may be non-uniform along the length of the die 30. A contoured edge 80 may impart changes in cross-sectional area to the chamber 22. A contacting surface 34 having curvature along its length may provide a chamber having curvature along its length.

The shape of the chamber 22 is dependent upon the exact shape and number of dies 30 used in the apparatus. The shape of the chamber 22 is further dependent upon the shape of the contoured edges 80 of the dies. The number of sides of an iris 24 may be equal to the number of dies 30 that form the iris. Desirably, other dies used to form an apparatus may be shaped complimentary to the die 30 shown in FIG. 44 to form a chamber having an adjustable cross-sectional area.

Figure 45:
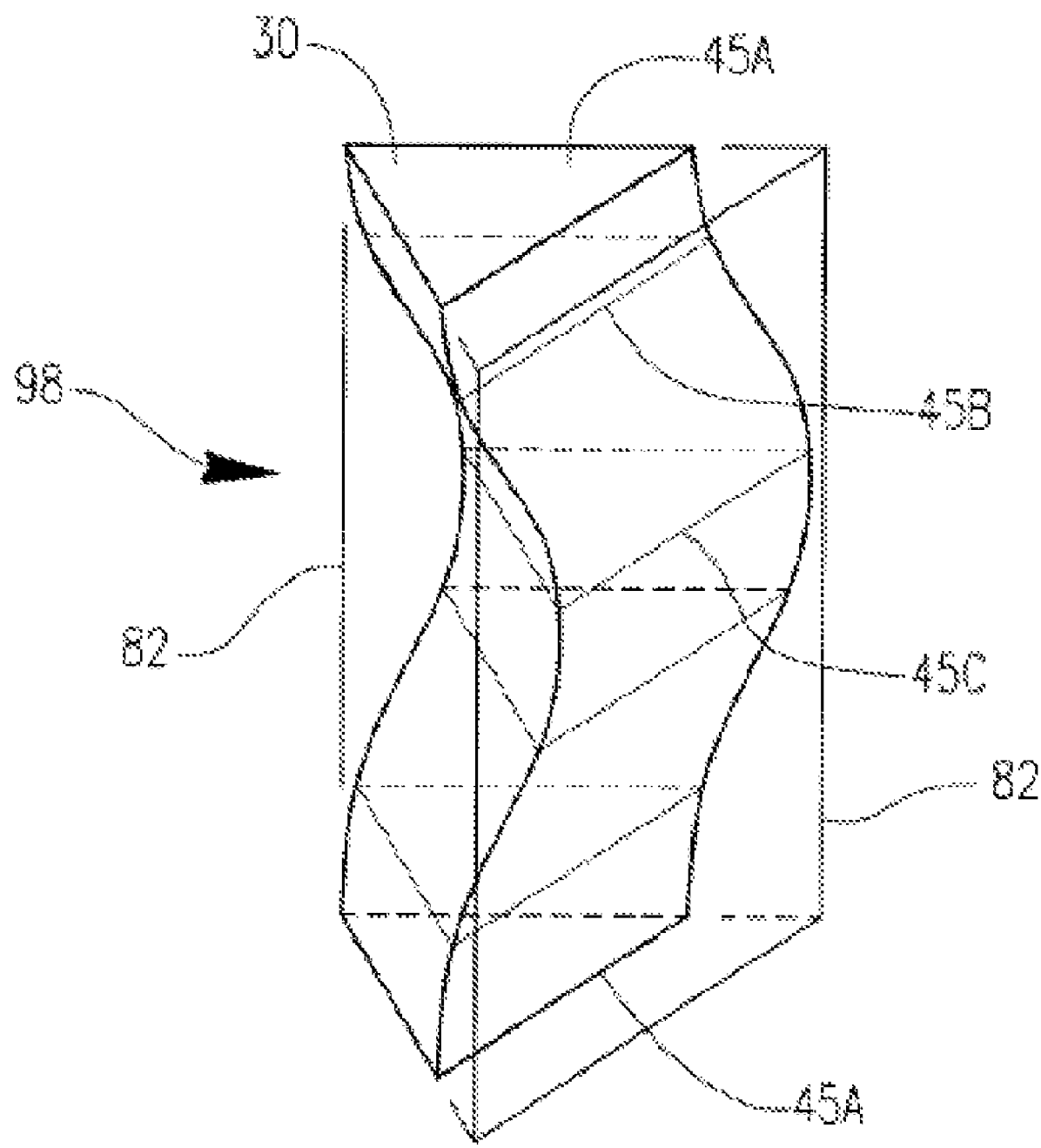
FIG. 45 shows a workpiece that may be modified to form the die of FIG. 44.
Figure 45A:
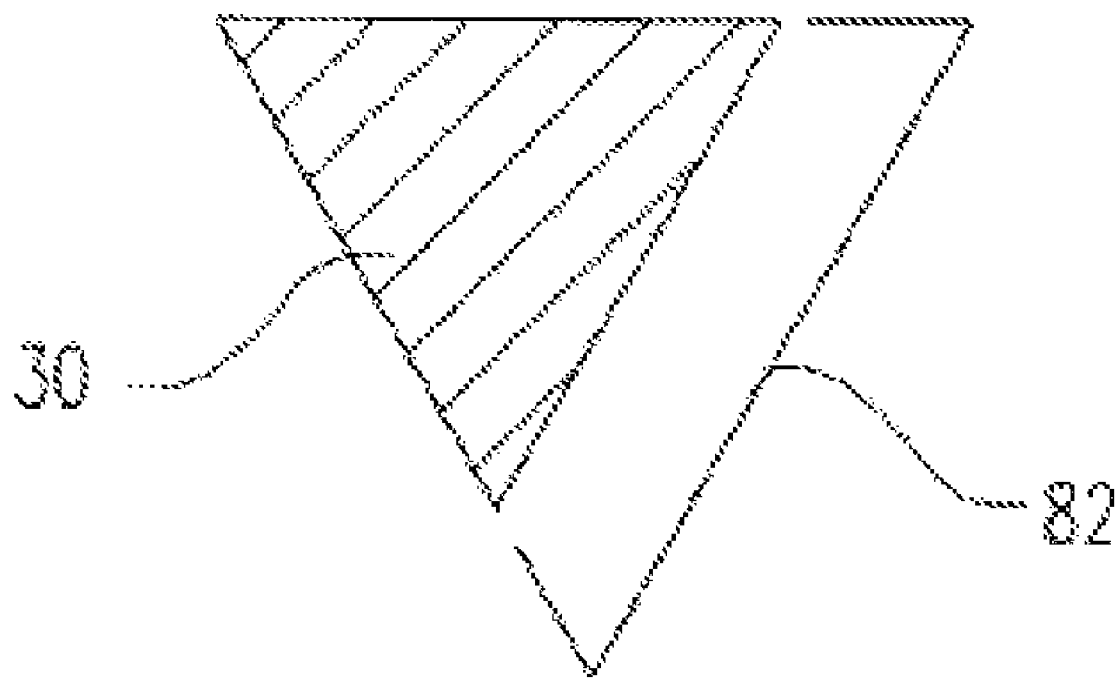
FIG. 45A is a sectional plane view taken from FIG. 44.
Figure 45B:
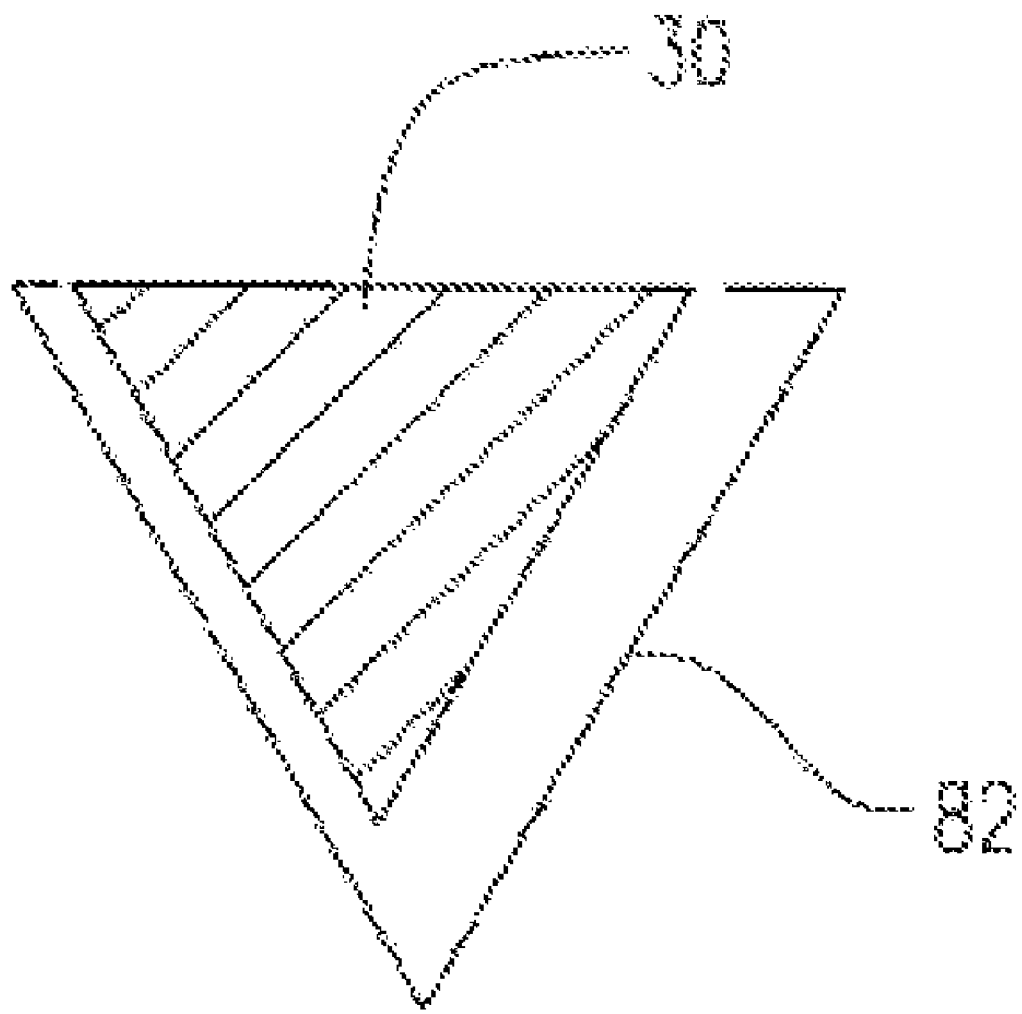
FIG. 45B is a sectional plane view taken from FIG. 44.
Figure 45C:
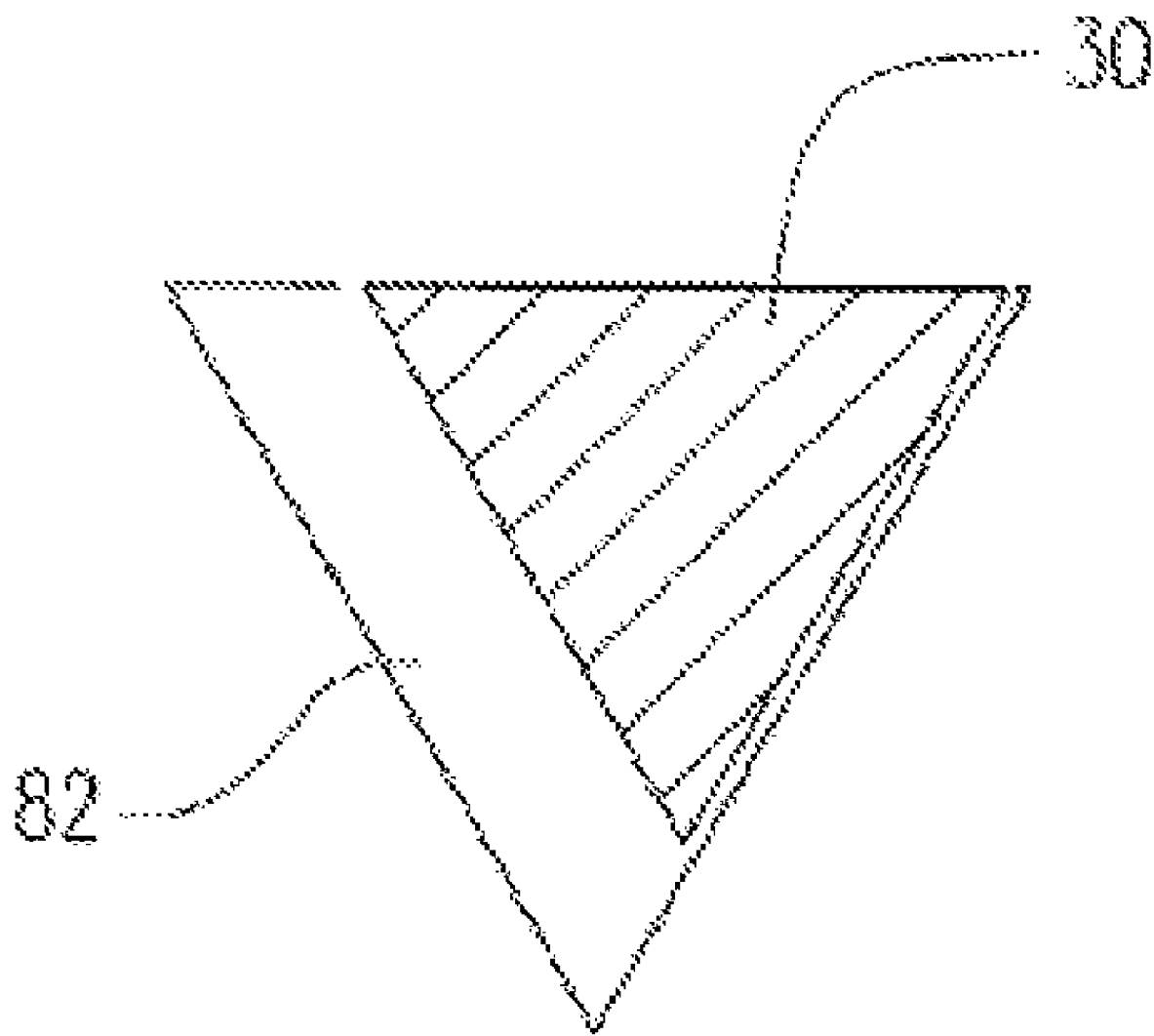
FIG. 45C is a sectional plane view taken from FIG. 44.
Figure 46:
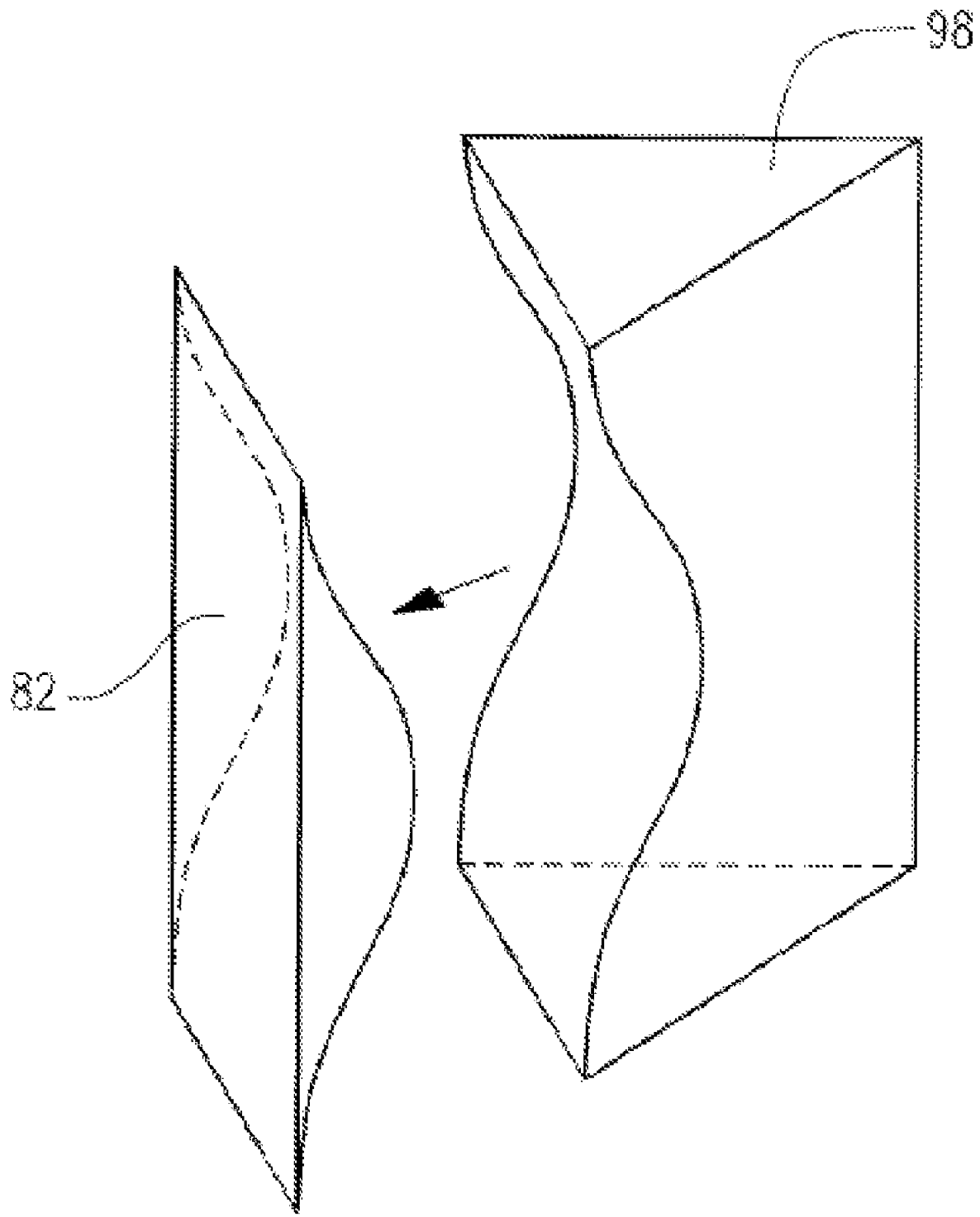
FIG. 46 shows a workpiece being modified to form the die of FIG. 44.
Figure 47:
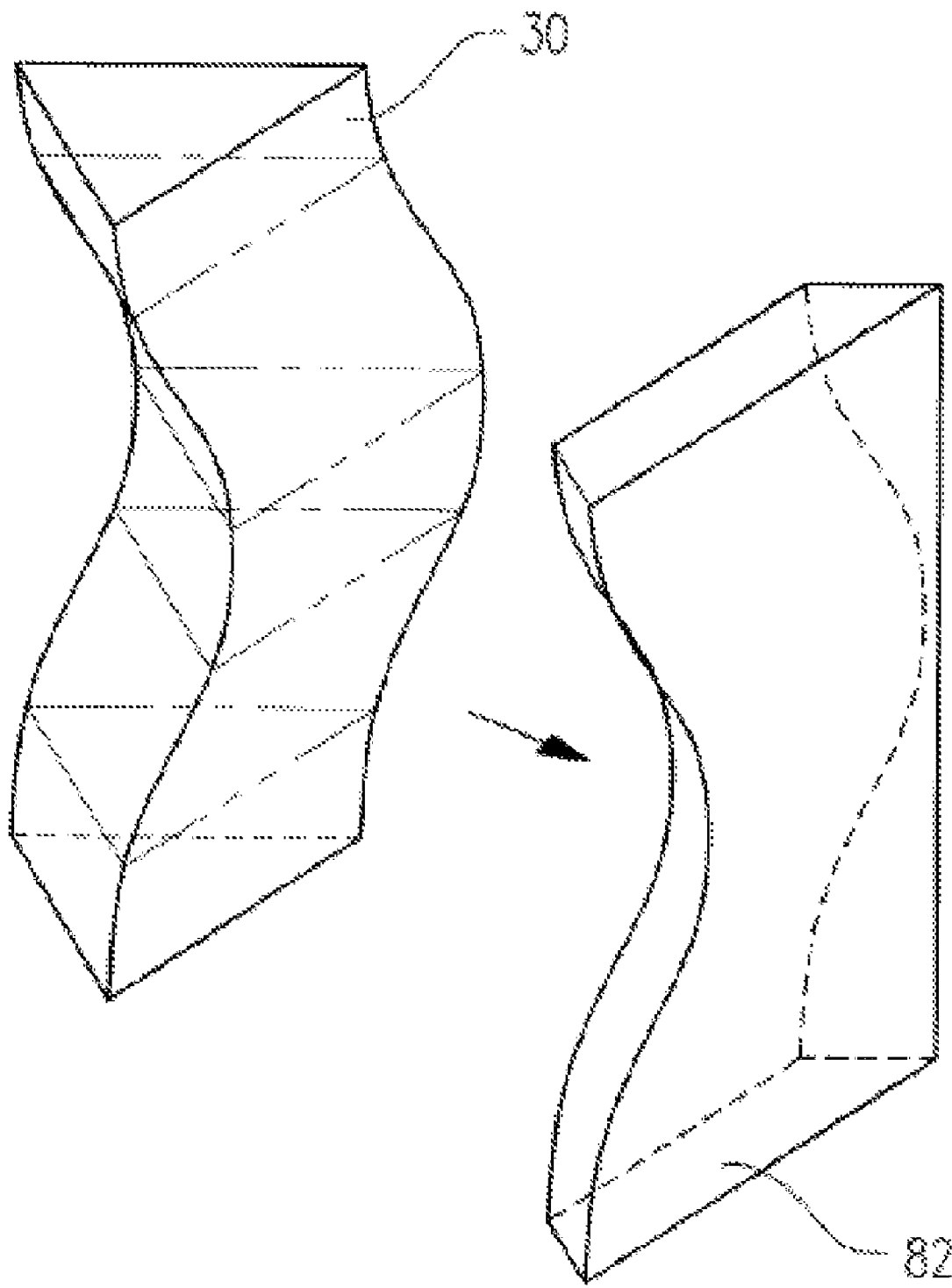
FIG. 47 shows a workpiece being modified to form the die of FIG. 44.

FIGS. 45-47 illustrate one method of forming the die 30 of FIG. 44. FIG. 45 shows a workpiece 98 that may be used to form a die 30. Waste portions 82 may be selectively removed to form the final die 30 shape. As indicated on FIG. 44, FIGS. 44A-44C show plane segments of the workpiece 98 indicating die portions 30 and waste portions 82. FIGS. 45 and 46 show the removal of waste portions 82 from the workpiece 98 to form the die 30.

Figure 48:
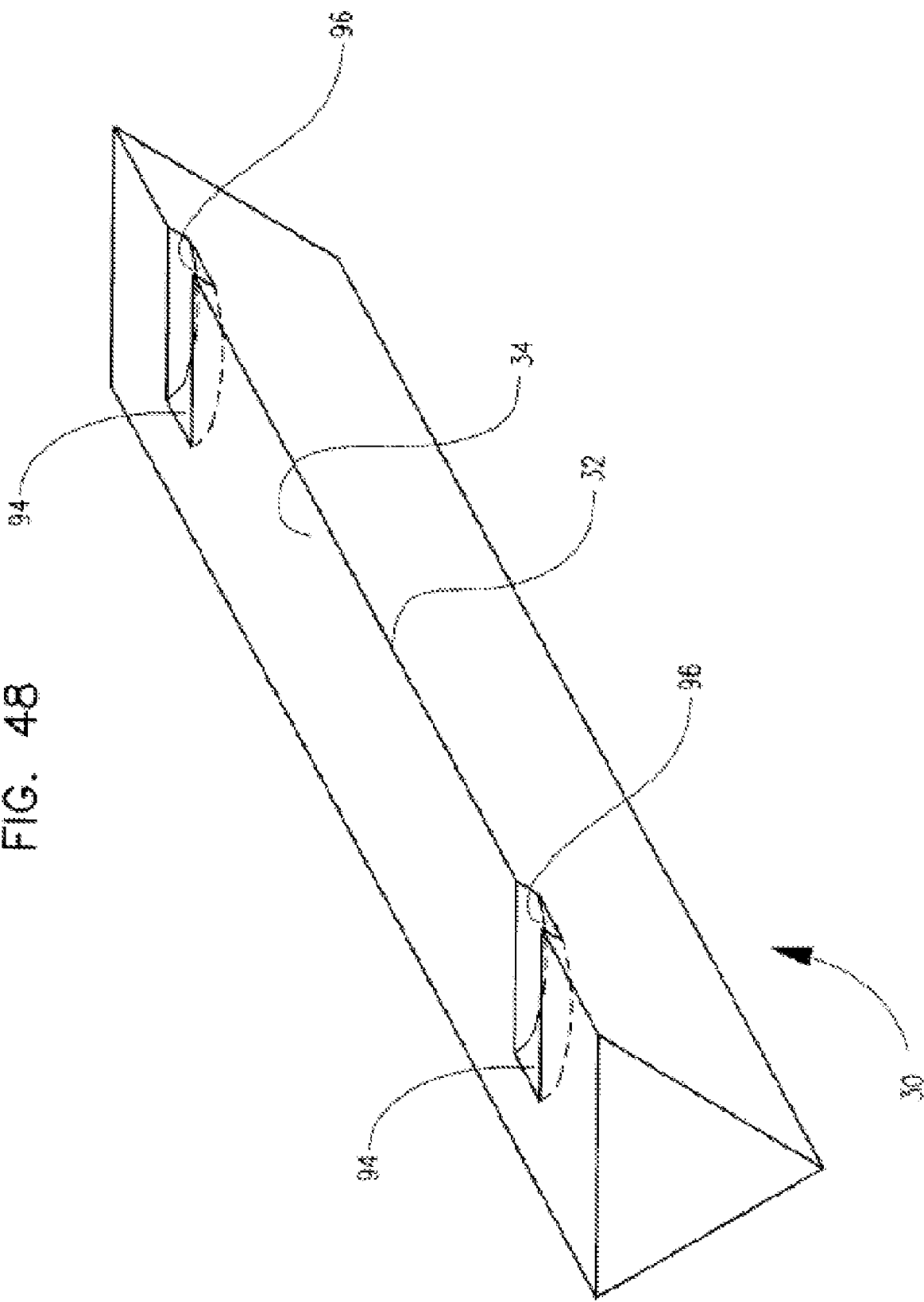
FIG. 48 shows an inventive die.
Figure 49:
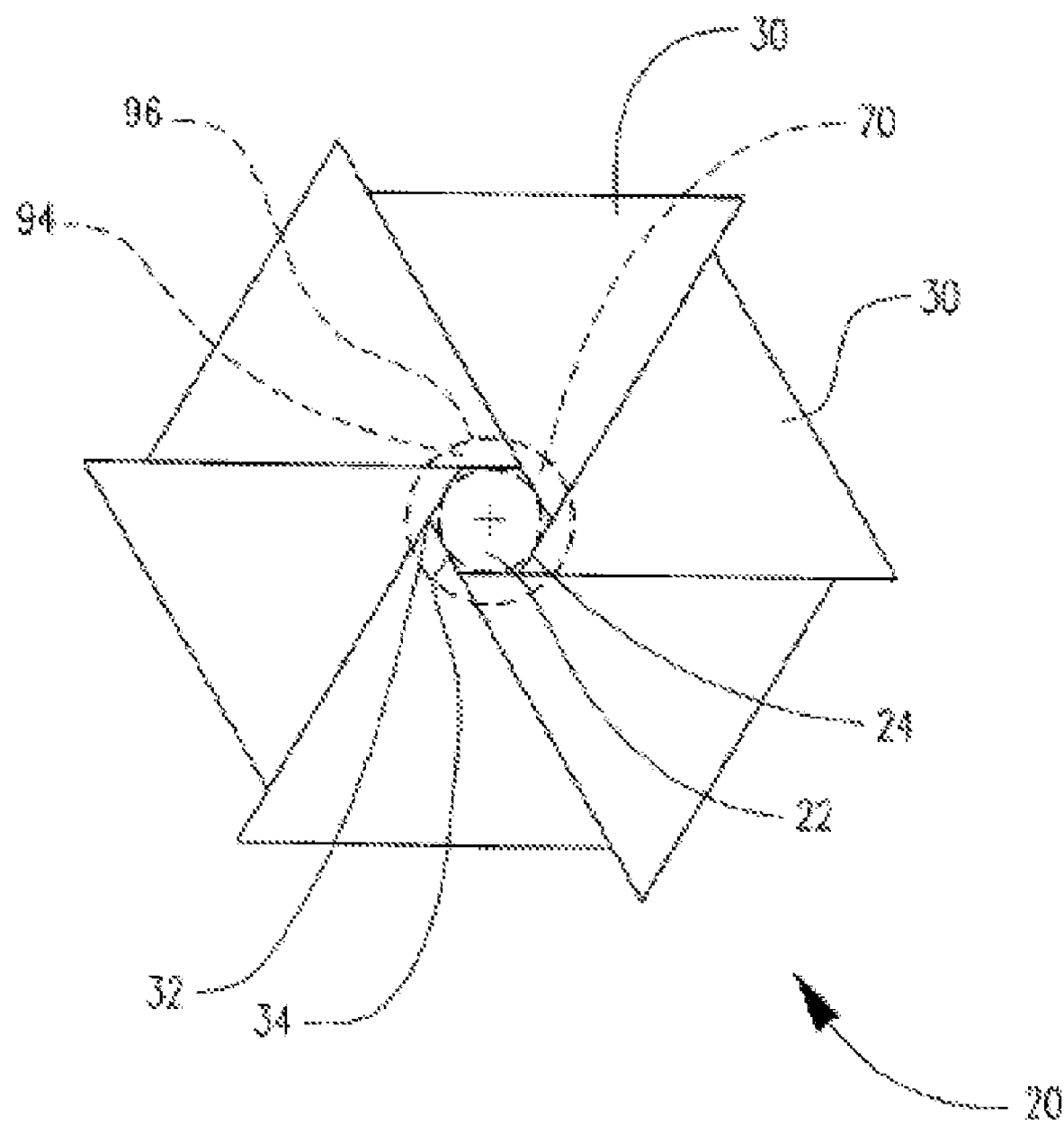
FIG. 49 shows an end view of an apparatus for reducing the size of an article having a chamber with portions of a first size and portions of a second size.
Figure 50:
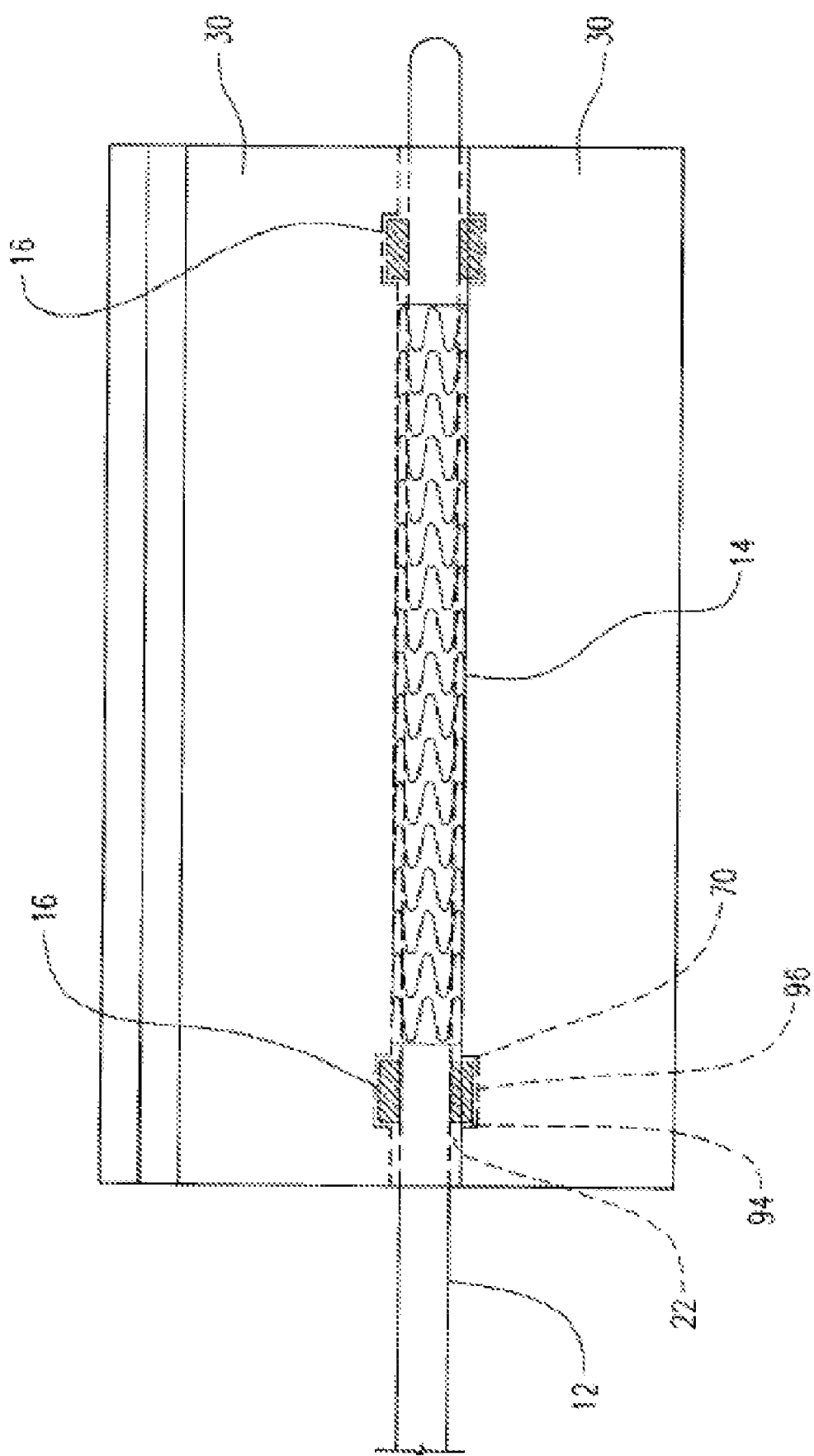
FIG. 50 shows a side view of an apparatus for reducing the size of an article having a chamber with portions of a first size and portions of a second size.

FIGS. 48-50 show another embodiment of an apparatus 20 for shaping an article which may comprise a plurality of dies 30. Each die 30 may be adjacent to at least one other die 30. Adjacent dies 30 may be slidably engaged with one another along an engagement plane. The dies 30 may be arranged to form a chamber 22 that may run the length of the device. Wall surfaces or contacting surfaces 34 which bound the chamber 22 may comprise an iris 24. The exact shape of the iris 24 is dependent upon the shape, number and arrangement of the dies 30.

Each die 30 may include an edge 32 and at least one contacting surface 34. A contacting surface 34 may contact and reduce the size of an article placed within the chamber 22. Each die 30 may include at least one notch 94 in a contacting surface 34. A notch 94 may include an additional contacting surface 96, which may be curved.

Notched portions 94 may provide the chamber 22 with portions of increased cross-sectional area 70. The shape of a notch 94 may be selected to provide the portions of increased cross-sectional area 70 with a predetermined iris 24 shape when nominal portions of the chamber 22 reach a predetermined size. For example, as shown in FIG. 49, notches 94 in the dies 30 form a portion of increased cross-sectional area 70 having a circular cross-section when nominal portions of the chamber 22 reach the dimensions shown.

An apparatus 20 having a chamber 22 having portions of increased cross-sectional area 70 may be used to reduce the size of first and second articles placed within the chamber. The first and second articles may have different diameters.

FIG. 50 shows an apparatus 20 having a chamber 22 having portions of increased cross-sectional area 70, a catheter 12 disposed within the chamber, a first article 14 comprising a stent disposed within a nominal portion of the chamber 22 and second articles 16 comprising radiopaque marker bands disposed within chamber portions of increased cross-sectional area 70. The apparatus 20 may be used to simultaneously reduce the size of the stent 14 about the catheter 12 and crimp the marker bands 16 to the catheter 12. Desirably, the notches 94 of the dies 30 may be shaped to form portions of increased cross-sectional area 70 having circular cross-sections when the stent 14 reaches its fully reduced diameter.

A reduction in size of a stent or other medical device may occur as part of a precrimping step or it may occur as part of crimping a stent onto a catheter and desirably, onto a balloon disposed about a catheter. The apparatus 20 may be used for manipulating a medical device and more specifically for applying a radial inward force to a medical device.

Figure 51:
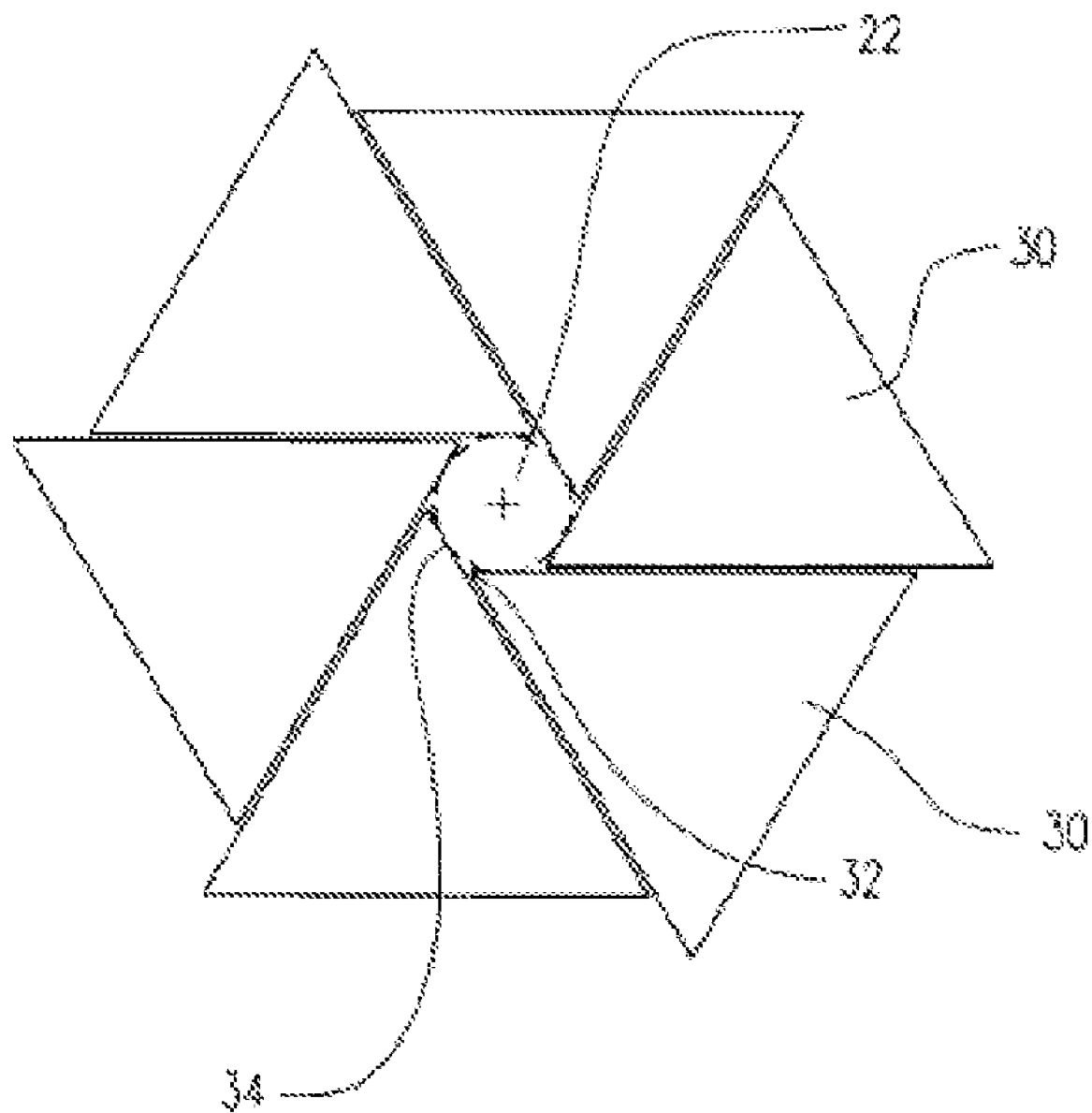
FIG. 51 is an end view of an apparatus for reducing the size of an article.

Although various embodiments of the invention described herein have included adjacent dies which contact one another or are slidably engaged with one another, adjacent dies are not required to be in contact with other dies. For example, FIG. 51 shows an embodiment wherein adjacent dies do not contact one another. It is also contemplated that in some embodiments, some dies may contact other dies, while some dies will not contact any other dies.

Although various embodiments of the invention described herein have included an even number of dies, additional embodiments are contemplated that include an odd number of dies. Further, the number of dies which may be used to form a chamber may be adjusted as desired. Any number of dies sufficient to form a chamber and reduce the size of an article placed within the chamber may be used to form various embodiments of the invention.

Figure 52:
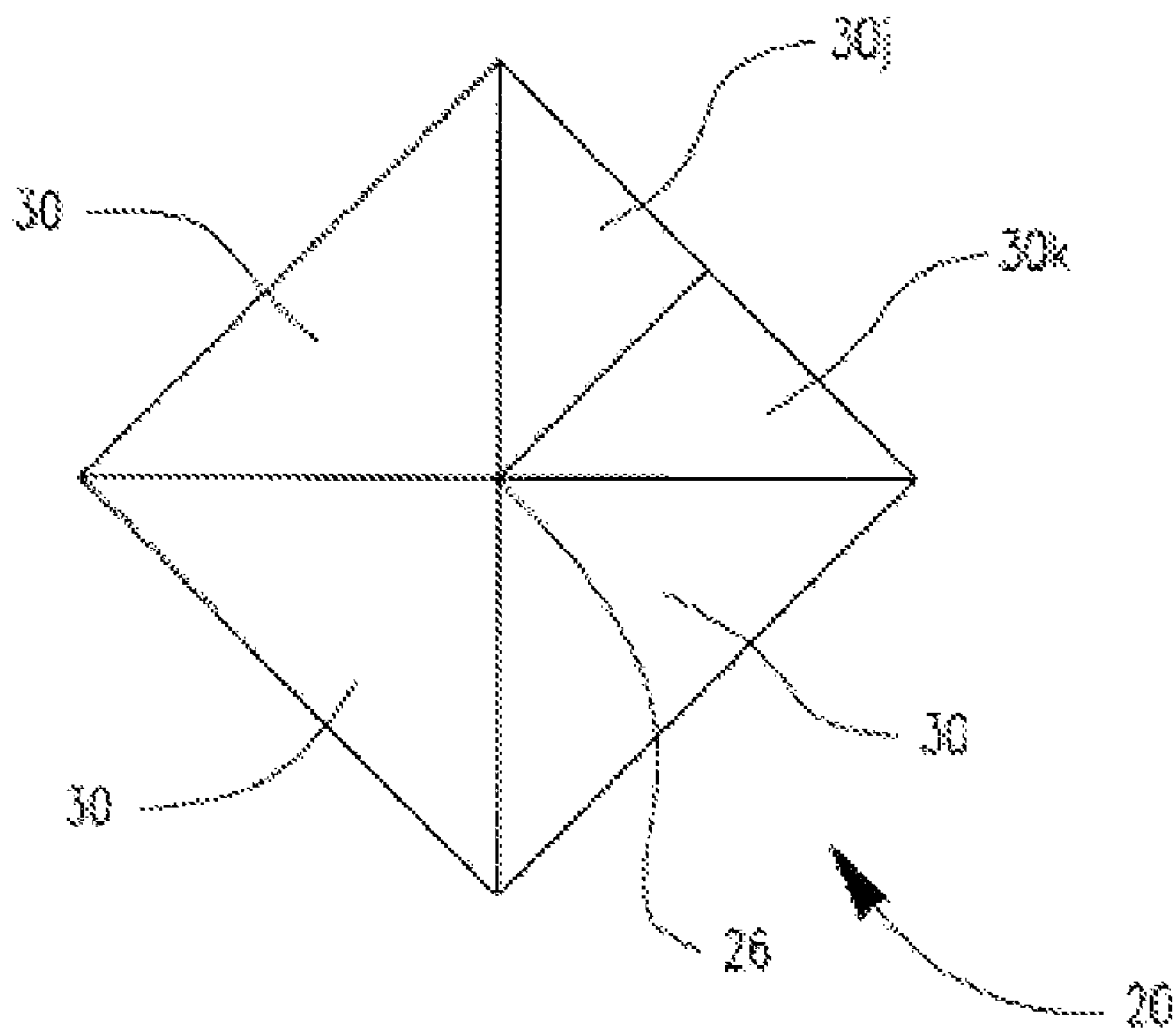
FIG. 52 is an end view of an apparatus for reducing the size of an article having an odd number of dies in a closed configuration.
Figure 53:
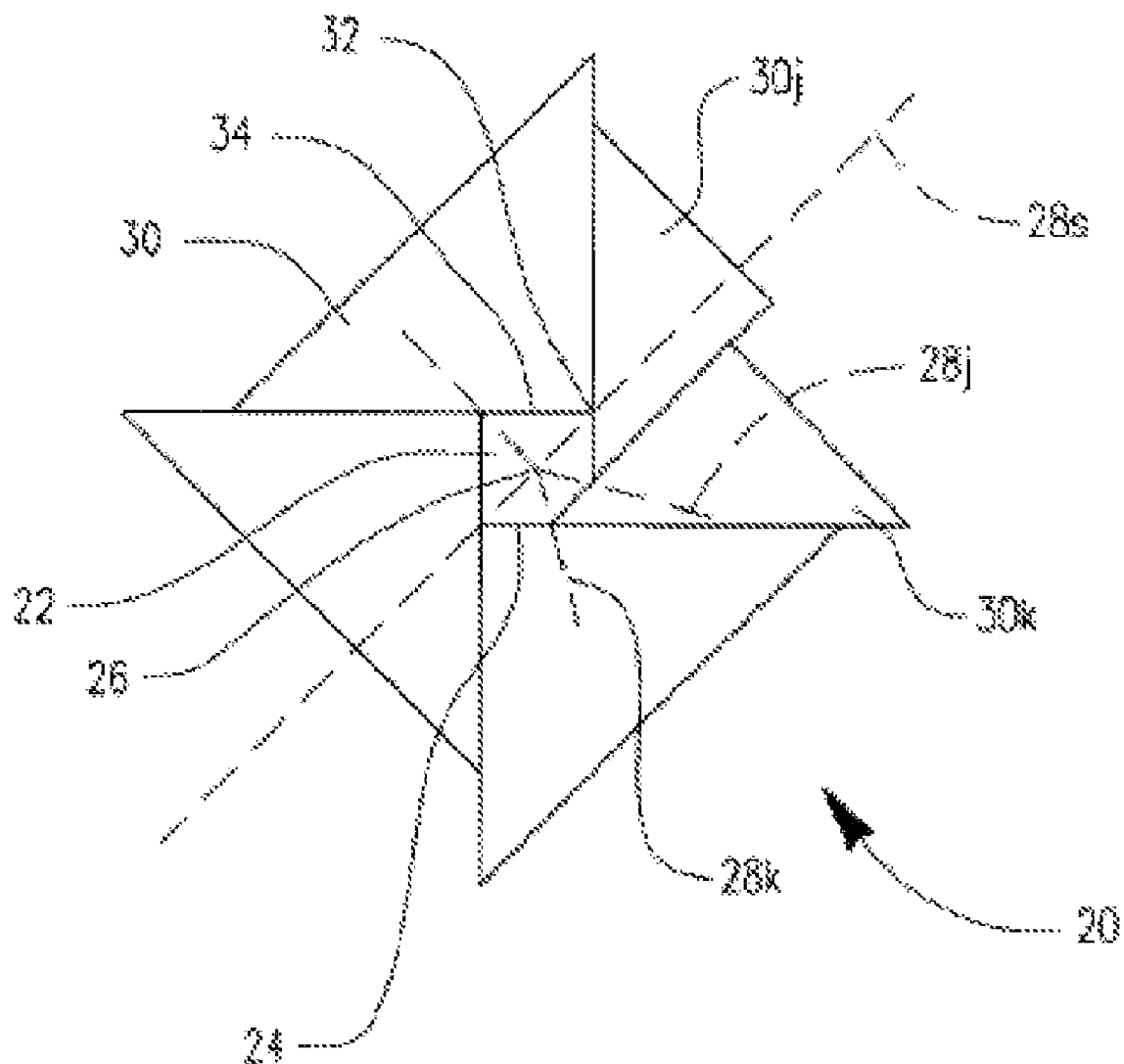
FIG. 53 is an end view of an apparatus for reducing the size of an article having an odd number of dies in an open configuration.
Figure 54:
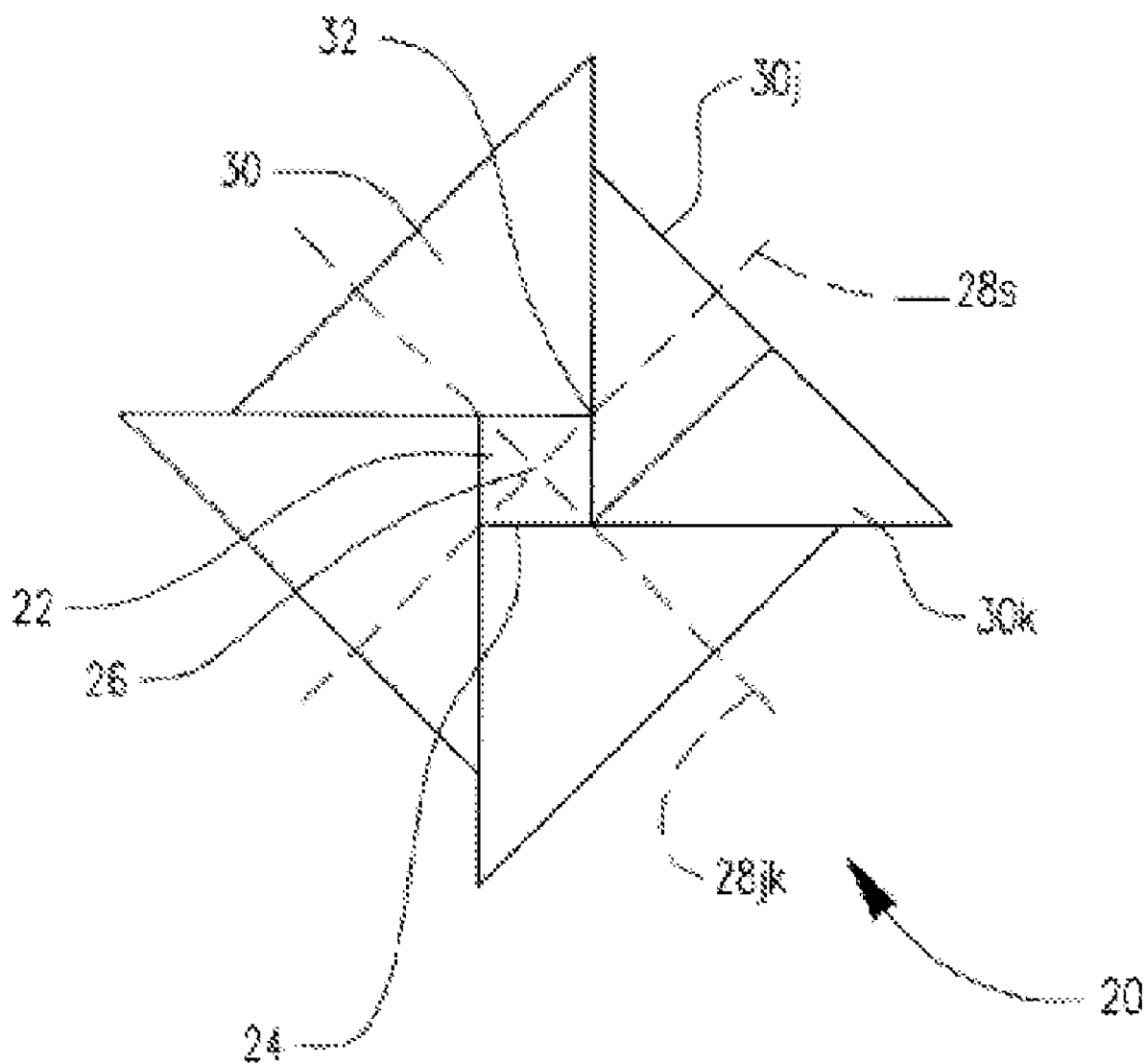
FIG. 54 is an end view of an apparatus for reducing the size of an article having an odd number of dies in another open configuration.
Figure 55:
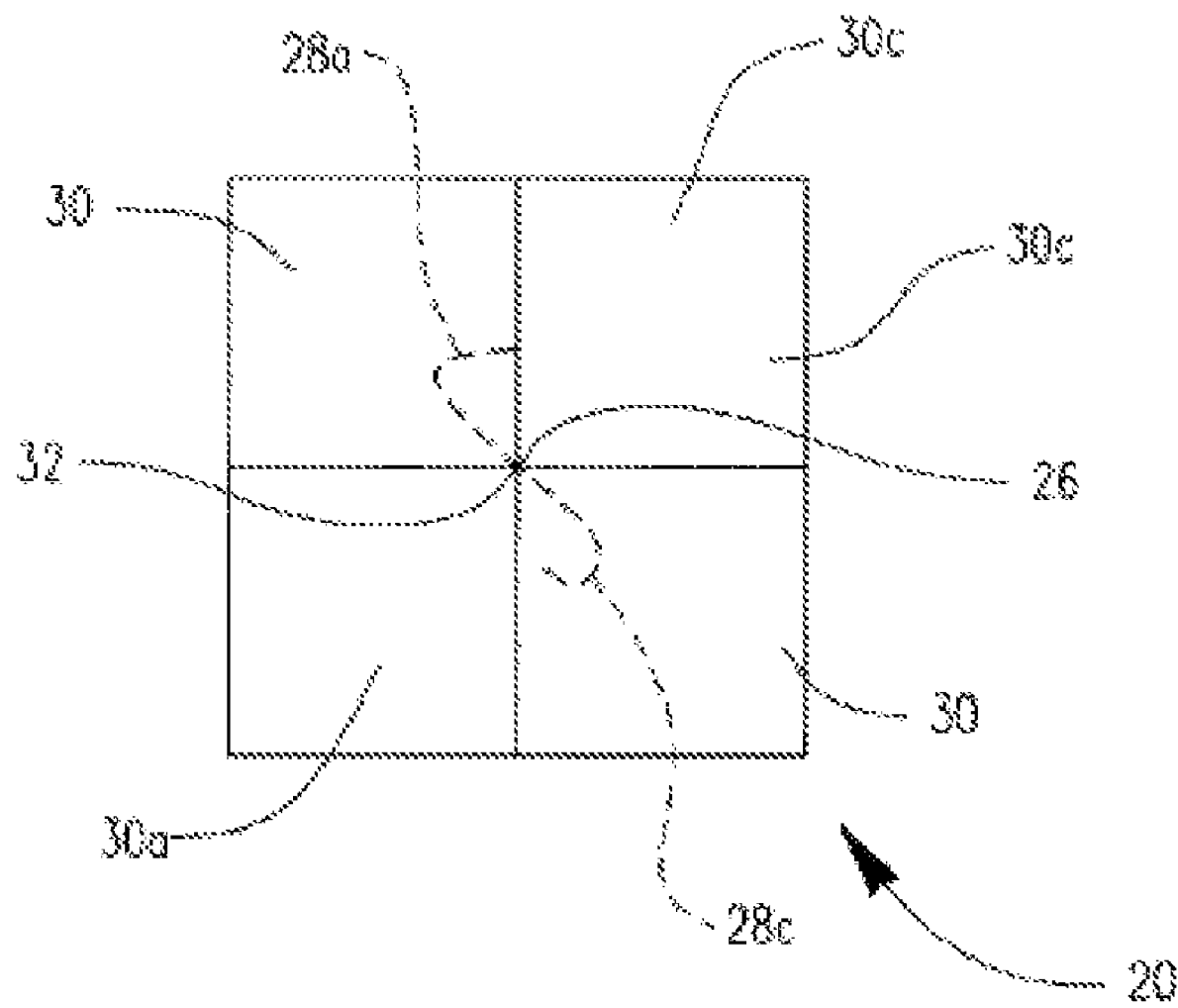
FIG. 55 is an end view of an apparatus for reducing the size of an article wherein the dies move along nonlinear paths.
Figure 56:
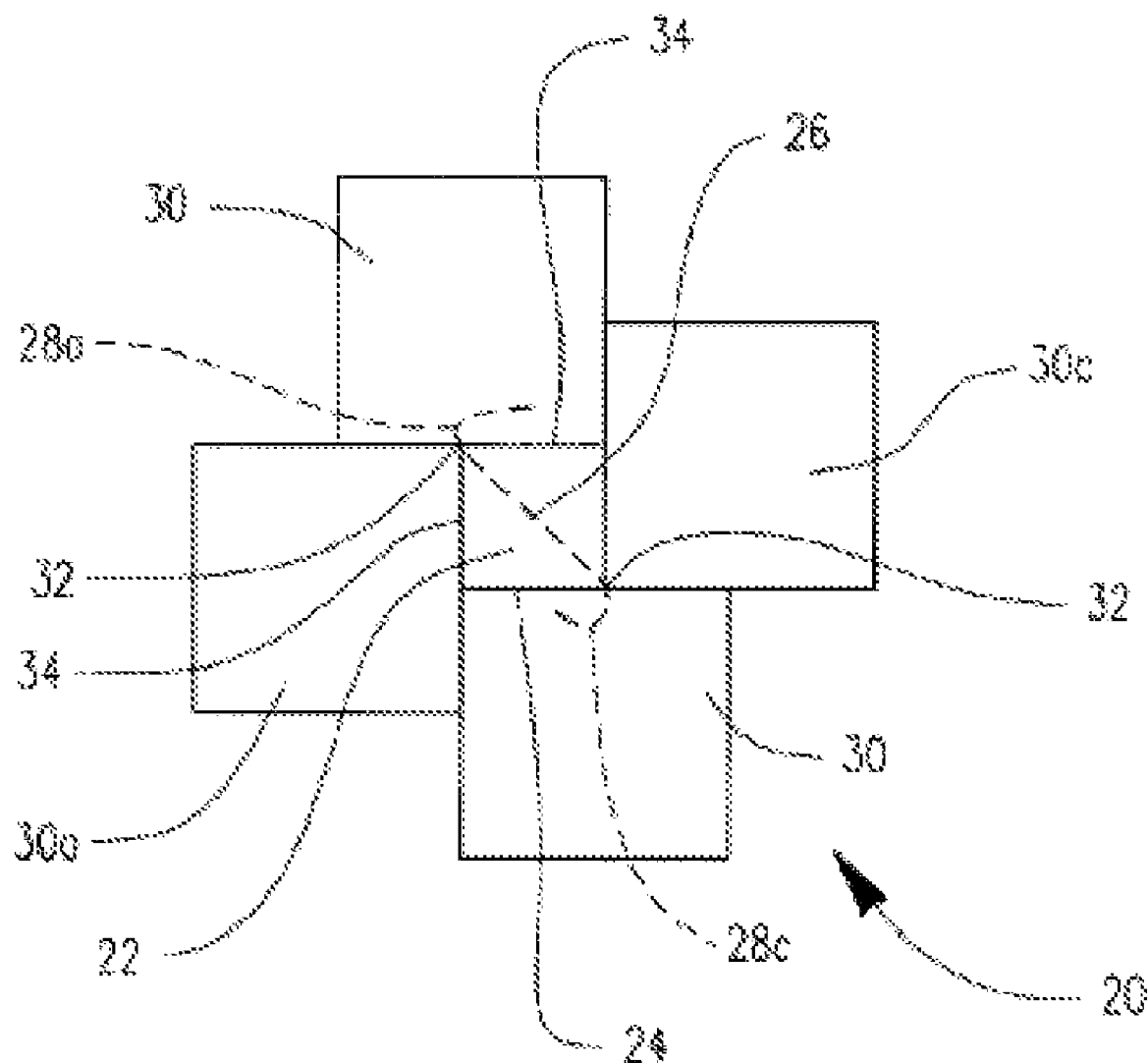
FIG. 56 is an end view of an apparatus for reducing the size of an article wherein the dies move along nonlinear paths.
Figure 57:
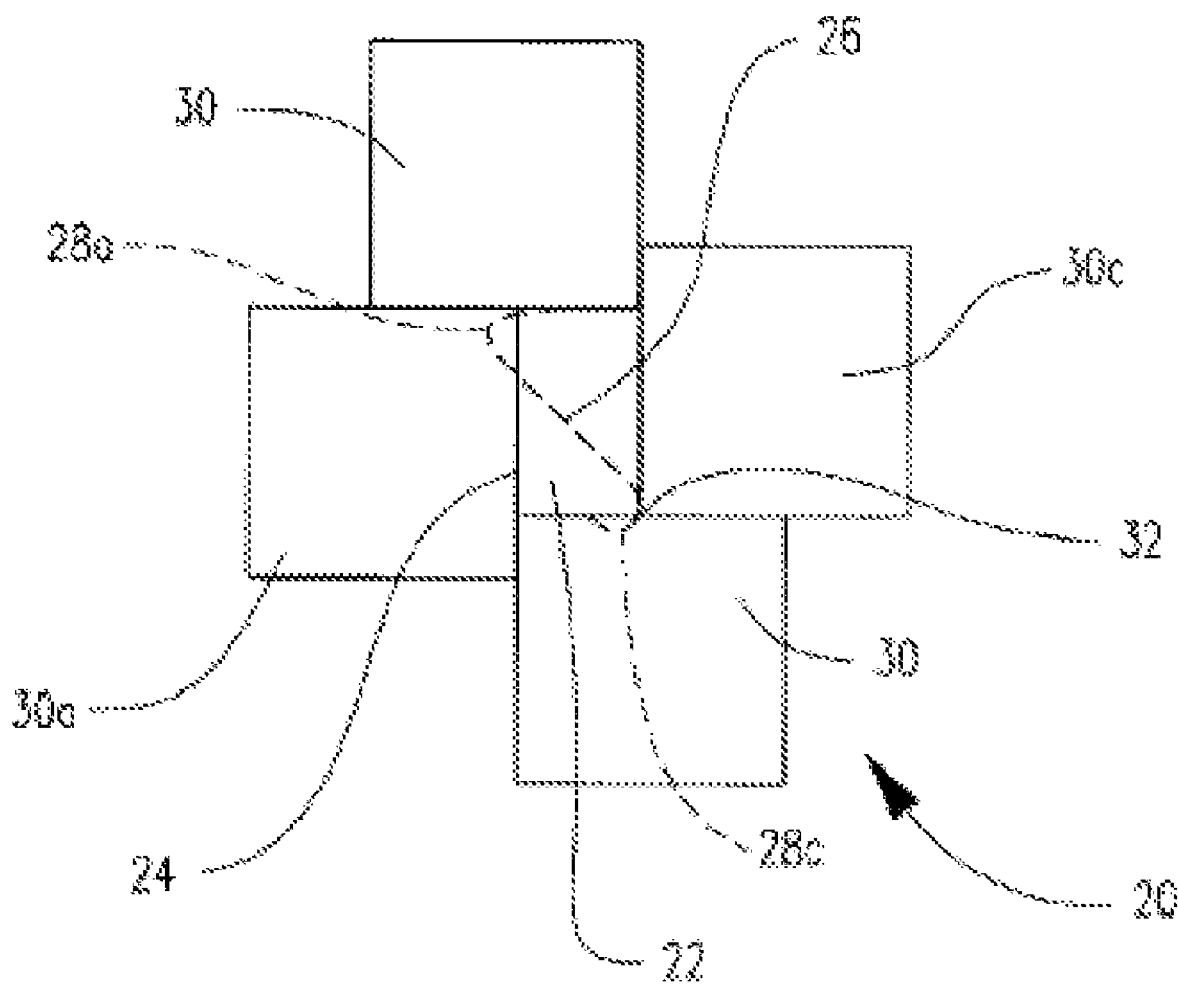
FIG. 57 is an end view of an apparatus for reducing the size of an article wherein the dies move along nonlinear paths.
Figure 58:
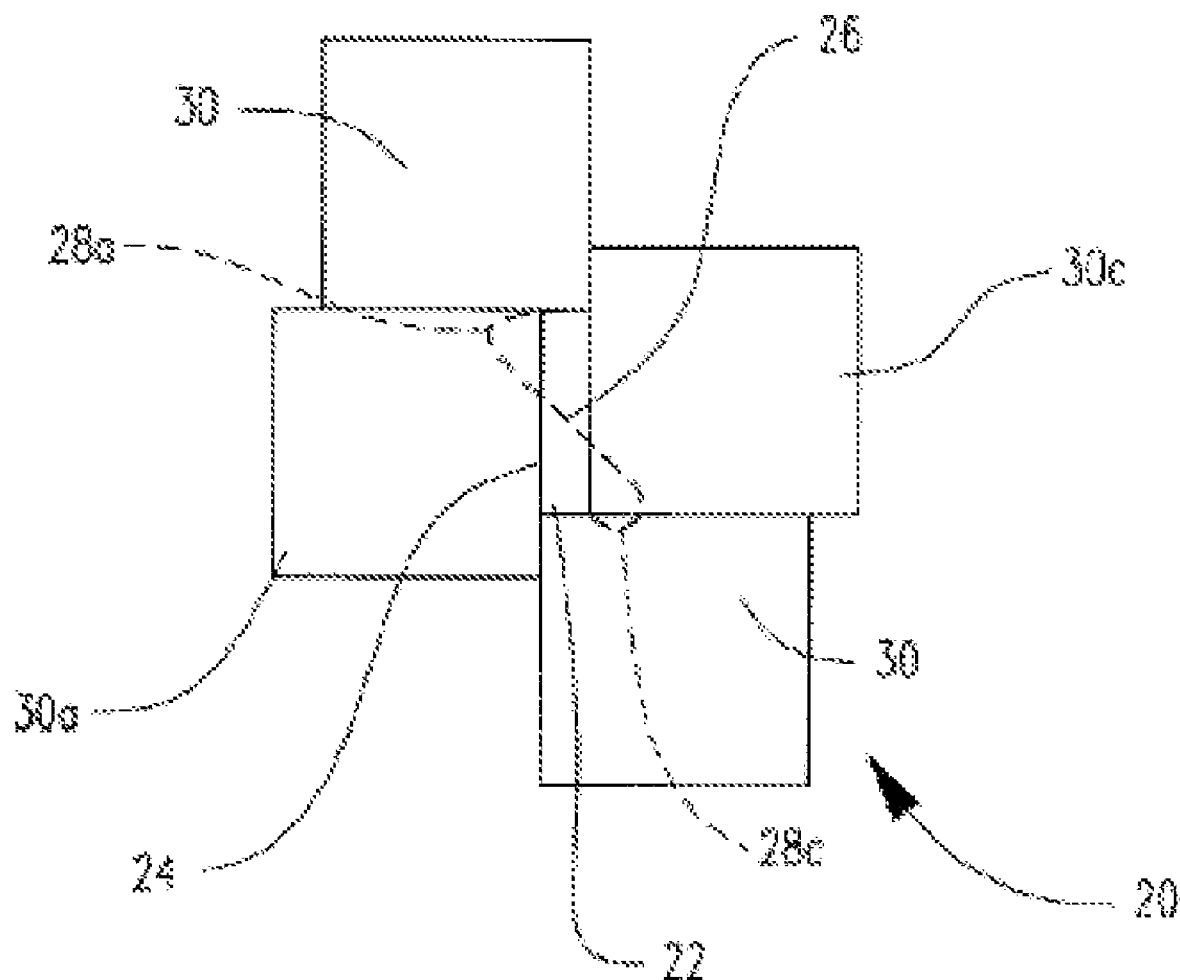
FIG. 58 is an end view of an apparatus for reducing the size of an article wherein the dies move along nonlinear paths.

FIGS. 52-54 show another embodiment of an apparatus 20 for shaping an article. The apparatus 20 may comprise a plurality of movable dies 30. There may be an odd number of dies 30. Various dies may be shaped similarly to or dissimilarly from other dies of the apparatus 20. Each die 30 maybe adjacent to at least one other die 30. Adjacent dies 30 may be slidably engaged with one another. The dies 30 may be arranged to form a chamber 22 that may run the length of the device. Wall surfaces or contacting surfaces 34 which bound the chamber 22 may comprise an iris 24. The dies 30 may be moved such that the iris 24 forms a nonregular polygon, or a polygon wherein at least one side is of a different length than another side, as shown in FIG. 53. The dies 30 may also be moved such that the iris 24 forms a regular polygon, as shown in FIG. 54.

Each die 30 may include an edge 32 and at least one contacting surface 34. A contacting surface 34 may contact and reduce the size of an article placed within the chamber 22, or contact the article to restrict expansion of the article. The exact shape of the iris 24 is dependent upon the shape, arrangement and number of contacting surfaces 34 which form the iris 24. Each edge 32 may move along a movement path 28. The movement path 28 of one die 30 may be parallel to the movement path 28 of another die 30. Further, the movement paths 28 of multiple dies may share a movement path line, as shown by line 28s in FIG. 53.

Dies 30 may follow alternate movement paths 28 depending upon the arrangement and movement of the dies 30, and thus the shape of the iris 24. For example, FIG. 52 depicts the apparatus 20 in a closed configuration. FIG. 53 depicts the apparatus 20 in a first open configuration, wherein the iris 24 is in the shape of a nonregular polygon and dies 30j and 30k follow independent movement paths 28j, 28k. FIG. 54 depicts the apparatus 20 in a second open configuration, wherein the iris 24 is in the shape of a regular polygon and dies 30j and 30k share a movement path 28jk.

An intersection of movement paths 28 may comprise a zero point 26 or a line comprised of zero points 26, wherein a plurality of die edges 32 may meet when the iris 24 is fully contracted.

FIGS. 55-58 show another embodiment of an apparatus 20 for shaping an article. The apparatus 20 may comprise a plurality of movable dies 30. Each die 30 may be adjacent to at least one other die 30. Adjacent dies 30 may be slidably engaged with one another. The dies 30 may be arranged to form a chamber 22 that may run the length of the device. Wall surfaces or contacting surfaces 34 which bound the chamber 22 may comprise an iris 24.

Each die 30 may include an edge 32 and at least one contacting surface 34. A contacting surface 34 may contact and reduce the size of an article placed within the chamber 22, or contact the article to restrict expansion of the article. The exact shape of the iris 24 is dependent upon the shape, arrangement and number of contacting surfaces 34 included in the apparatus 20.

Each edge 32 may move along a movement path 28. A movement path 28 may be nonlinear and thus may have curvature. In some embodiments, the movement paths 28 of all the dies may have a similar curvature. In some embodiments, individual movement paths 28 may have a distinct shape or curvature.

As shown in FIGS. 55-58, the edge 32 of die 30a may follow movement path 28a, and the edge 32 of die 30c may follow movement path 28c. The curvature of movement path 28a may be distinct from the curvature of movement path 28c.

An intersection of movement paths 28 may comprise a zero point 26 or a line comprised of zero points 26, wherein a plurality of die edges 32 may meet when the iris 24 is fully contracted.

As the edges 32 of the dies 30 move along respective movement paths 28, the shape and area of the iris 24 may change. At some die 30 positions, the iris 24 may form a regular polygon. At some die 30 positions, the iris 24 may form a nonregular polygon. As the iris 24 changes, the iris 24 may or may not be centered at the zero point 26.

Figure 59:
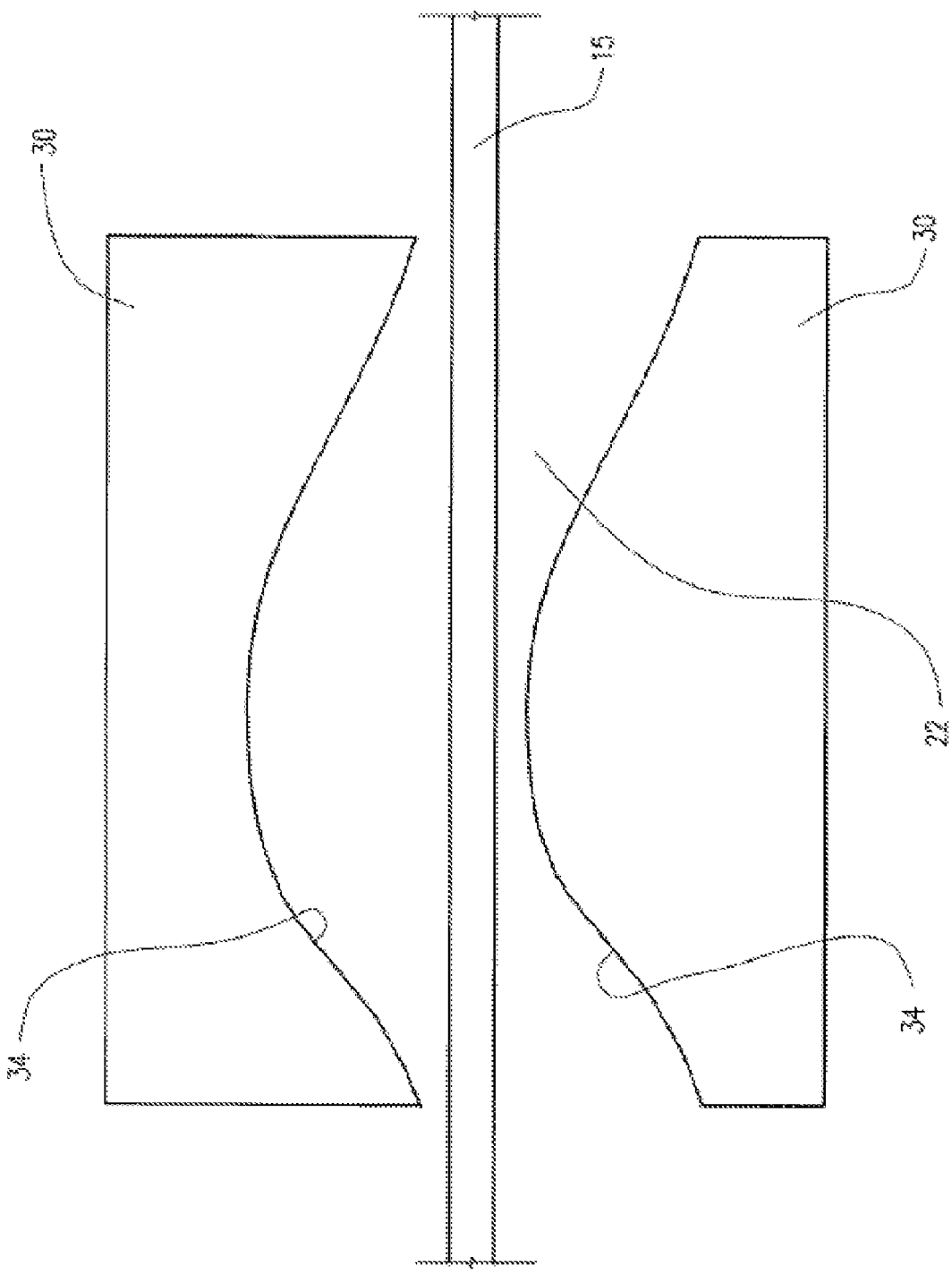
FIG. 59 shows an embodiment of an apparatus for shaping an article.
Figure 60:
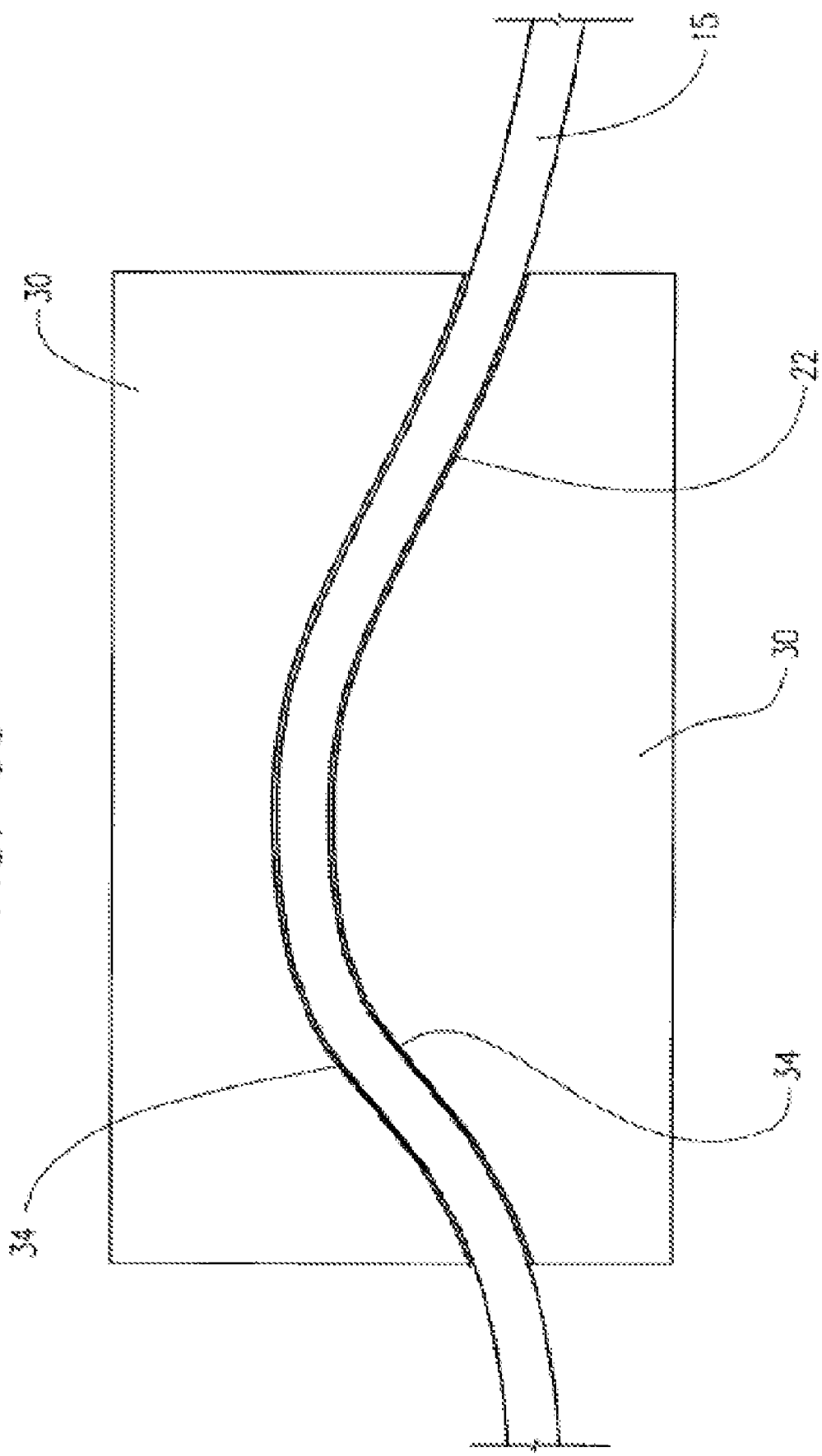
FIG. 60 shows an embodiment of an apparatus for shaping an article.
Figure 61:
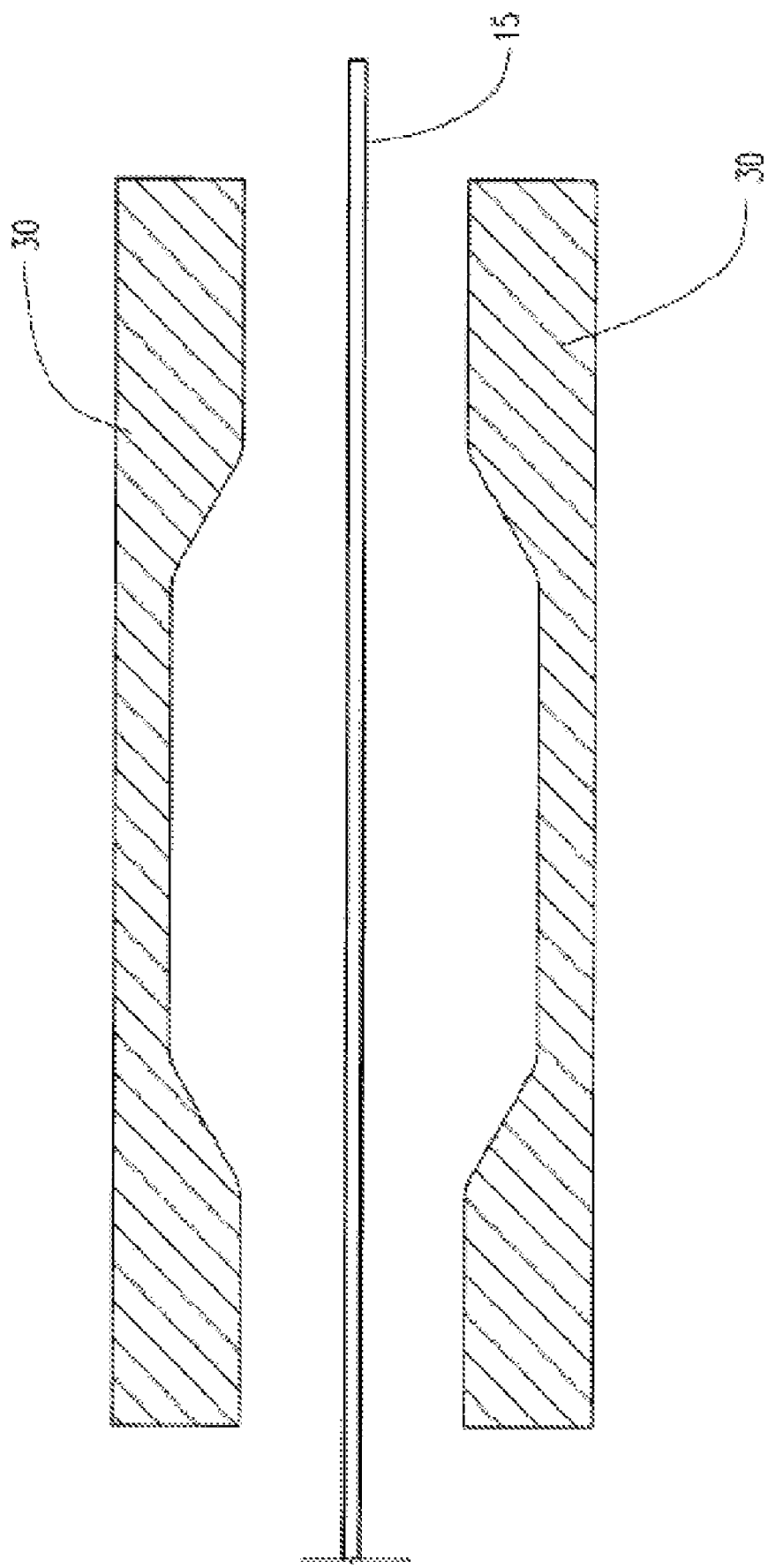
FIG. 61 shows another embodiment of an apparatus for shaping an article.

FIGS. 59 and 60 show an embodiment of an apparatus 20 for shaping an article. The apparatus 20 may include a plurality of dies 30 arranged to form a chamber 22. The size of the chamber 22 may be adjusted by movement of the dies 30. Desirably, the chamber 22 may include three-dimensional curvature. The apparatus 20 may be formed according to the principles described herein with respect to the various embodiments.

FIG. 59 shows the apparatus 20 having an article 15 placed within the chamber 22. The dies 30 may be moved in relation to one another to alter the size of the chamber 22, and the size of the chamber 22 may be reduced.

Contacting surfaces 34 of the dies 30 which form the chamber 22 may contact the article 15. As the size of the chamber 22 is reduced, the three-dimensional shape and curvature of the chamber 22 may be imparted to the article 15, as shown in FIG. 60.

An apparatus 20, as well as the other inventive devices disclosed herein, may be used in a number of ways. They may be used to shape wires and catheters, to shape catheter tips, to reduce the size of stents and other medical devices and the like. They may also be used to repeatedly impart various shapes to an article 15 to simulate various bending situations. For example, repeated bending of a stent may simulate long term behavior of stents designed to be used in places of the body that are subject to repeated bending, such as in the knee. For example, an article may be positioned within the chamber 22 and the size of the chamber may be reduced to impart the article with shape of the chamber 22. The size of the chamber 22 may be increased, the article 15 may be repositioned within the chamber 22, and the size of the chamber 22 may again be reduced to impart the article with an alternate shape or curvature. The process may be repeated as desired. For another example, an article 15 of shape memory material may be placed within the chamber 22 and the size of the chamber 22 may be reduced to impart the shape memory material with the shape of the chamber 22. The size of the chamber 22 may then be increased, allowing the article 15 to return to a shape memory shape. The chamber 22 may again be reduced without repositioning of the article 15, thereby reimparting the shape of the chamber 22 to the article. The operation may be repeated as desired.

FIGS. 61-64 show an embodiment of an apparatus 20 for shaping an article. The apparatus 60 may comprise a plurality of dies 30 arranged to for a chamber 22, for example as described with respect to FIG. 36.

Figure 62:
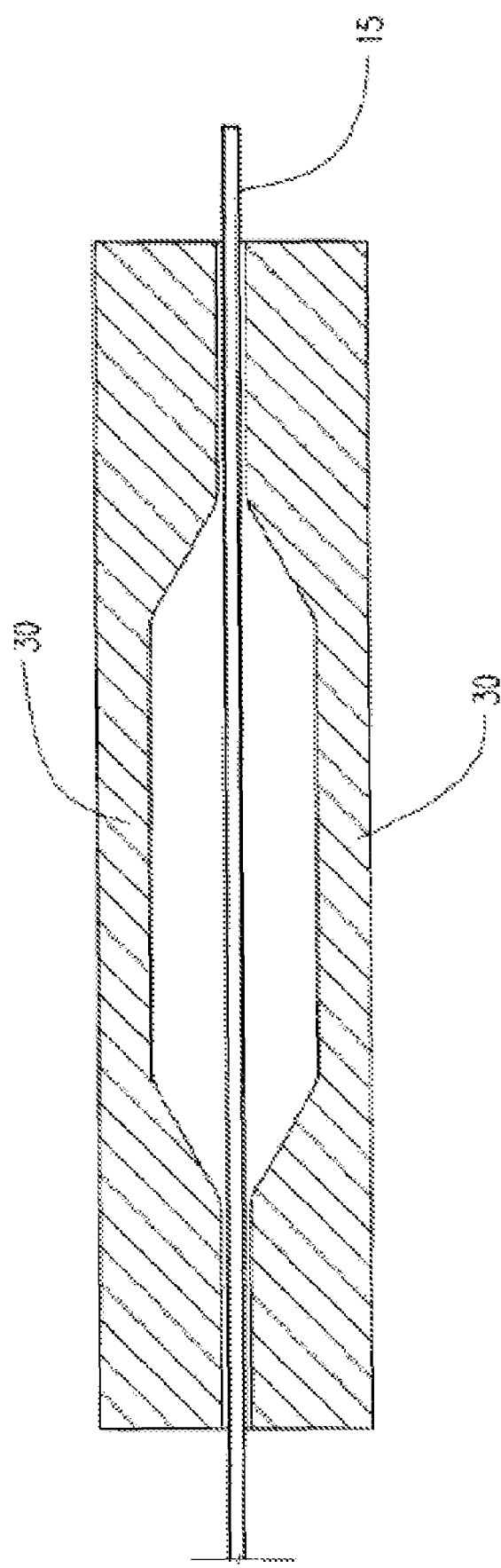
FIG. 62 shows an embodiment of an apparatus for shaping an article with a balloon precursor arranged in the chamber.
Figure 63:
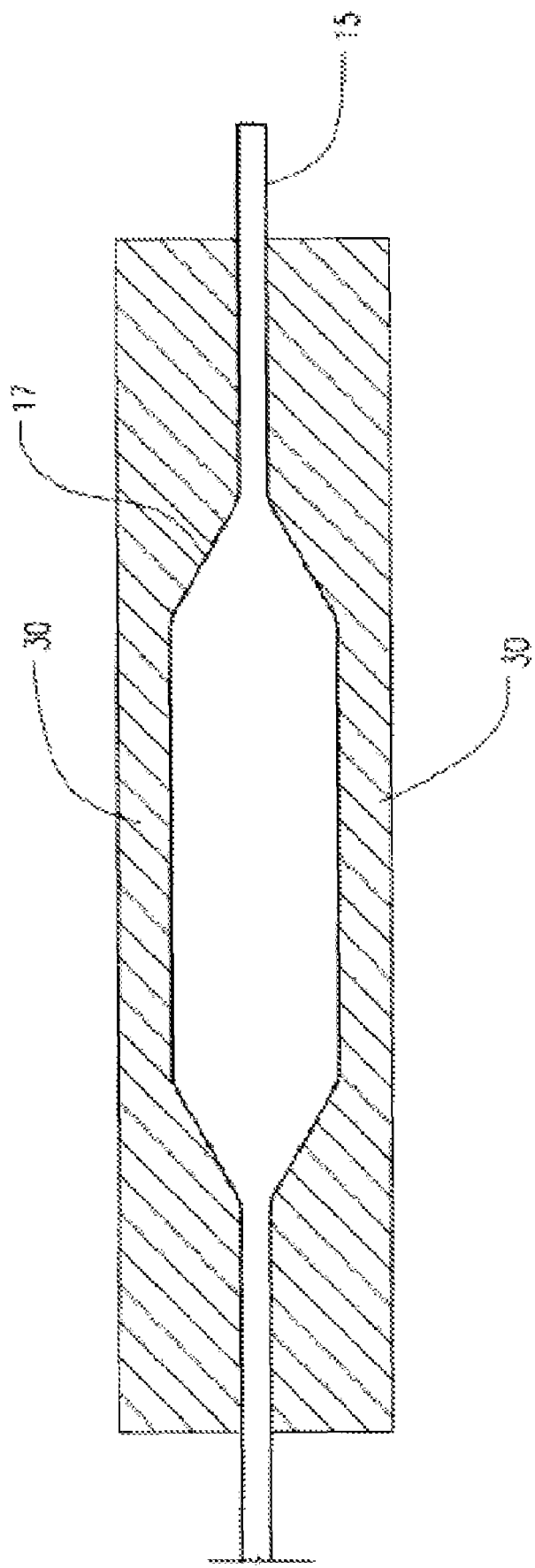
FIG. 63 shows an embodiment of an apparatus for shaping an article with a balloon arranged in the chamber.

An article 15, such as a tube, parison or balloon precursor, may be placed within the chamber 22, and the size of the chamber 22 may be reduced such that a portion of the contacting surface 34 of each die 30 may contact a portion of the article 15 (FIG. 62). Pressurized inflation fluid may be applied to the interior of the article 15, thus blowing or inflating a balloon 17, as shown in FIG. 63. The article 15 may inflate until it contacts the contacting surfaces 34 that form the chamber 22 along its entire length. The contacting surfaces 34 of the dies 30 may contact the article 15, impart the shape of the chamber 22 to the article 15 and restrict the article 15 from further expansion. Thus, the inflated shape of the article 15 may be determined by the shape of the chamber 22.

Figure 64:
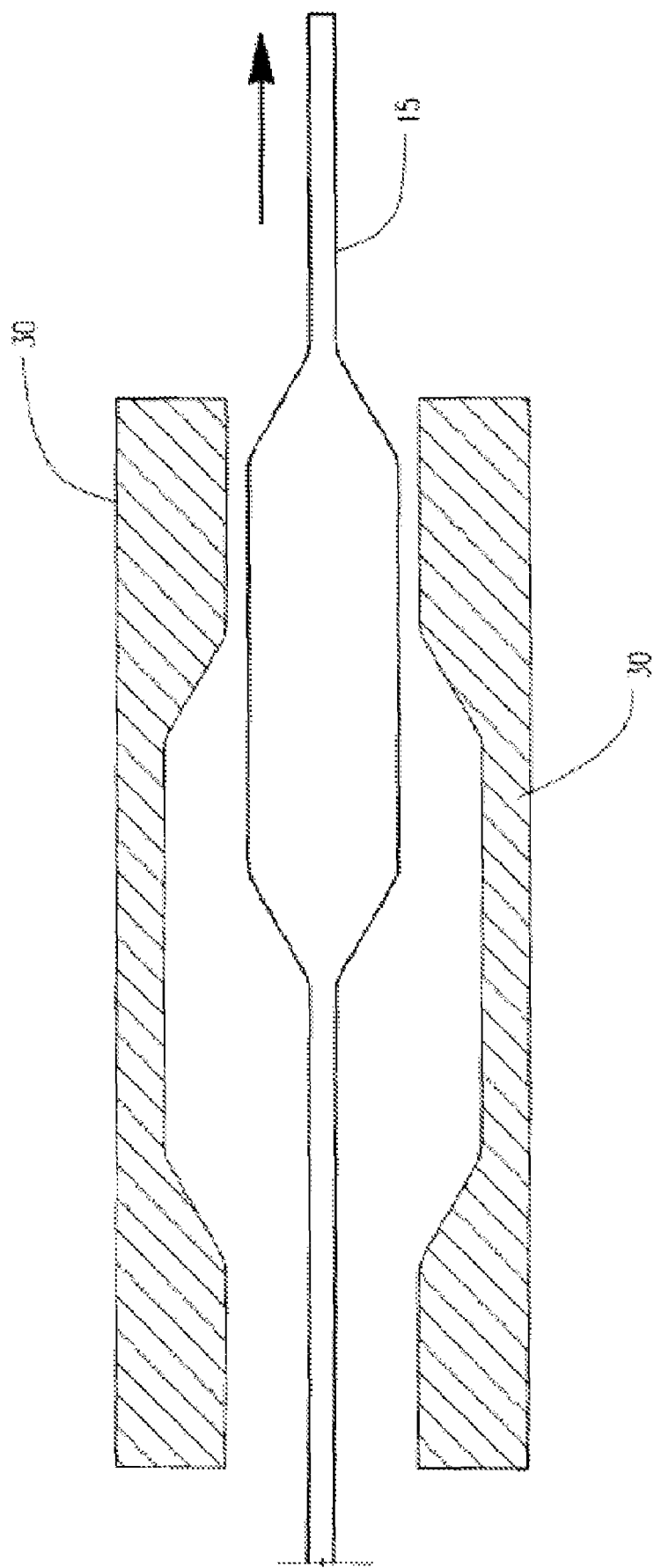
FIG. 64 shows an embodiment of an apparatus for shaping an article.

After the article 15 is fully shaped, the fluid may be removed. The dies 30 may be moved to increase the size of the chamber 22, allowing the article 15 to be removed (FIG. 64).

Figure 65:
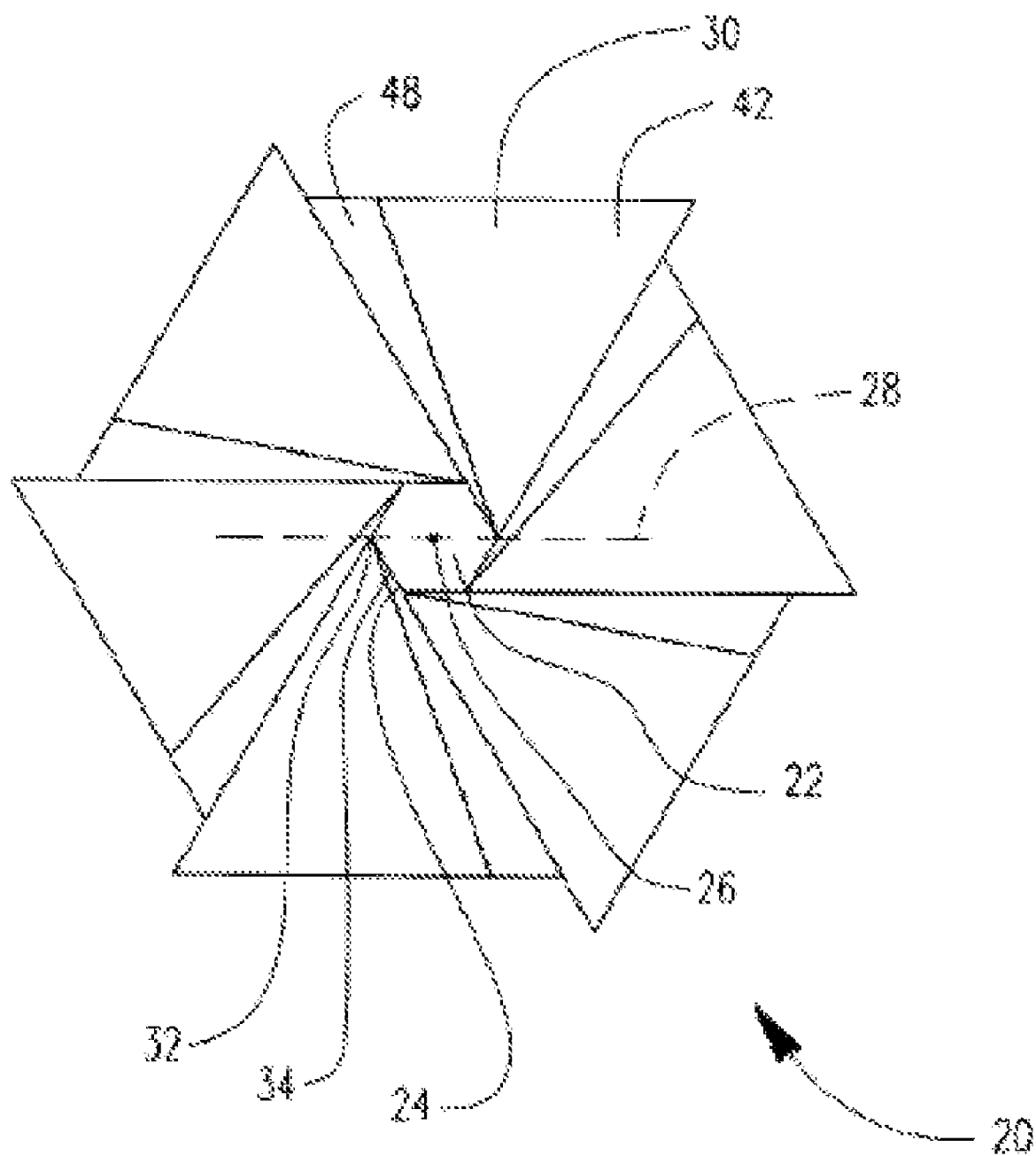
FIG. 65 shows an end view of another embodiment of an apparatus for shaping an article.
Figure 66:
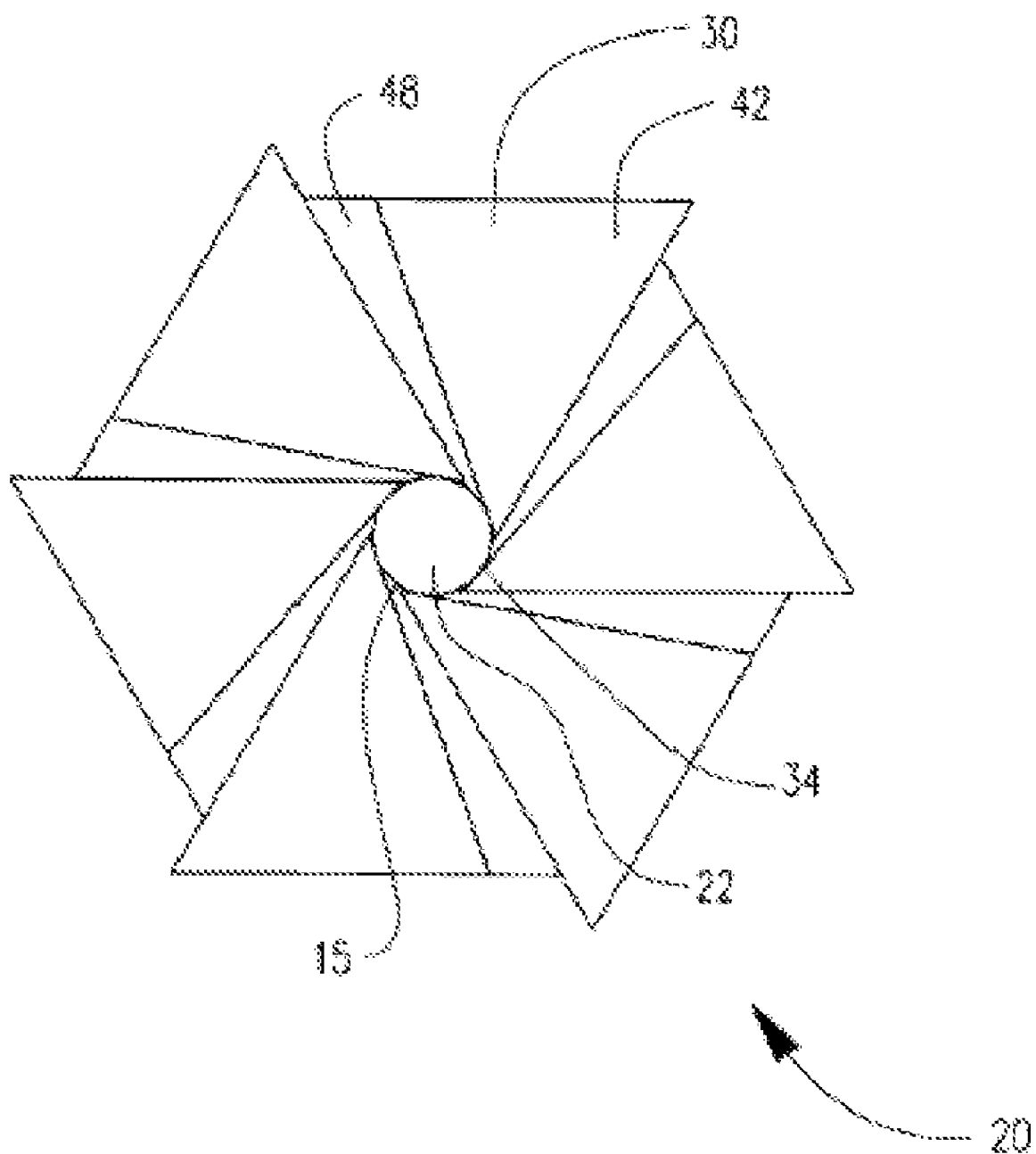
FIG. 66 shows an end view of an embodiment of an apparatus for shaping an article.
Figure 67:
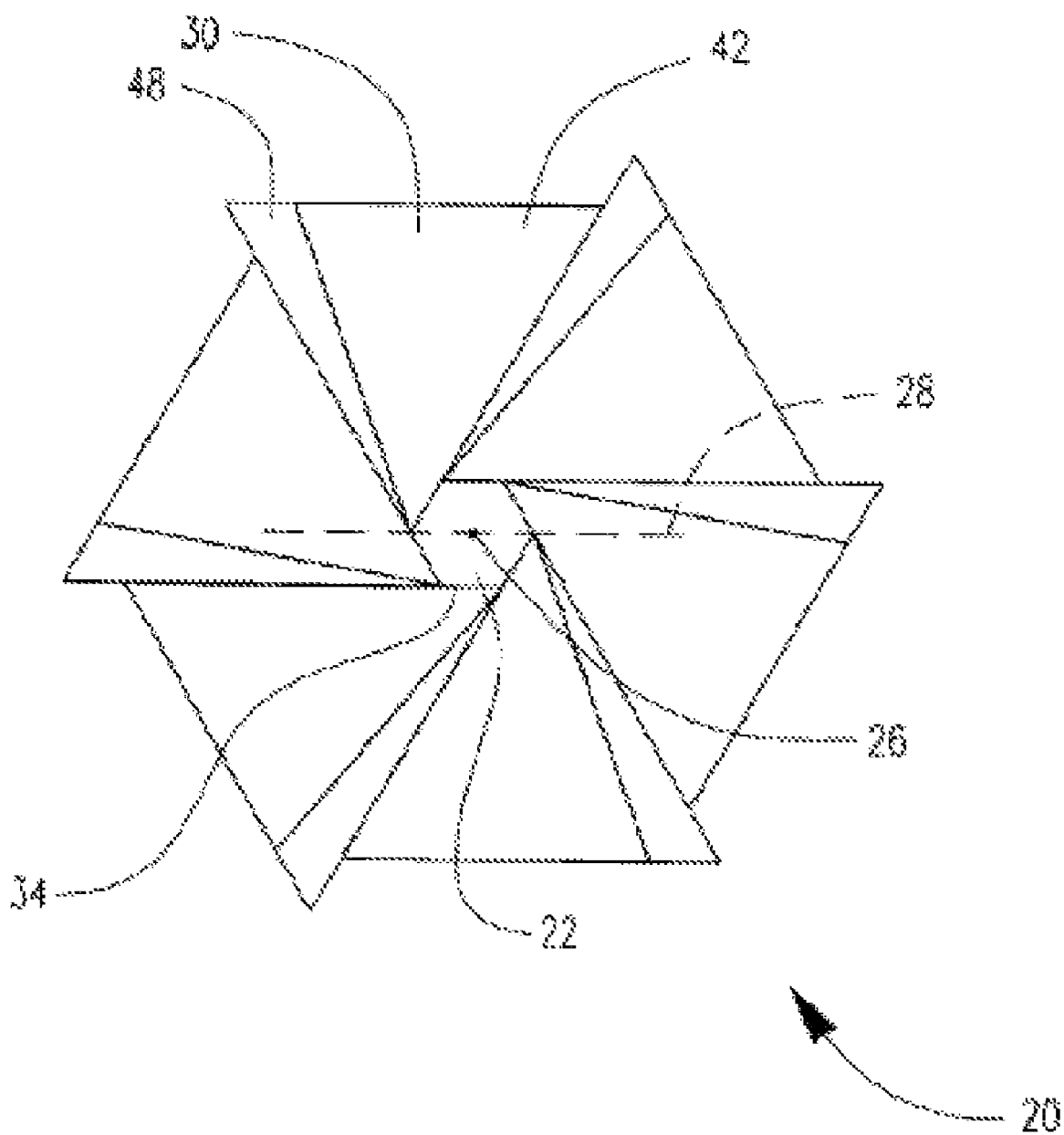
FIG. 67 shows an end view of an embodiment of an apparatus for shaping an article in another open configuration.

FIGS. 65-67 show another embodiment of an apparatus 20 for shaping an article. The apparatus 20 may comprise a plurality of movable dies 30. Each die 30 may have a first portion 42 made from a first material and a second portion 48 made from a second material. The first portion 42 may be made from a rigid material. Desirably, the second portion 48 may be made from an elastically deformable material and may comprise a pad. For example, any soft polymeric material may be used, such as elastomers and more specifically block copolymer elastomers. In some embodiments, the second portion 48 may be made from a silicone rubber suitable for biomedical use, such as Silastic® BioMedical Grade Liquid Silicone Rubber available from Dow Corning. Desirably, a silicone rubber may have a low durometer hardness of 30 A or less, such as Silastic® 7-6830, and be suitable for use with the apparatus 20 during warming and cooling as herein described.

Each die 30 may be adjacent to at least one other die 30. Adjacent dies 30 may be slidably engaged with one another. The dies 30 may be arranged to form a chamber 22 that may run the length of the device. The size of the chamber 22 may be varied by movement of the dies 30. Wall surfaces or contacting surfaces 34 which bound the chamber 22 may comprise an iris 24.

Each die 30 may include an edge 32 and at least one contacting surface 34. An edge 32 may include a portion of the first portion or material 42 and a portion of the second portion or material 48. A contacting surface 34 may contact and reduce the size of an article placed within the chamber 22, or contact the article to restrict expansion of the article. The exact shape of the iris 24 is dependent upon the shape, arrangement and number of contacting surfaces 34 which form the iris 24. Each edge 32 may move along a movement path 28. The movement path 28 of one die 30 may be parallel to the movement path 28 of another die 30. Further, the movement paths 28 of multiple dies may share a movement path line.

An intersection of movement paths 28 may comprise a zero point 26 or a line comprised of zero points 26, wherein a plurality of die edges 32 may meet when the iris 24 is fully contracted.

FIG. 66 shows the apparatus 20 shaping an article 15. Upon contacting the article 15, the second portion 48 of the dies 30 may exhibit elastic deformation. Thus, the shape of the iris 24 may change in accordance with any curvature of the article 15 being shaped, allowing the iris 24 to shape the article 15 to a more curved or less polygonal cross section. Further, elastic deformation of the second portion 48 may reduce damage to coated articles, such as drug-coated stents, and may allow crimping a given article with an apparatus 20 having fewer dies 30 than was possible in the prior art.

FIG. 67 shows the apparatus 20 in an alternate open configuration from that of FIG. 65, wherein the dies 30 have moved through the zero point 26 and the chamber 22 has reopened. In an alternate open configuration, the contacting surface 34 of each die 30 may be the first portion 42 of the die 30. Thus, the apparatus 20 may be configured such that the second portion 48 of a die 30 does not form a portion of the chamber 22.

Figure 68:
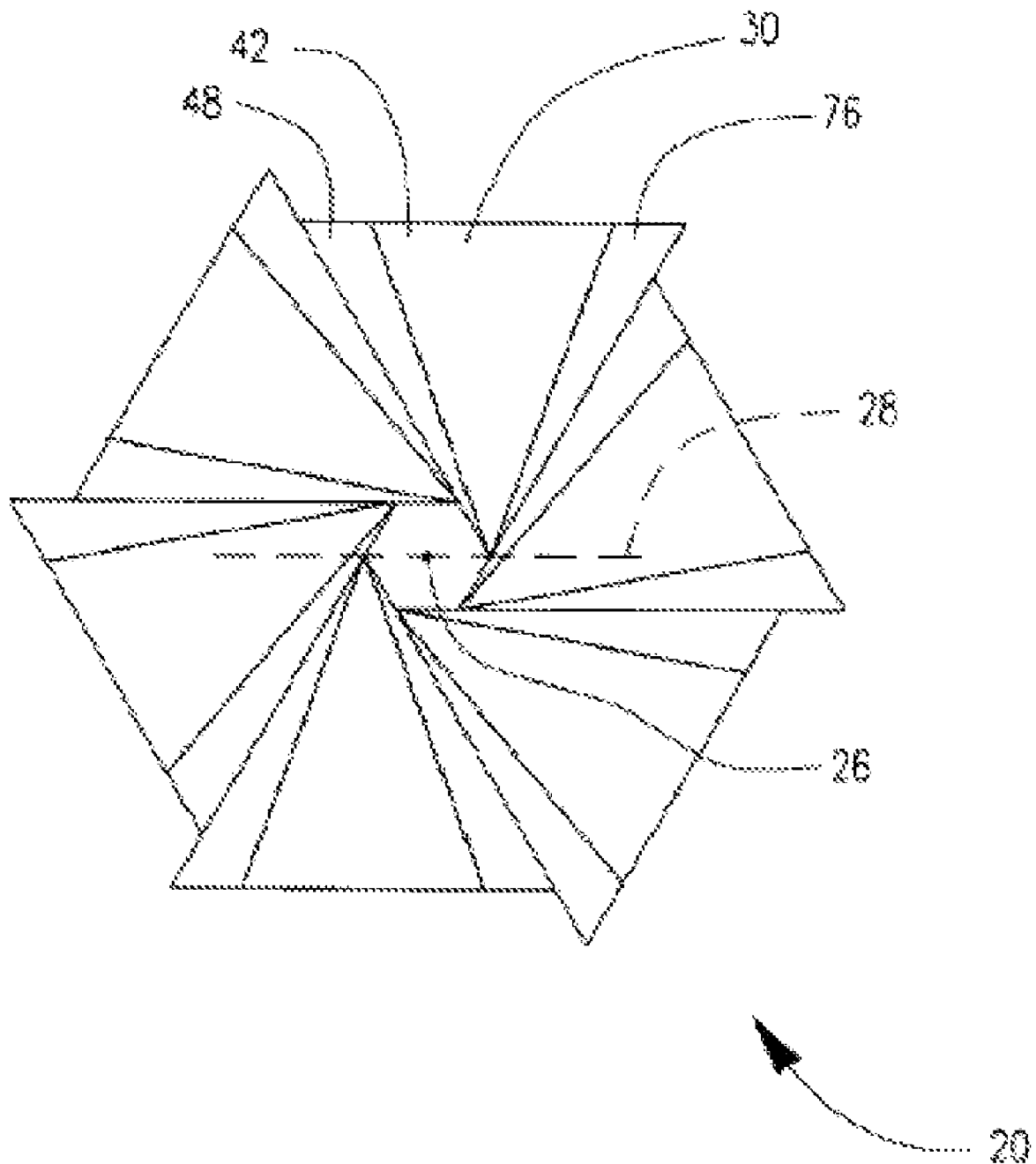
FIG. 68 shows an end view of another embodiment of an apparatus for shaping an article.

FIG. 68 shows another embodiment of an apparatus 20 for shaping an article that is similar to the embodiment of FIGS. 65-67, wherein each die 30 may further include a third portion or material 76. The third portion 76 may be made from a material similar to the first portion 42 or second portion 48 as disclosed herein, or may be made from a material different than the material of the first portion 42 or the second portion 48. The third portion 76 may be made from a material that is softer than the first portion 42 and harder than the second portion 48. Thus, in a first open configuration, material according to the second portion 48 may bound the chamber 22. In a second or alternate open configuration, wherein the dies 30 have moved through a zero point 26 and the chamber 22 has reopened, material according to the third portion 76 may bound the chamber 22.

Figure 69:
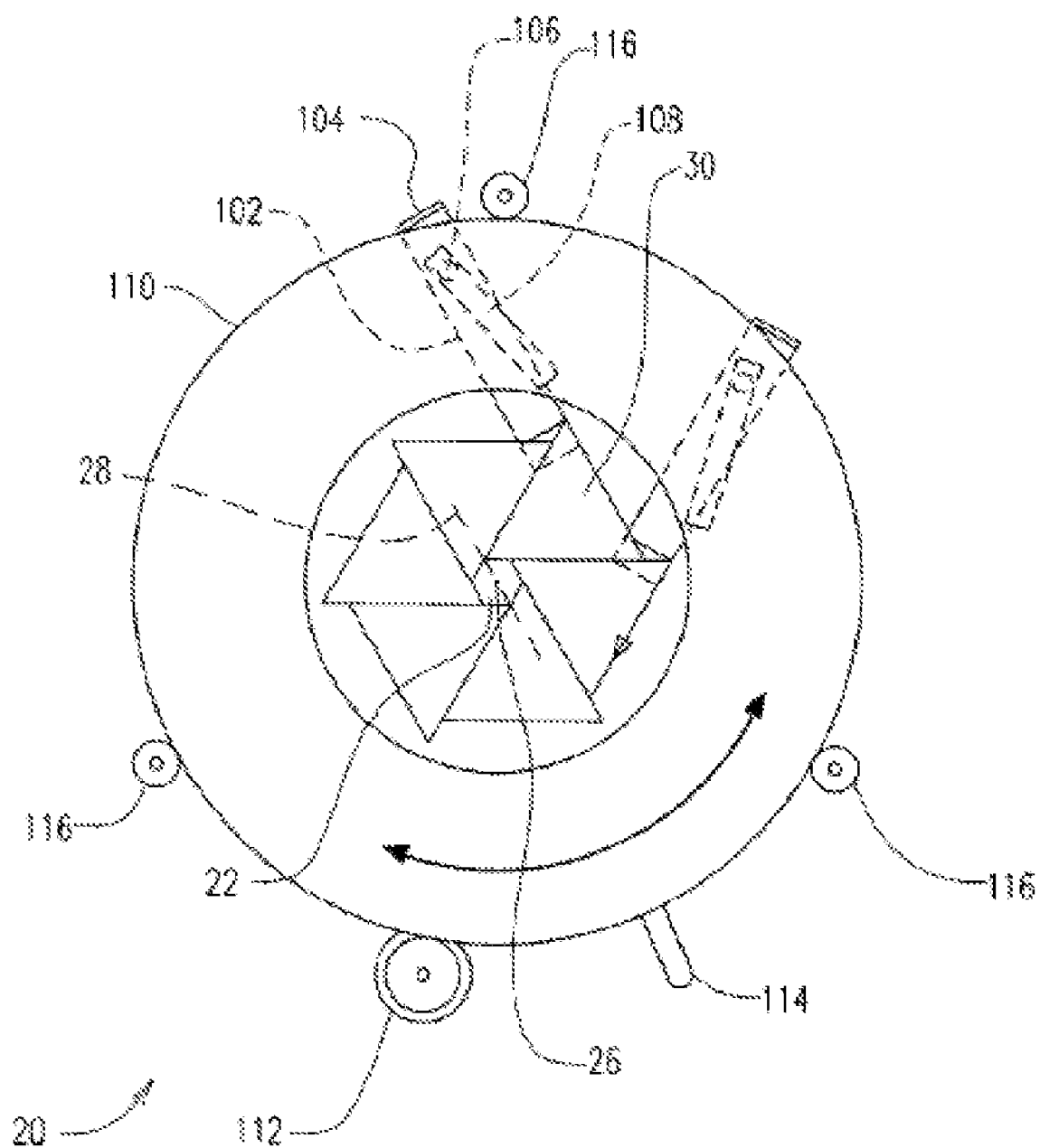
FIG. 69 shows an embodiment of an apparatus for shaping an article.
Figure 70:
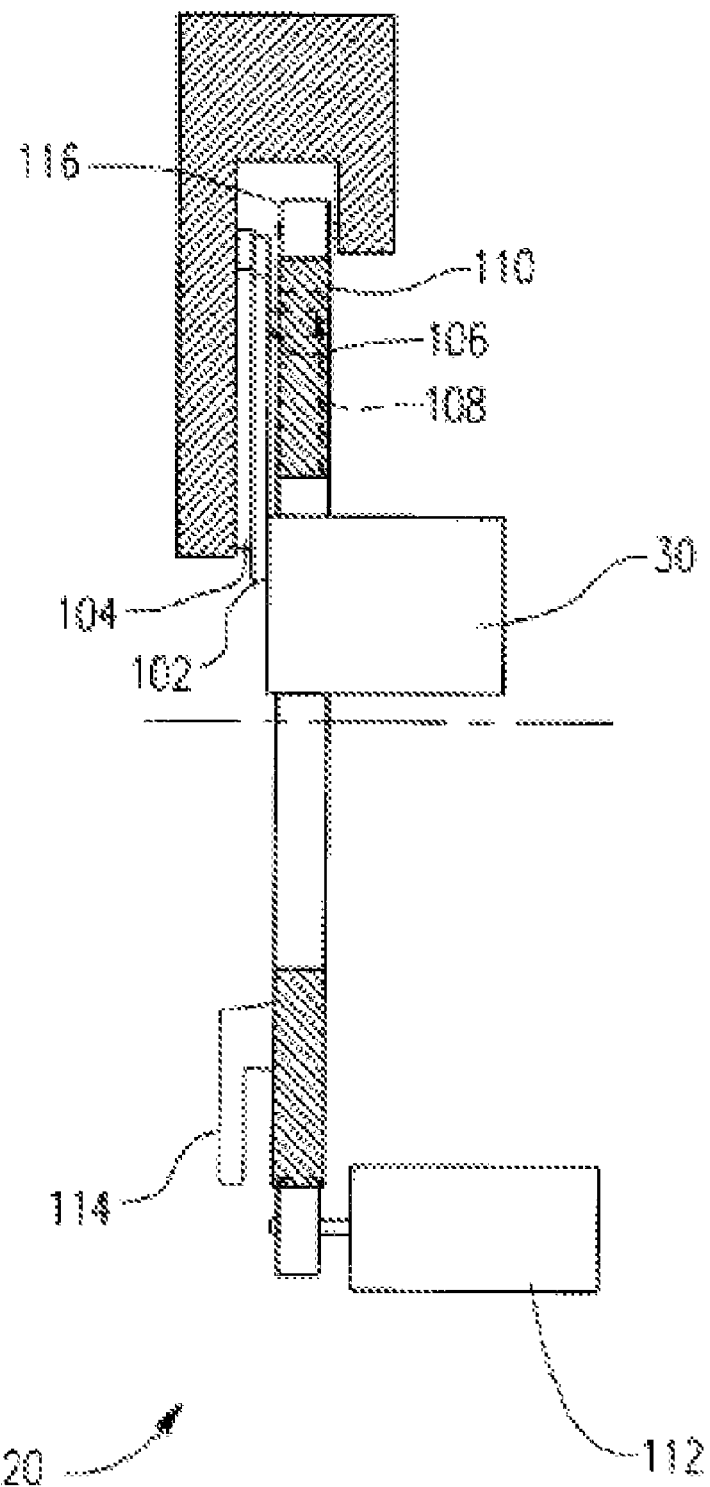
FIG. 70 shows a side view of the apparatus for shaping an article according to FIG. 69.
Figure 71:
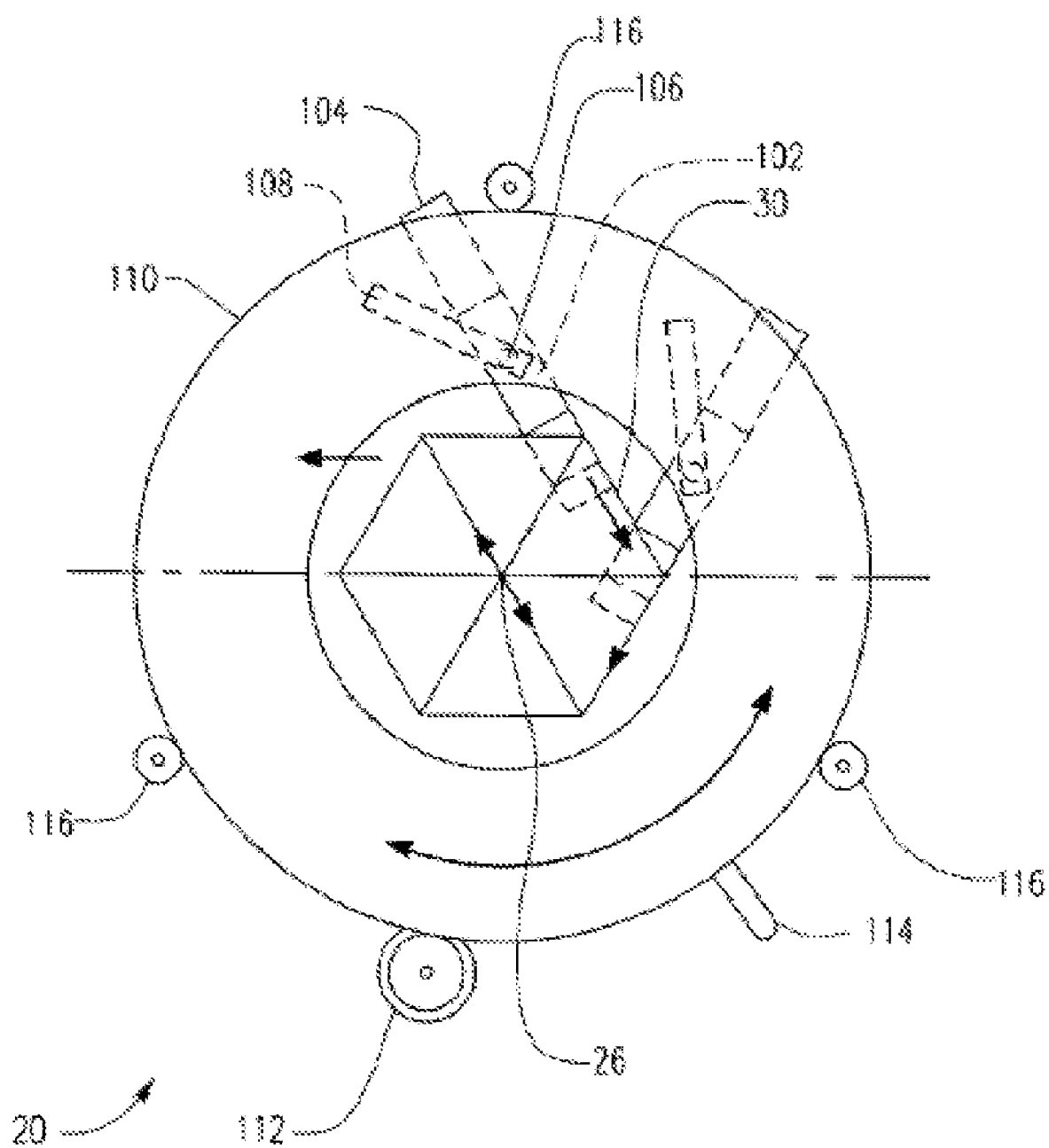
FIG. 71 shows the apparatus for shaping an article of FIG. 69 in a closed configuration.
Figure 72:
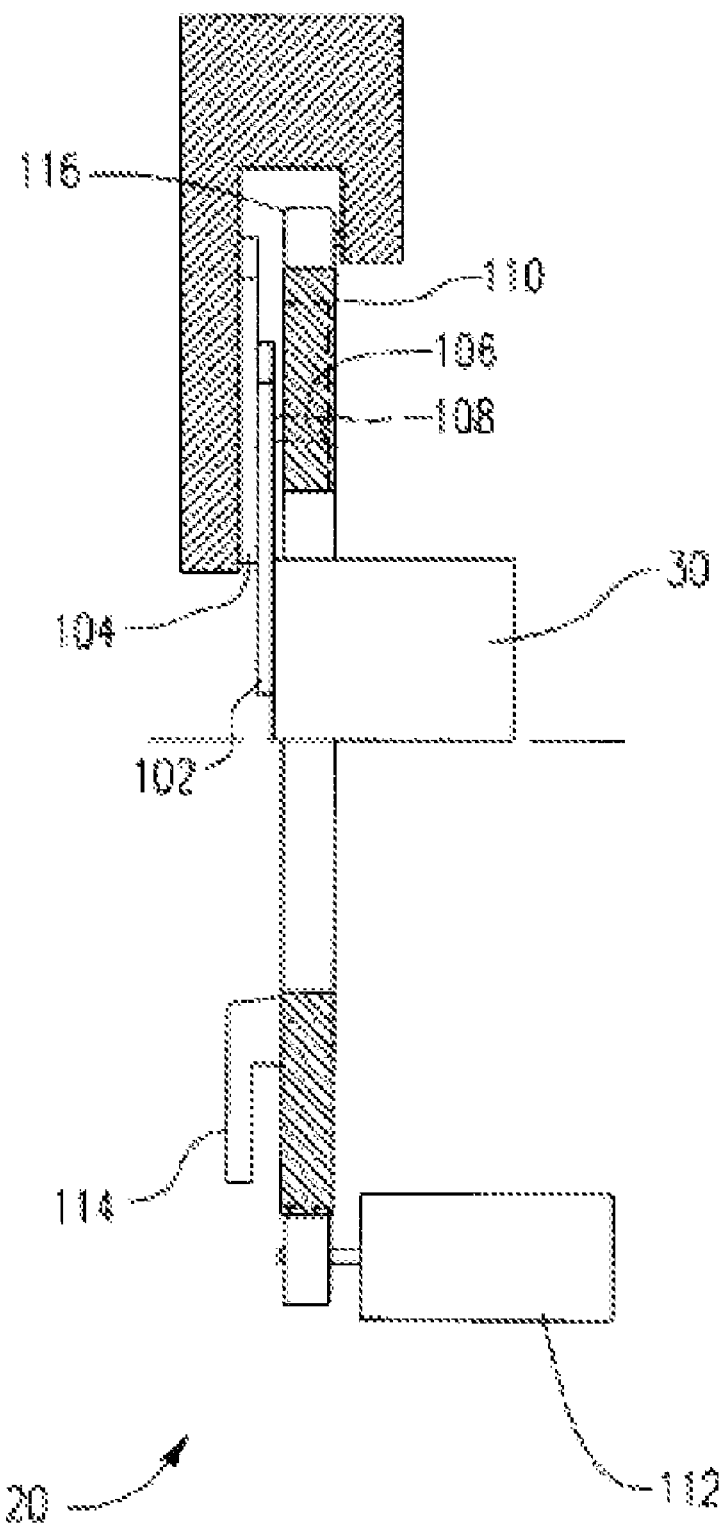
FIG. 72 shows a side view of the apparatus for shaping an article according to FIG. 71.

FIGS. 69-72 show an embodiment of an apparatus 20 for shaping an article including structure for moving the dies 30 to vary the size of the chamber 22. FIG. 69 shows the apparatus 20 in an open configuration. FIG. 70 is a partial side view of the apparatus 20 as shown in FIG. 69. FIG. 71 shows the apparatus 20 in a closed configuration. FIG. 72 is a partial side view of the apparatus 20 as shown in FIG. 71. While FIGS. 69-72 show structure for moving one or two dies 30 of the apparatus 20, appropriate portions of the structure may be replicated accordingly with respect to each die 30 as would be understood by a person of ordinary skill in the art.

Each die 30 may be coupled to an extension arm or table 102. Alternatively, a die 30 may include an extension arm or table 102. A table 102 may be slidably engaged with a fixed or stationary mount 104. Linear movement of the table 102 with respect to the mount 104 may cause the die 30 that is coupled to the table 102 to move along a movement path 28 (FIG. 69).

The apparatus 20 may further include a drive plate or drive ring 110. The center of the drive ring 110 may optionally correspond to a zero point 26 or a center of a portion of the chamber 22 formed by the dies 30. The drive ring 110 may be rotatable about a zero point 26. The drive ring 110 may include a plurality of slots 108. For example, one slot 108 may be provided for each die 30. Each table 102 may include or may be coupled to a pin 106. Each pin 106 may be oriented in a slot 108 of the drive ring 110. As the drive ring 110 rotates, each pin 106 may bear against the wall of a respective slot 108, thereby causing linear movement of the tables 102 and dies 30 with respect to the stationary mounts 104. As the dies 30 move, the size of the chamber 22 may be varied.

Movement or rotation of the drive ring 110 may be accomplished by any suitable method. For example, a lever 114 may be provided and coupled to the drive ring 110. Further, a motor 112, such as an electric motor, may be arranged to operate the drive ring 110.

Stabilizing rollers 116 may be provided to stabilize the drive ring 110 against unwanted translocation.

Figure 73:
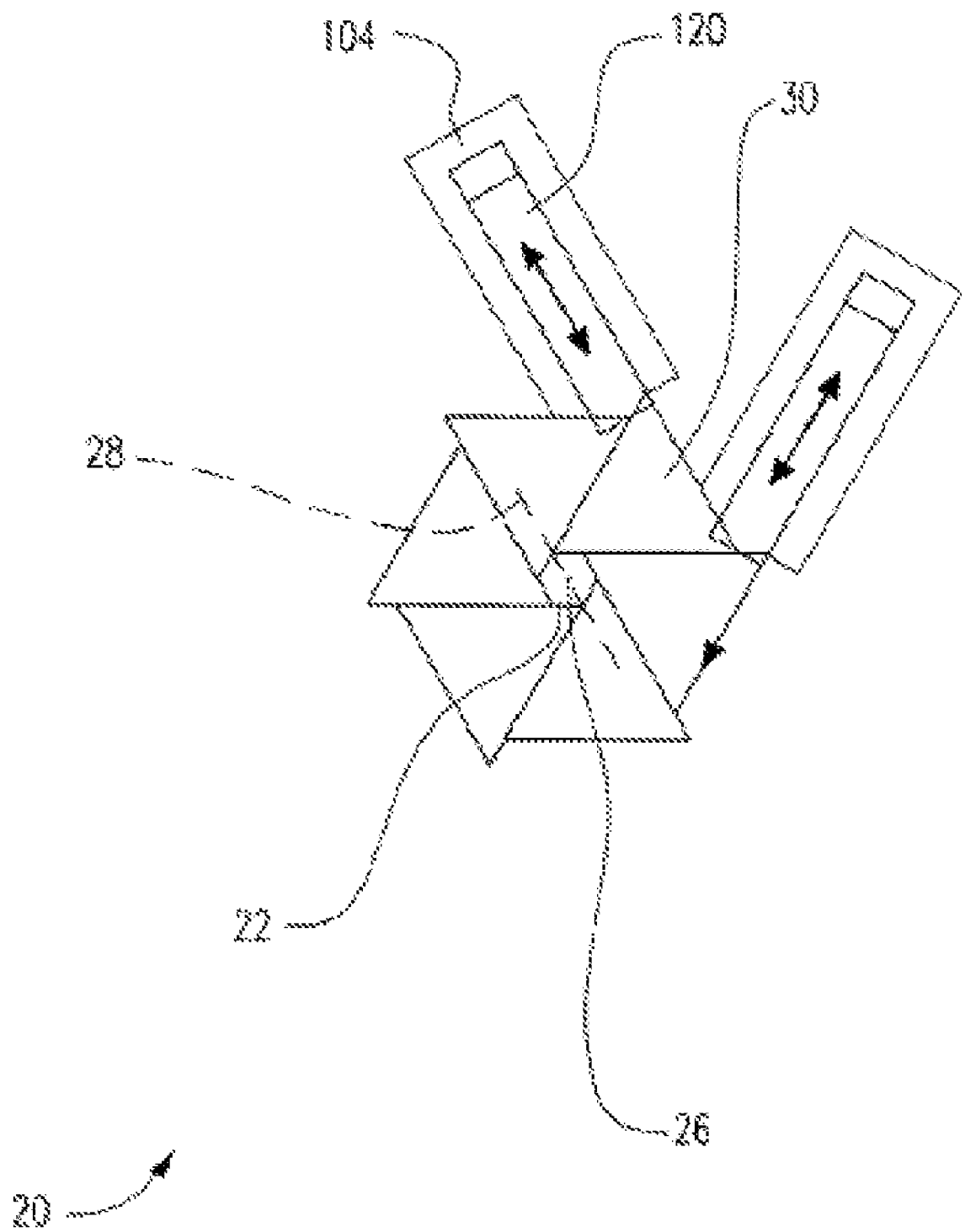
FIG. 73 shows an embodiment of an apparatus for shaping an article.
Figure 74:
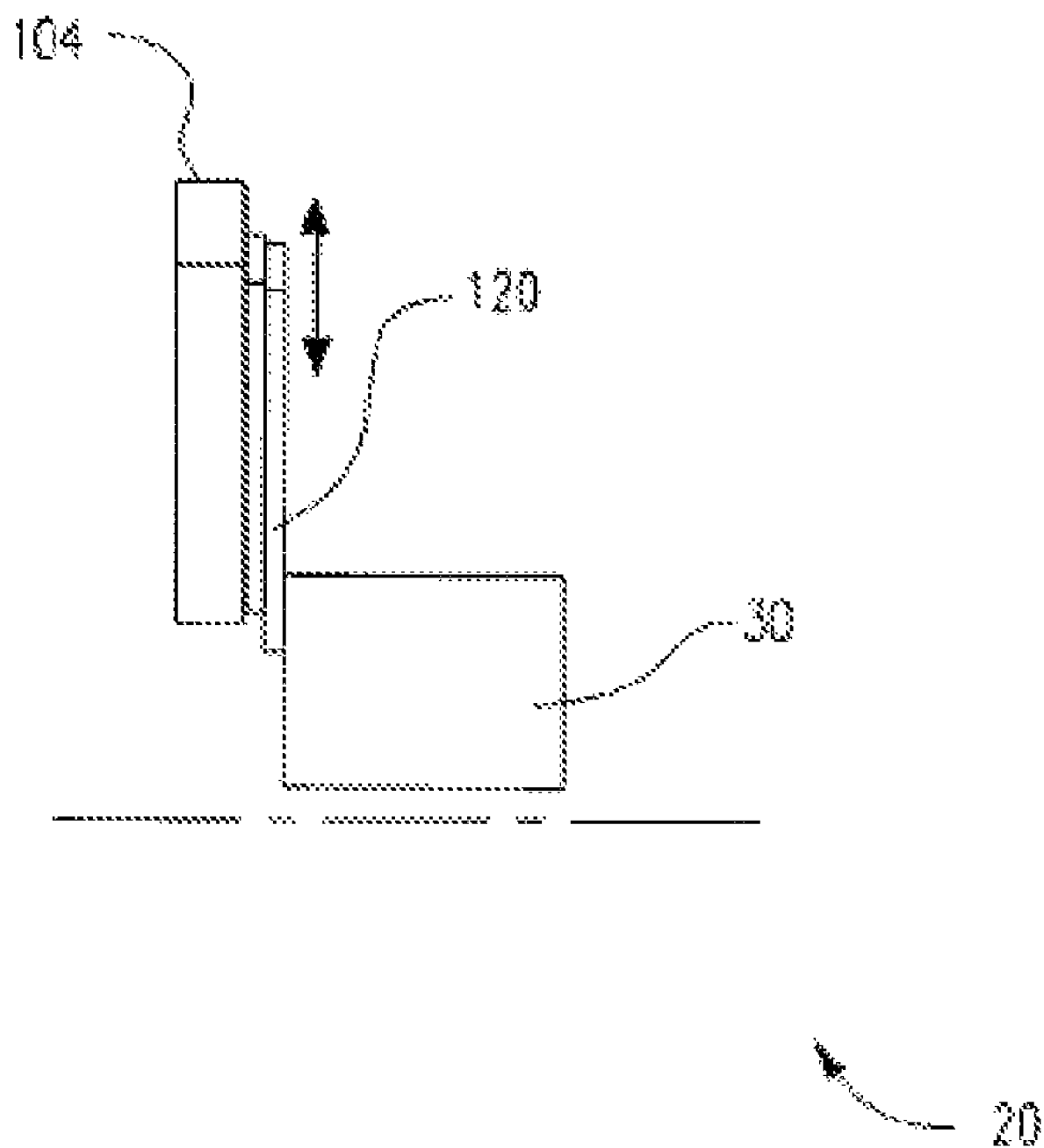
FIG. 74 shows a side view of the apparatus for shaping an article according to FIG. 73.

FIGS. 73 and 74 show another embodiment of an apparatus 20 for shaping an article including structure for moving the dies 30 to vary the size of the chamber 22. Each die 30 may be coupled to an actuation device 120 such as a linear actuator. The actuation device 120 may be mounted to a fixed or stationary mount 104. Each actuation device 120 may move a die 30 according to a movement path 28. Each actuation device 120 may be actuated simultaneously, thereby moving all dies 30 simultaneously with respect to one another to vary the size of the chamber 22.

An actuation device 120 may be operated electronically. Each actuation device 120 may be controlled by a common switch. Further, each actuation device 120 may be controlled by a computer.

Examples of suitable actuation devices 120 include but are not limited to linear motors available from Anorad Navigation, such as the LE Vacuum Compatible Linear Motor and PCLM Piezo Motor models; and linear motor tables available from Parker Automation, such as the LXR series tables. Desirably, actuation devices 120 may be suitable for use in nonmagnetic, vacuum and/or clean environments, and be insulated against high and low temperatures to which an apparatus 20 for shaping an article may be exposed.

While FIGS. 73 and 74 show an actuation device 120 for one or two dies 30 of the apparatus 20, actuation devices 120 and mounts 104 may be replicated accordingly with respect to each die 30 as would be understood by a person of ordinary skill in the art.

Figure 75:
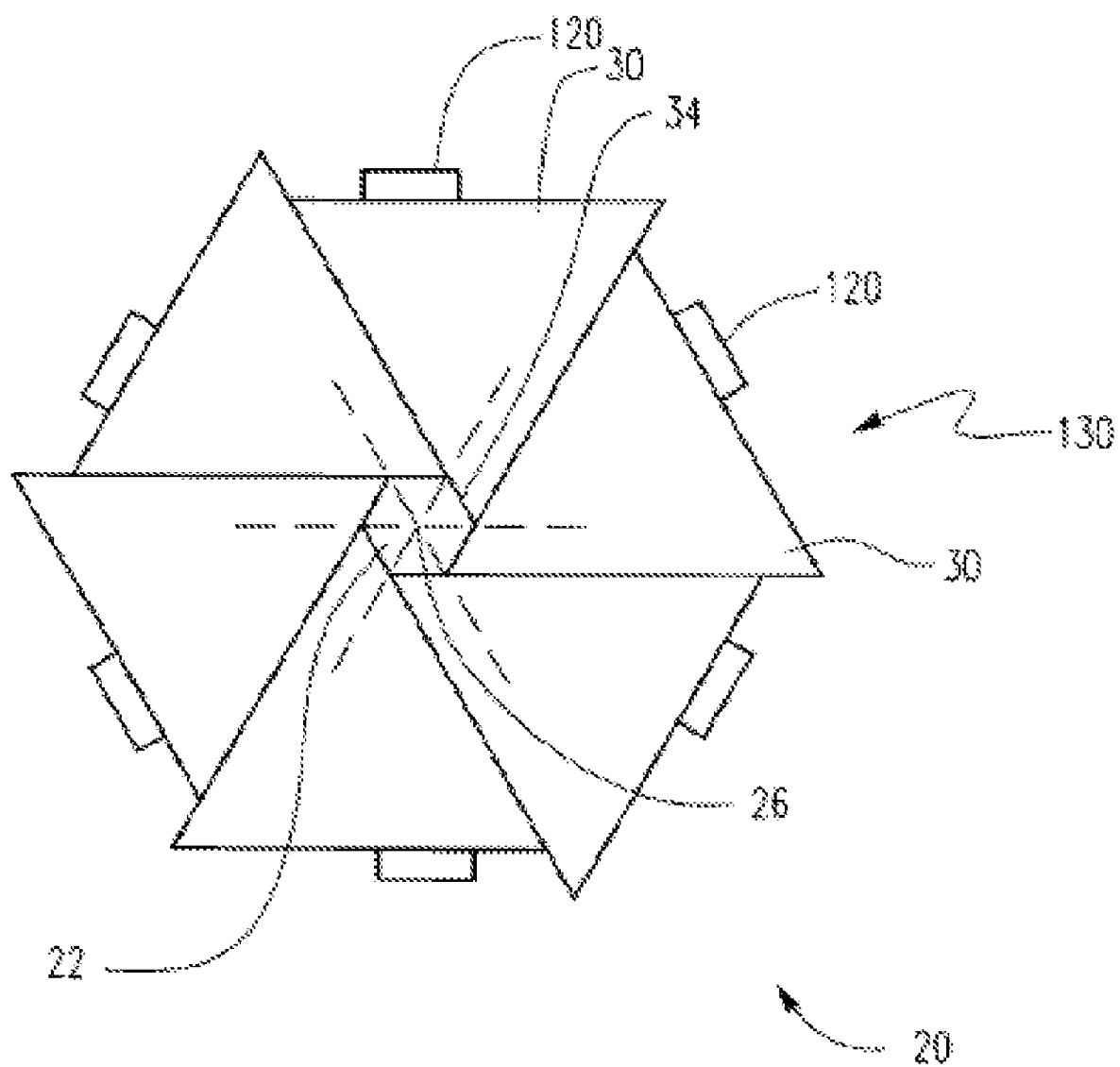
FIG. 75 shows an embodiment of an apparatus for shaping an article.
Figure 76:
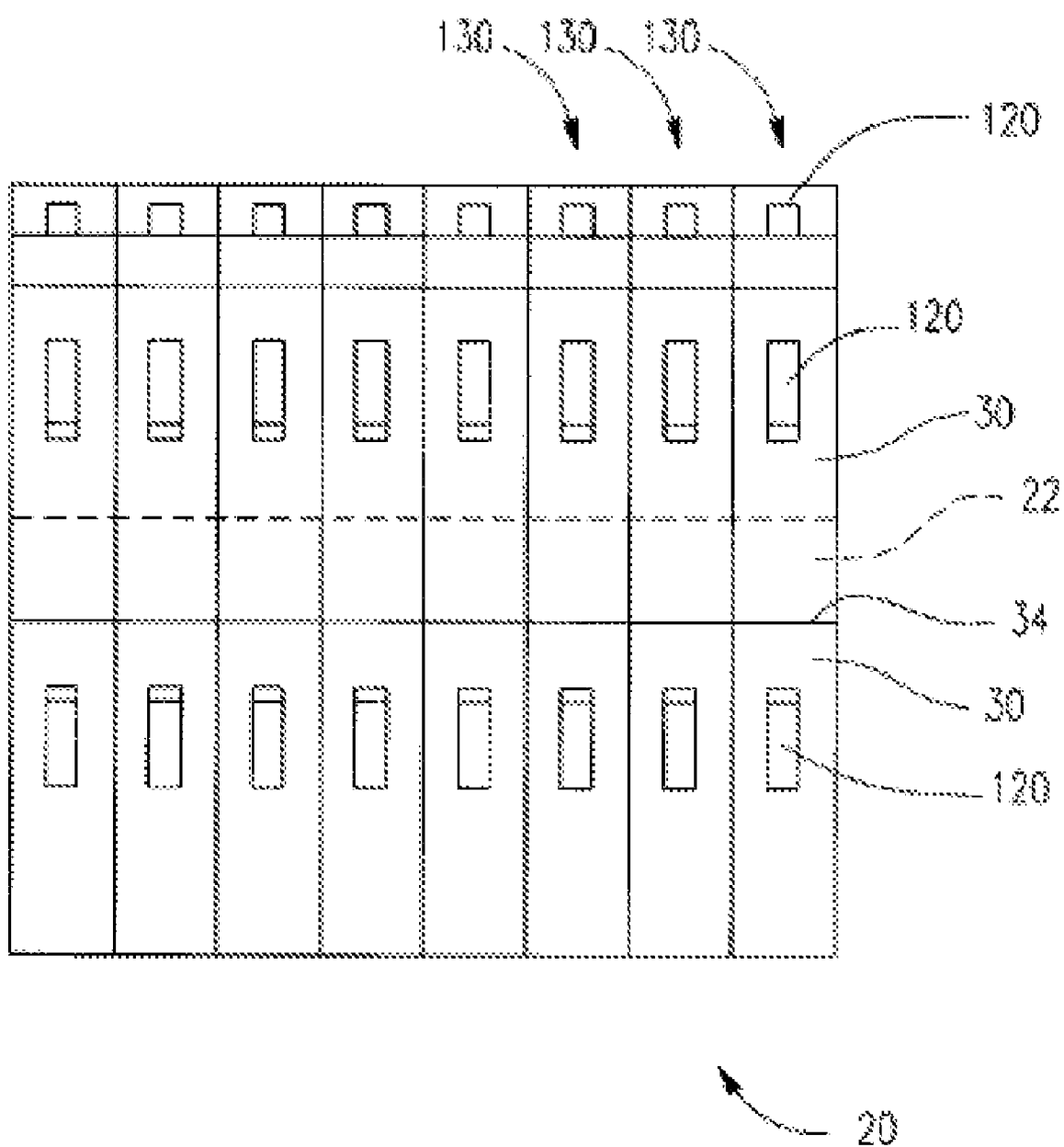
FIG. 76 shows a side view of the embodiment of the apparatus according to FIG. 75.
Figure 77:
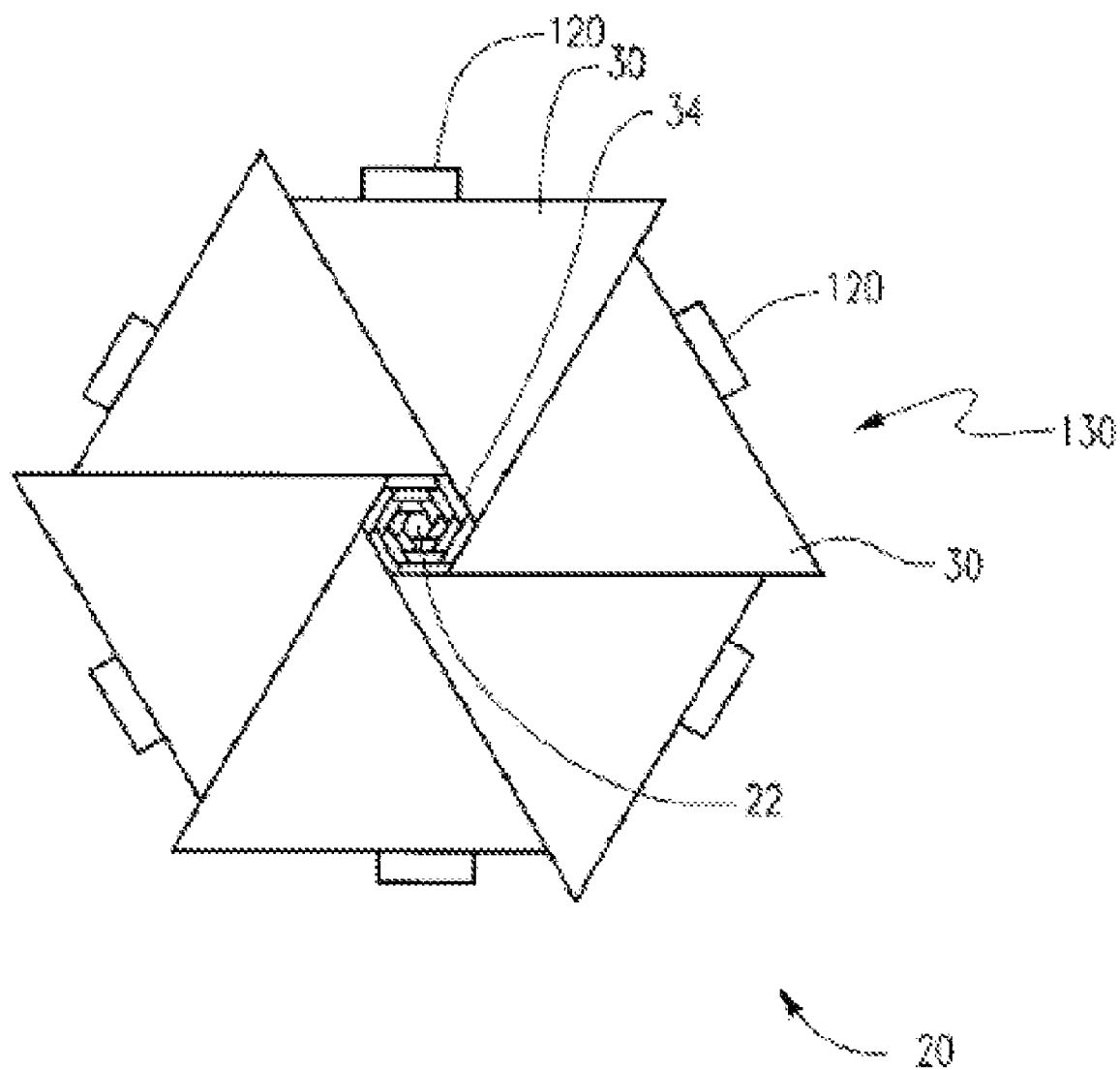
FIG. 77 shows the embodiment of FIG. 75 in another configuration.
Figure 78:
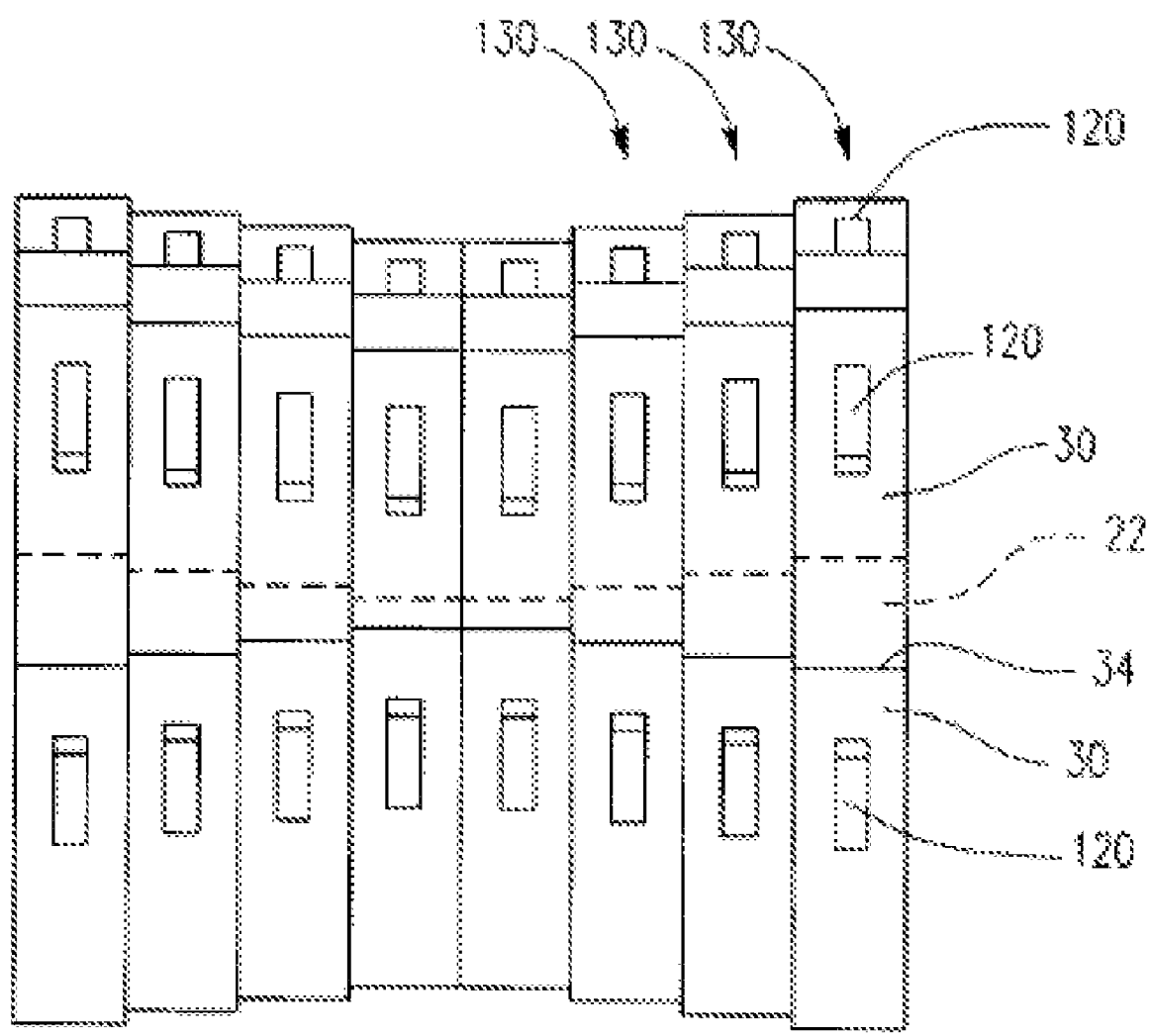
FIG. 78 shows a side view of the embodiment of the apparatus according to FIG. 77.

FIGS. 75-78 show another embodiment of an apparatus 20 for shaping an article which may comprise a plurality of die groups 130 arranged to form a chamber 22. Each die group 130 may comprise a plurality of dies 30 arranged to form a portion of the chamber 22. FIG. 76 is a side view of the apparatus 20 as shown in FIG. 75. FIG. 78 is a side view of the apparatus 20 as shown in FIG. 77.

The chamber 22 may extend the length of the apparatus 20. The chamber 22 may include a number of independently adjustable portions defined by the independent die groups 130 (as best shown in FIG. 78). The apparatus 20 may also be characterized as having a plurality of chambers 22, each chamber 22 defined by a die group 130.

Each die group 130 may be formed from a plurality of dies 30 arranged circumferentially about a zero point 26 to form a portion or length of the chamber 22. Each die group 130 may further be formed according to any of the embodiments of an apparatus for shaping an article as described herein. Die groups 130 may be placed adjacent to one another to form a chamber 22 with a plurality of independently adjustable longitudinal portions. Each die 30 may include a contacting surface 34 that may contact an article placed within the chamber 22 as the size of the chamber 22 is varied. The size and cross-sectional shape of each portion of the chamber 22 may be varied by moving the dies 30 of an appropriate die group 130 with respect to one another as described herein with respect to any of the other embodiments.

FIGS. 75 and 76 show the apparatus 20 having each die group 130 arranged according to a similar configuration. Thus, the size and shape of each portion of the chamber 22 is similar along the length of the chamber 22. FIGS. 77 and 78 show the apparatus arranged according to another configuration, wherein the various die groups 130 have been arranged to provide the chamber 22 with a contoured shape, specifically an "hourglass" shape. As the number of die groups 130 that are used to form the chamber 22 increases, the contours of the chamber 22 may become smoother along the length of the chamber 22.

The apparatus 20 may be configured to provide a chamber 22 having any suitable contoured shape. Once the die groups 130 have been configured to provide a chamber 22 having a desired shape, all of the dies 30 may be moved simultaneously to collectively increase or reduce the size of the chamber 22 while maintaining the geometrical shape of the chamber 22 along its length. Further, all of the dies 30 may be moved simultaneously to collectively increase or reduce the size of the chamber 22 while also changing the geometrical shape of the chamber 22 along its length.

The dies 30 of the apparatus 20 may be moved according to any of the methods or structure described herein. As shown in FIGS. 75-78, each die 30 may be moved by an actuation device 120. Each die 30 may be provided with an independent actuation device 120, and thus may be movable independently from all of the other dies.

In some embodiments, an actuation device may comprise a piezomotor, such as a PiezoLEGS motor available from PiezoMotor Uppsala AB, Sylveniusgatan 5D SE-754 50 Uppsala, Sweden. PiezoLEGS motors are available is sizes as small as 1 mm in width.

Using small and/or thin actuation devices 120 to control the movement of dies 30 of the apparatus 20 may allow for die groups 130 which each provide 1 mm or less of the chamber 22 length. As the amount of chamber length provided by each die group 130 decreases, the contours which may be provided along the length of the chamber 22 may become more continuous.

Any of the embodiments of an apparatus 20 for shaping an article described herein may include appropriate structure for moving the dies 30 as disclosed and discussed with respect to FIGS. 69-78, as well as any other methods disclosed herein. Further, any other embodiment described herein may include thin dies which may provide a chamber length of 1 mm or less.

Any of the dies 30 of any of the embodiments described herein may be made of any suitable, hard material including hardened steel. Desirably, the blades will be made of a material such as zirconia ceramic. Blades made of zirconia ceramic may be used without lubrication. Furthermore, because of their low thermal conductivity, they may be used to create a highly insulated chamber suitable for cryogenic processing of martensite in nitinol stents.

Any of the embodiments of the invention described herein or any of the features of any of the embodiments may be combined with other embodiments or features of other embodiments to form further embodiments of the invention. For example, an apparatus may be formed having a first plurality of dies arranged to form a first chamber and a second plurality of dies arranged to form a second chamber. The first chamber may be offset from the second chamber. The first chamber may have a different cross-sectional shape and a larger area than the second chamber. The second chamber may include a taper. Such an embodiment may be useful in reducing the size of a bifurcated stent.

Various embodiments of an apparatus for shaping an article according to the invention may be defined by a single chamber or a plurality of chambers. At least a portion of each chamber may be bounded by dies which extend the entire length of the portion of the chamber.

An iris as described herein may have the shape of a regular polygon or a non-regular polygon. An iris may further have a circular, oval, or otherwise curved shape. Thus, dies may be provided with curvature, thereby imparting the chamber and iris with curvature.

Further embodiments of the invention may be formed by arranging two or more embodiments as herein described in an end-to-end arrangement to form a substantially continuous chamber having multiple portions. For example, the embodiment of FIG. 2 may be placed in an end-to-end arrangement with the embodiment of FIG. 6. The resulting embodiment may include a chamber having a first portion having a regular cross-sectional shape and a second portion having a nonregular cross-sectional shape. If desired, the two portions may be arranged such that the longitudinal axis of the first chamber is offset from the longitudinal axis of the second chamber.

Any of the embodiments described herein may be cooled using cooling fluid. The cooling fluid may be a liquid cryogenic. Exemplary cryogenics include liquid nitrogen, argon or carbon dioxide although other cryogens may also be used. The cooling fluid may also be a chilled gas such as air. The cooling fluid may also be a cooled inert gas such as nitrogen, argon or other inert gasses.

The chamber formed by the dies may comprise a highly insulated chamber which is suitable for cryogenic processing of martensite in nitinol stents. The chamber may be maintained at −80° C. and a nitinol stent inserted therein. Upon equilibration of the temperature of the stent, the dies may be moved inward to reduce the diameter of the stent. The stent is thus reduced in diameter while being maintained in a martensitic state.

Cryogenic temperatures may be beneficial during the processing of drug coated stents. Low temperatures may stiffen a drug coating and therefore make the coating more resistant to damage during stent crimping.

Any of the embodiments described herein may also be heated. For example, the dies 30 may be heated to temperatures of 60° C. or greater. Direct heat may be applied to the dies, or heated fluid may be moved through the dies, the chamber or between the dies. Further, each die may include a heating element, such as an electrical resistor, for the generation of heat. A heating element may be contained within the die.

Heat may soften an article placed within the chamber, such as a balloon, which can allow for a better embedment of a stent into the balloon when the apparatus 20 is used to crimp a stent onto a balloon or delivery catheter. Further, a folded balloon may be placed in the chamber of an apparatus, and the temperature of the chamber and the pressure exerted upon the balloon by the chamber may be increased, thereby creasing the balloon folds and allowing a reduction in the final diameter of the balloon in an unexpanded state.

The invention further comprises methods of reducing the size of stents having portions of varying diameter, tapers, bifurcations, non-circular cross-sections, portions having differing longitudinal axes, and the like. Methods of reducing the size of stents may utilize any of the inventive devices disclosed herein. Methods of shaping articles, such as reducing the size of stents, may further include the simultaneous shaping of multiple articles disposed in an apparatus for shaping an article.

A method of reducing a stent in cross-section may comprise providing a stent crimper comprising a plurality of movable dies arranged to form a chamber whose size may be varied by moving the dies. The chamber may have a length from a first end to a second end. A first portion of a stent may next be disposed within the chamber, and the size of the chamber may be reduced, thereby reducing the diameter of the first portion of the stent. The stent may then be repositioned having a second portion of the stent disposed within the chamber, and the size of the chamber may be reduced, thereby reducing the diameter of the second portion of the stent. The diameter of the first portion may be different than the diameter of the second portion. The longitudinal axis of the first portion of the stent may be offset from the longitudinal axis of the second portion of the stent.

A method of reducing a bifurcated stent in cross-section may comprise providing a stent crimper comprising a plurality of movable dies arranged to form a chamber whose size may be varied by moving the dies. The chamber may have a length from a first end to a second end. The dies may be configurable to provide the chamber with at least two regions, the cross-section of the first region being different than the cross-section of the second region. A bifurcated stent may next be disposed within the chamber, and the size of the chamber may be reduced. The reduction may shape a first portion of the stent with a first shape and a second portion of the stent with a second shape of different geometry from the first shape.

Another method of reducing a stent in cross-section may comprise providing a stent crimper comprising a plurality of movable dies arranged to form a chamber whose size may be varied by moving the dies. The chamber may have a length from a first end to a second end. The dies may be configurable to provide at least a portion of the chamber with a smoothly tapering shape. A stent may next be disposed within the chamber, and the size of the chamber may be reduced so that the blades contact the stent and reduce the cross-section of the stent and impart a taper to the stent.

A method of crimping two or more marker bands to a catheter tube may comprise providing an apparatus comprising a plurality of movable dies arranged to form a chamber whose size may be varied by moving the dies. The chamber may have a length from a first end to a second end. The dies may be configurable so that the chamber includes at least two enlarged regions whose cross-sections are larger than the cross-section of the remainder of the chamber. A catheter tube with two or more marker bands disposed thereabout may be placed in the chamber. The size of the chamber may then be reduced so as to contact the marker bands and compress them onto the catheter. Each marker band may be disposed in a region of the chamber having a larger cross-section.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of some of the various embodiments of the invention. Those skilled in the art may recognize other equivalents to the specific embodiments described herein which equivalents are intended to be encompassed by the claims attached hereto.

The invention claimed is:

1. A method of reducing a stent in cross-section comprising the steps of:
    providing an apparatus for reducing the size of a stent comprising a plurality of movable dies arranged to form a chamber whose size may be varied by moving the dies, the chamber having a length from a first end of the chamber to a second end of the chamber, the dies configurable to provide the chamber with at least a first region and a second region, the cross-section of the first region being different than the cross-section of the second region;
    disposing a stent in the chamber;
    reducing the size of the chamber so as to shape a first portion of the stent with a first geometric shape and a second portion of the stent with a second geometric shape of a different geometry from the first geometric shape.

2. The method of claim 1 wherein the first geometric shape is substantially elliptical and the second geometric shape is substantially circular.

3. The method of claim 2 wherein the first region of the chamber has a longitudinal axis which is offset from a longitudinal axis of the second portion.

4. The method of claim 3 wherein the stent is a bifurcated stent and includes at least one catheter extending therethrough.

5. The method of claim 4 wherein the bifurcated stent includes a second catheter extending therethrough, the second catheter extending though a sidewall.

6. The method of claim 1 wherein each of the dies extends along the entire length of the chamber.

7. The method of claim 1 further comprising the step of providing a taper to at least a portion of the stent.

8. The method of claim 1, wherein at least two stents may be disposed in the chamber, and the stents may be shaped simultaneously.

9. The method of claim 8, wherein the stents are shaped differently from one another after shaping.

10. A method of reducing a stent in cross-section, the method comprising the steps of:
    providing an apparatus for reducing the size of a stent comprising a plurality of movable dies arranged to form a chamber whose size may be varied by moving the dies, the chamber having a length from a first end of the chamber to a second end of the chamber, the dies configurable to provide the chamber with at least a first region and a second region, wherein the first region of the chamber has a longitudinal axis which is offset from a longitudinal axis of the second region;
    disposing a stent in the chamber;
    reducing the size of the chamber so that the dies contact the stent and reduce the cross-section of the stent.

11. The method of claim 10 wherein each of the dies extend along the entire length of the chamber.

12. The method of claim 10 wherein the longitudinal axis of the first region of the chamber is substantially parallel to the longitudinal axis of the second region of the chamber.

13. The method of claim 10 wherein the first region of the chamber is comprised of a first set of dies and the second region of the chamber is comprised of a second set of dies.

14. A method of crimping at least one marker band to a catheter tube comprising the steps of:
    providing an apparatus comprising a plurality of movable dies arranged to form a chamber whose size may be varied by moving the dies, the chamber having a length from a first end of the chamber to a second end of the chamber, the dies configurable so that the chamber includes a first enlarged region, a second enlarged region, and a nominal portion disposed between the first enlarged region and the second enlarged region, wherein the two enlarged regions have cross-sections larger than a cross-section of the nominal portion of the chamber;

placing a catheter tube with at least one marker band disposed thereabout in the chamber;

reducing the size of the chamber so as to contact the marker band and crimp the marker band onto the catheter, the marker band disposed in a region of the chamber having a larger cross-section.

15. The method of claim 14 wherein each of the dies extends the length of the chamber.

16. The method of claim 14 further comprising placing a stent about the catheter within the nominal portion of the chamber and reducing the size of the chamber so as to reduce the diameter of the stent.

17. The method of claim 16, wherein the reduction of the stent size and crimping of the marker bands occurs simultaneously.

18. The method of claim 16, wherein at least two marker bands may be disposed about the catheter tube, and the marker bands may be crimped simultaneously.

19. The method of claim 16, wherein the marker band is crimped to a noncircular shape.

20. A method of shaping a medical device comprising:

providing an apparatus for shaping a medical device comprising a plurality of movable dies arranged to form a chamber whose size may be varied by moving the dies, the chamber having a length from a first end of the chamber to a second end of the chamber, each of the dies having a contacting surface for contacting the medical device to be shaped, the contacting surface of at least one of the dies being non-planar in the longitudinal direction of the chamber;

disposing a medical device in the chamber;

reducing the size of the chamber to impart the three dimensional shape of the chamber to the medical device.

21. The method of claim 20, wherein the medical device is a guidewire.

22. The method of claim 20, wherein the medical device is a catheter.

23. The method of claim 20, wherein the medical device is a balloon precursor.

24. The method of claim 23, further comprising the step of providing pressurized inflation fluid to an interior of the balloon precursor to inflate a balloon until the balloon contacts the chamber along the entire length of the balloon.

* * * * *